United States Patent [19]

Iwaki et al.

[11] Patent Number: 5,284,599
[45] Date of Patent: Feb. 8, 1994

[54] MESOMORPHIC COMPOUND, LIQUID CRYSTAL COMPOSITION CONTAINING SAME, LIQUID CRYSTAL DEVICE USING SAME DISPLAY APPARATUS

[75] Inventors: Takashi Iwaki, Machida; Takao Takiguchi, Tokyo; Takeshi Togano, Yokohama; Yoko Yamada; Shinichi Nakamura, both of Atsugi, all of Japan

[73] Assignee: Canon Kabushiki Kaisha, Tokyo, Japan

[21] Appl. No.: 915,888

[22] Filed: Jul. 20, 1992

Related U.S. Application Data

[62] Division of Ser. No. 643,377, Jan. 22, 1991, Pat. No. 5,236,619.

[30] Foreign Application Priority Data

Jan. 22, 1990 [JP] Japan .................. 2-012065
Jan. 30, 1990 [JP] Japan .................. 2-019725
Nov. 29, 1990 [JP] Japan .................. 2-332694

[51] Int. Cl.$^5$ .................. C09K 19/34; C07D 277/62; C07D 239/02; C07D 211/70
[52] U.S. Cl. .................. 252/299.61; 548/152; 548/165; 548/169; 548/173; 548/179; 544/298; 544/316; 544/318; 544/333; 546/339; 546/346; 359/75; 359/104
[58] Field of Search .................. 252/299.01, 299.61, 252/299.63; 548/173, 152, 179, 165, 169; 544/298, 316, 318, 333; 546/339, 346; 359/75, 76, 103, 104

[56] References Cited

U.S. PATENT DOCUMENTS

| | | | |
|---|---|---|---|
| 4,153,343 | 5/1979 | Bloom et al. | 252/299.01 |
| 4,367,924 | 1/1983 | Clark et al. | 350/334 |
| 5,034,151 | 7/1991 | Shinjo et al. | 252/299.6 |
| 5,194,177 | 3/1993 | Nohira et al. | 252/299.61 |

FOREIGN PATENT DOCUMENTS

56-107216 8/1981 Japan .

OTHER PUBLICATIONS

Pavluchenko, Mol. Crystals Liquid Crystals, vol. 37, (1976), pp. 35–46.
Schadt "Applied Physics Letters", vol. 18, No. 4, pp. 127–128 (1971).
Wohlfahrt, "J. Prakt. Chem." vol. 66, p. 511 (1902).
Bogert et al. "J. Am. Chem. Soc.", vol. 46, 1308 (1924).
Chemical Abstracts, vol. 99, No. 12 (1983) 89610p.
Chemical Abstracts, vol. 87, No. 1 (1977) 4816q.

*Primary Examiner*—Philip Tucker
*Attorney, Agent, or Firm*—Fitzpatrick, Cella, Harper & Scinto

[57] ABSTRACT

A mesomorphic compound represented by the following formula (I):

$$R_1-A_1-B_1-A_2-R_2 \qquad (I),$$

wherein $R_1$ and $R_2$ respectively denote a linear or branched alkyl group having 3-18 carbon atoms capable of including one or non-neighboring two or more methylene groups which can be replaced with at least one species of —Z—,

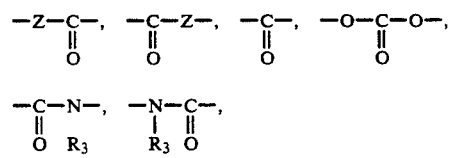

$CH=CH-$ and $-C\equiv C-$, wherein Z denotes —O— or —S— and $R_3$ denotes hydrogen or an alkyl group having 1-5 carbon atoms; $B_1$ denotes

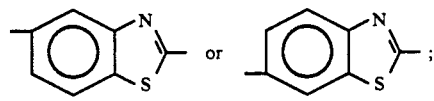

$A_1$ denotes a single bond, (Abstract continued on next page.)

5,284,599
Page 2
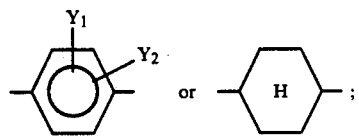  or 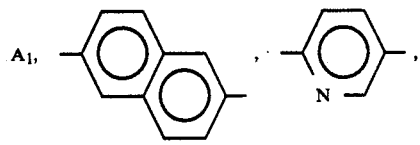 ;
$A_2$ denotes a single bond, $-A_3-$ or $-A_3-A_4-$ wherein $A_3$ and $A_4$ respectively denote any one of
$A_1$, 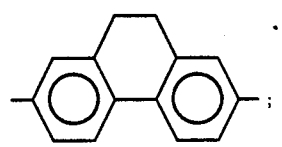 ,
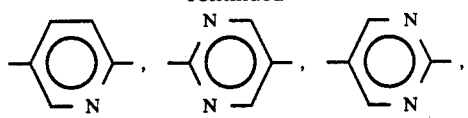
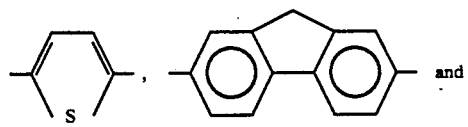
and $Y_1$ and $Y_2$ respectively denote any one of hydrogen, fluorine, chlorine, bromine, $-CH_3$, $-CN$ and $-CF_3$.
14 Claims, 4 Drawing Sheets

MESOMORPHIC COMPOUND, LIQUID CRYSTAL COMPOSITION CONTAINING SAME, LIQUID CRYSTAL DEVICE USING SAME DISPLAY APPARATUS

This application is a division of application Ser. No. 643,377, filed Jan. 22, 1991 now U.S. Pat. No. 5,236,619.

FIELD OF THE INVENTION AND RELATED ART

The present invention relates to a novel mesomorphic compound, a liquid crystal composition containing the compound, a liquid crystal device using the composition and a display apparatus, and more particularly to a novel liquid crystal composition with improved responsiveness to an electric field and a liquid crystal device using the liquid crystal composition for use in a liquid crystal display apparatus, a liquid crystal-optical shutter, etc.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of milli-seconds, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected or regions where a scanning electrode is not selected and a signal electrode is selected (which regions are so called "half-selected points"). If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. As a result, this leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed. However, any method is not sufficient to overcome the above-mentioned drawbacks. As a result, it is the present state that the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216, U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, ferroelectric liquid crystal materials developed heretofore cannot be said to satisfy sufficient characteristics required for a liquid crystal device including low-temperature operation characteristic, high-speed responsiveness, etc. Among a response time $\eta$, the magnitude of spontaneous polarization Ps and viscosity $\eta$, the following relationship exists: $\tau = \eta/(Ps \cdot E)$, where E is an applied voltage. Accordingly, a high response speed can be obtained by (a) increasing the spontaneous polarization Ps, (b) lowering the viscosity $\eta$, or (c) increasing the applied voltage E.

However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Further, if it is assumed that the operation temperature of an actual display device is 5°-40° C., the response speed changes by a factor of about 20, so that it actually exceeds the range controllable by driving voltage and frequency.

As described hereinabove, commercialization of a ferroelectric liquid crystal device requires a liquid crystal composition assuming a chiral smectic phase which has not only a large spontaneous polarization but also a low viscosity, a high-speed responsiveness and a small temperature-dependence of response speed.

SUMMARY OF THE INVENTION

An object of the present invention is to provide a mesomorphic compound, a liquid crystal composition, particularly a chiral smectic liquid crystal composition, containing the mesomorphic compound for providing a practical ferroelectric liquid crystal device, a liquid crystal device using the liquid crystal composition and having a high response speed and a smaller temperature-dependence of the response speed, and a display apparatus.

According to the present invention, there is provided a mesomorphic compound represented by the following formula (I):

$$R_1-A_1-B_1-A_2-R_2 \quad (I),$$

wherein $R_1$ and $R_2$ respectively denote a linear or branched alkyl group having 3-18 carbon atoms capable of including one or non-neighboring two or more methylene groups which can be replaced with at least one species of —Z—,

—CH=CH— and —C≡C—,
wherein Z denotes —O— or —S— and $R_3$ denotes hydrogen or an alkyl group having 1-5 carbon atoms; $B_1$ denotes

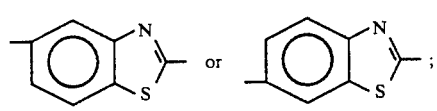

$A_1$ denotes a single bond,

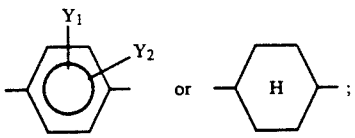

$A_2$ denotes a single bond, —$A_3$— or —$A_3$—$A_4$— wherein $A_3$ and $A_4$ respectively denote any one of $A_1$,

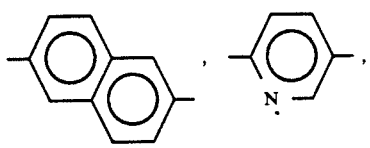

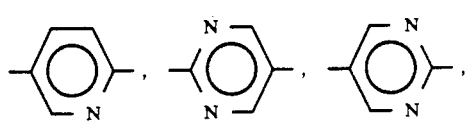

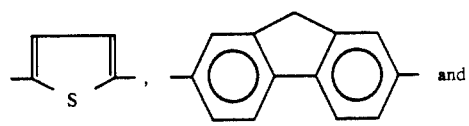

and $Y_1$ and $Y_2$ respectively denote any one of hydrogen, fluorine, chlorine, bromine, —CH$_3$, —CN and —CF$_3$.

According to the present invention, there is further provided a chiral smectic liquid crystal composition containing at least one species of the mesomorphic compound as described above.

The present invention further provides a liquid crystal device comprising a pair of substrates and such a liquid crystal composition as described above disposed between the electrode plates, and a display apparatus comprising the liquid crystal device.

Further, according to the present invention, there is provided an optically active mesomorphic compound represented by the following formula (II):

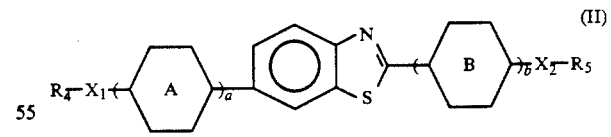

wherein $R_4$ and $R_5$ respectively denote an alkyl group having 1-18 carbon atoms capable of having a substituent, at least one of $R_4$ and $R_5$ has an asymmetric carbon atom connected to halogen; $X_1$ and $X_2$ respectively denote any one of a single bond, —O—,

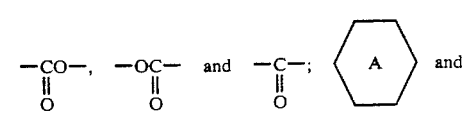

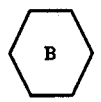 respectively denote any one of

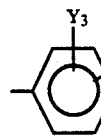 ,  ,  ,

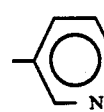 ,  , and

 ;

and $Y_3$ and $Y_4$ respectively denote any one of hydrogen, fluorine, chlorine, bromine, $-CH_3$, $-CN$ and $-CF_3$; and a and b respectively denote 0 or 1.

According to the present invention, there is further provided a chiral smectic liquid crystal composition containing at least one species of the above-mentioned optically active mesomorphic compound.

The present invention further provides a liquid crystal device comprising a pair of substrates and such a liquid crystal composition as described above disposed between the electrode plates, and a display apparatus comprising the liquid crystal device.

These and other objects, features and advantages of the present invention will become more apparent upon a consideration of the following description of the preferred embodiments of the present invention taken in conjunction with the accompanying drawings.

DETAILED DESCRIPTION OF THE INVENTION

Figure 1:
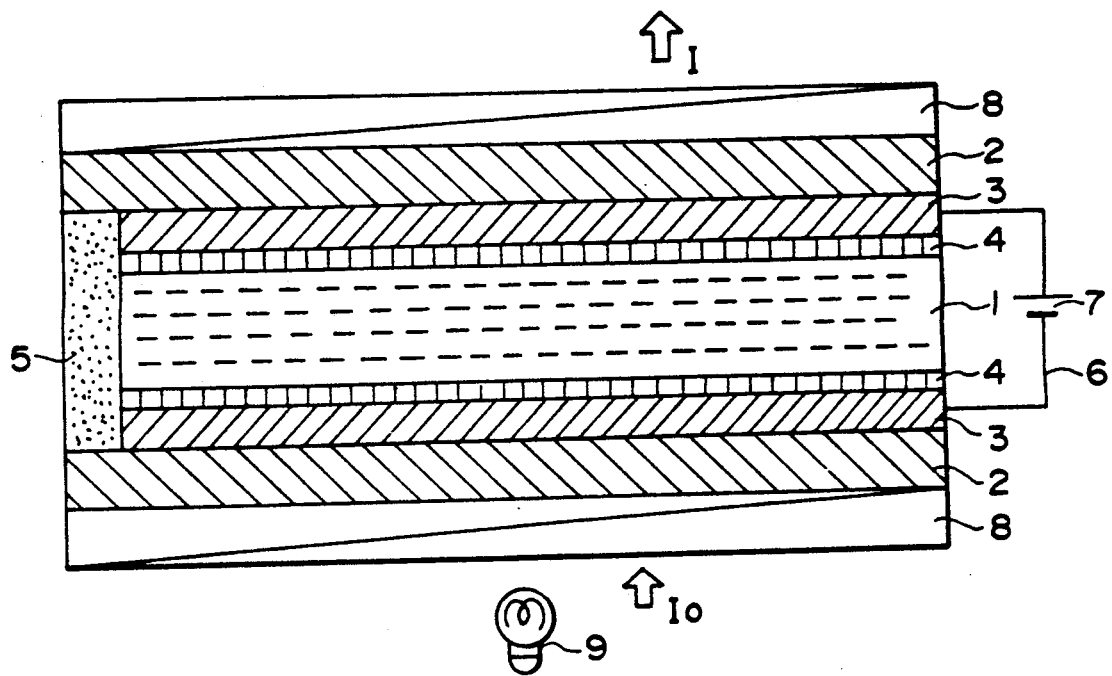
FIG. 1 is a schematic sectional view of a liquid crystal display device using a liquid crystal composition assuming a chiral smectic phase.

In the formula (I) as described above, preferred examples of $R_1$ and $R_2$ may include the following combinations (i) to (vi):

(i) $R_1$ is n-$C_mH_{2m+1}$—$X_3$— and
$R_2$ is n-$C_lH_{2l+1}$—$X_4$—;

(ii) $R_1$ is n-$C_mH_{2m+1}$—$X_3$— and
$R_2$ is $R_6CH(CH_2)_p X_4$—;
  |
  $CH_3$ (iii) $R_1$ is n-$C_mH_{2m+1}$—$X_3$— and
$R_2$ is $R_7O(CH_2)_q CH(CH_2)_r X_4$—;
  |
  $CH_3$ (iv) $R_1$ is $R_8$—$CH(CH_2)_r X_3O$— and
  |
  $CH_3$
$R_2$ is n-$C_mH_{2m+1}$—$X_4$—;

(v) $R_1$ is $R_8$—$CH(CH_2)_s X_3$— and
  |
  $CH_3$
$R_2$ is $R_6$—$CH(CH_2)_p X_4$;
  |
  $CH_3$ and (vi) $R_1$ is $R_8$—$CH(CH_2)_s X_3$— and
  |
  $CH_3$
$R_2$ is $R_7O(CH_2)_q CH(CH_2)_r X_4$—;
  |
  $CH_3$ wherein m and l respectively denote an integer of 3–17; p, r and s respectively denote an integer of 0–7; q denotes 0 or 1; $R_6$, $R_7$ and $R_8$ respectively denote a linear or branched alkyl group; $X_3$ denotes a single bond, —O—,

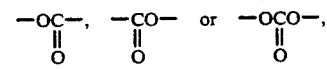

more preferably a single bond or —O—, particularly a single bond; and $X_4$ denotes a single bond, —O—,

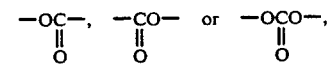

more preferably a single bond or —O—.

Preferred examples of $A_1$ may include a single bond and

 , more preferably a single bond. Preferred examples of $A_2$ may include

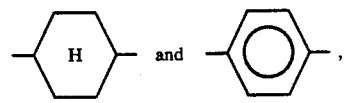

more preferably 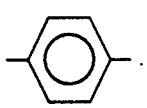.

Any one of $A_1$ and $A_2$ may preferably be a single bond.
Further, $B_1$ may preferably be

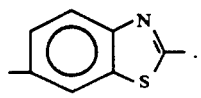

Heretofore, liquid crystals containing a benzothiazole ring have been shown in A. I. Pavluchenko et al., "Mol. Cryst. Liq. Cryst.", 37, 35 (1976). However, most of them are those containing a benzothiazole ring connected to another ring by a bonding group such as —COO—, —CH=CH—, —N=CH— or —N=N— and containing a terminal group such as a n-alkyl, n-alkoxy or —CN. The above liquid crystals includes only two species of compounds containing a benzothiazole ring directly connected to a benzene ring represented by the following formulas:

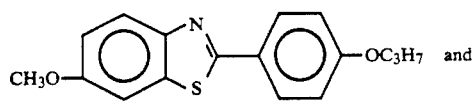 and

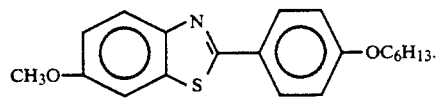

However, these compounds do not have two terminal groups both comprising an alkyl group having 3 or more carbon atoms, characteristic of the mesomorphic compound of the formula (I). Further, the above two compounds do not contain any terminal group having an asymmetric carbon atom connected to halogen, characteristic of the optically active mesomorphic compound of the formula (II).

Accordingly, the mesomorphic compounds of the formula (I) and (II) are not shown or suggested at all.

We have found that a benzothiazole derivative represented by the above-mentioned formula (I) comprising a benzothiazole ring alone or a benzothiazole ring directly connected to an aromatic ring or cyclohexane ring which is further connected to an alkyl group having 3 or more carbon atoms has a lower viscosity. In a case where the benzothiazole derivative comprising a benzothiazole ring directly connected to another ring is used, the benzothiazole derivative has a wide temperature range showing a mesomorphic phase. As a result, a liquid crystal composition showing a chiral smectic phase comprising at least one species of such a benzothiazole derivative and a liquid crystal device using the liquid crystal composition provide improved properties such as high speed responsiveness and decrease in temperature-dependence of response speed to provide a display apparatus having good display characteristic.

We have also found that a novel optically active mesomorphic compound represented by the abovementioned formula (II) comprising benzothiazole ring and at least one alkyl group having an asymmetric carbon atom connected to halogen. As a result, a liquid crystal composition showing a chiral smectic phase comprising at least one species of such a mesomorphic compound and a liquid crystal device using the liquid crystal composition have high speed responsiveness to provide a display apparatus having good display characteristics.

The mesomorphic compound represented by the general formula (I) may be synthesized through the following reaction scheme.

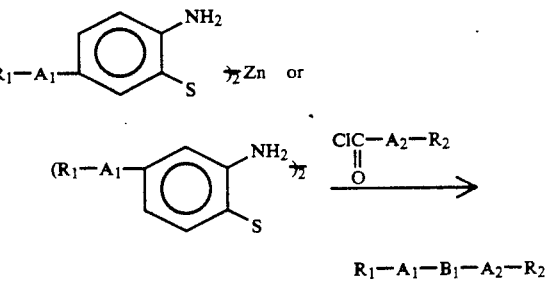

$$R_1-A_1-B_1-A_2-R_2$$

In the above, $R_1$, $R_2$, $A_1$, $A_2$ and $B_1$ are the same as defined in the general formula (I).

Aminobenzenethiol derivatives may be synthesized through methods disclosed in Th. Wohlfahrt, "J. Prakt. Chem.", 66, 511 (1902) and M. T. Bogert et al., "J. Am. Chem. Soc.", 46, 1308 (1924).

In a case where a methylene group in $R_1$ or $R_2$ adjacent to $A_1$ or $A_2$ is replaced with —Z—,

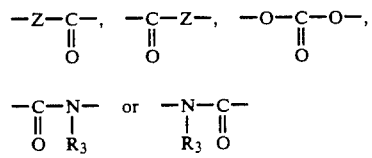

wherein Z denotes —O— or —S— and $R_3$ denotes hydrogen or an alkyl group having 1-5 carbon atoms, it is possible to form a group of $R_1-A_1-$ or $R_2-A_2-$ through the following steps (a) to (c): (a) The abovementioned replacing group combined with $A_1$ or $A_2$ is modified with addition of a protective group into a non-reactive or less reactive group such as —OCH$_3$,

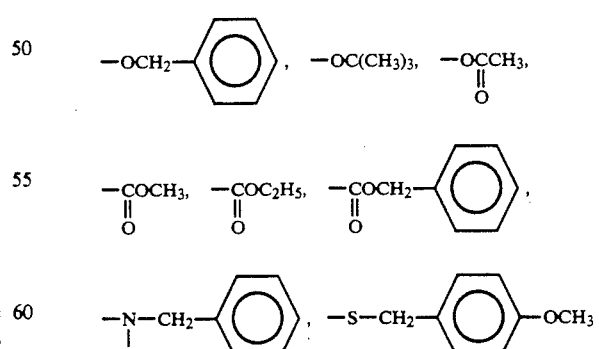

—S—C(CH$_3$)$_3$ capable of elimination reaction.

(b) Ring closure is effected to form a thiadiazole ring.

(c) The protective group is eliminated and then the $R_1-A_1-$ or $R_2-A_2-$ structure is formed.

Specific examples of the mesomorphic compounds represented by the above-mentioned general formula (I)

may include those shown by the following structural formulas.
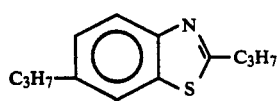 (I-1)
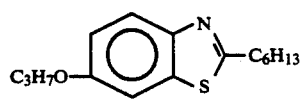 (I-2)
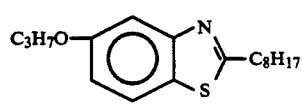 (I-3)
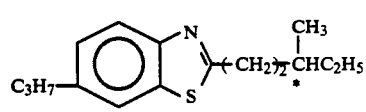 (I-4)
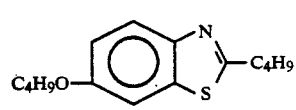 (I-5)
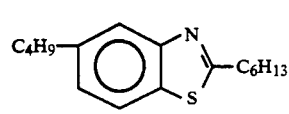 (I-6)
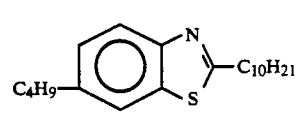 (I-7)
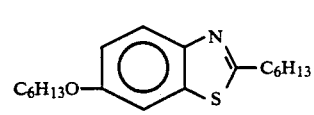 (I-8)
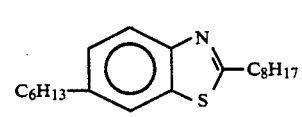 (I-9)
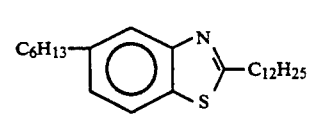 (I-10)
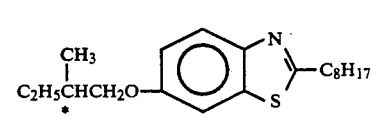 (I-11)
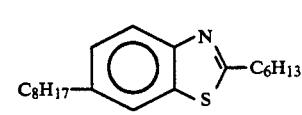 (I-12)
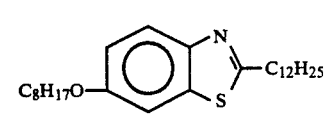 (I-13)

-continued
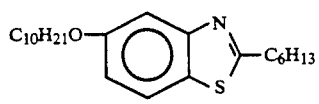 (I-14)
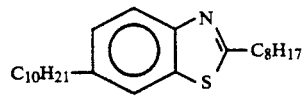 (I-15)
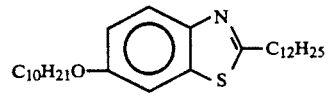 (I-16)
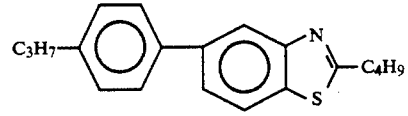 (I-17)
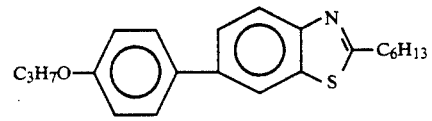 (I-18)
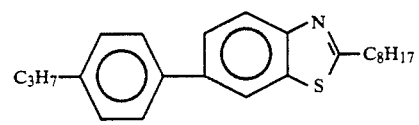 (I-19)
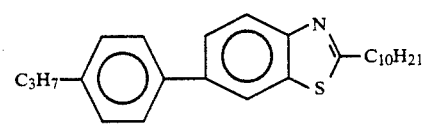 (I-20)
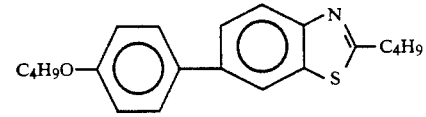 (I-21)
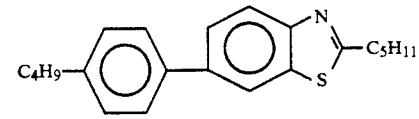 (I-22)
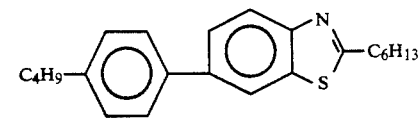 (I-23)
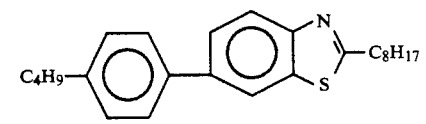 (I-24)
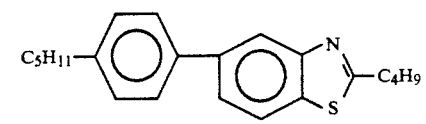 (I-25)

-continued
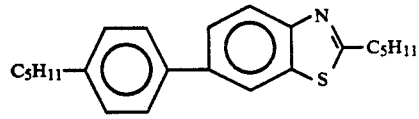 (I-26)
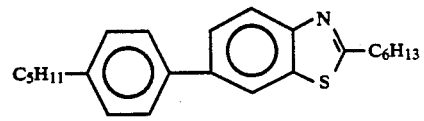 (I-27)
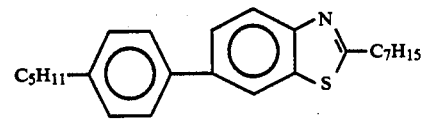 (I-28)
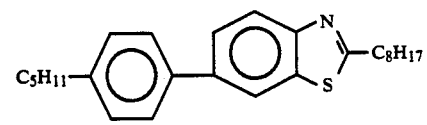 (I-29)
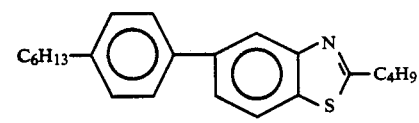 (I-30)
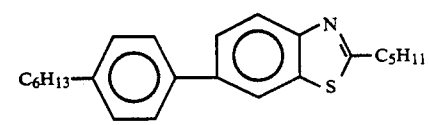 (I-31)
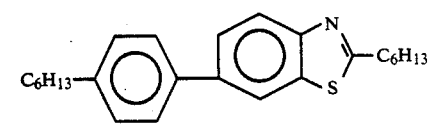 (I-32)
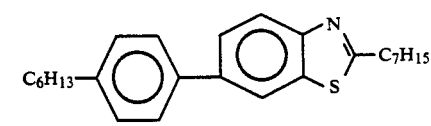 (I-33)
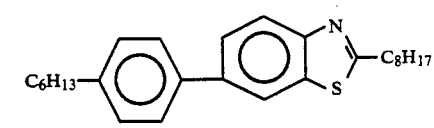 (I-34)
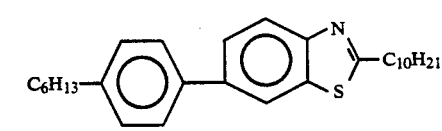 (I-35)
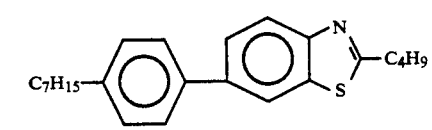 (I-36)
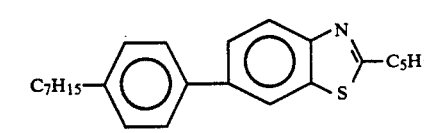 (I-37)

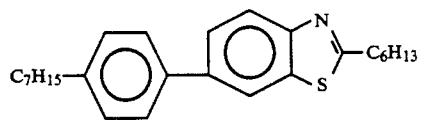 (I-38)
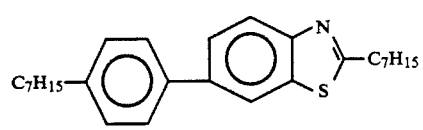 (I-39)
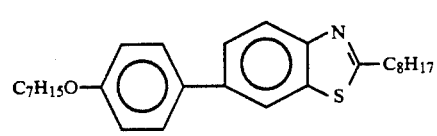 (I-40)
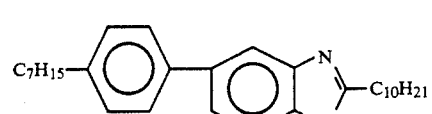 (I-41)
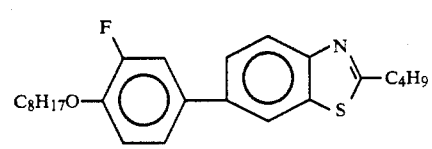 (I-42)
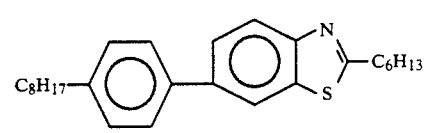 (I-43)
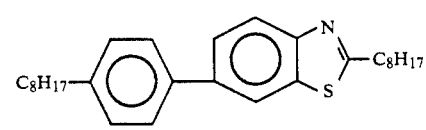 (I-44)
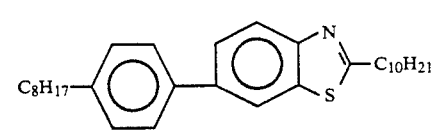 (I-45)
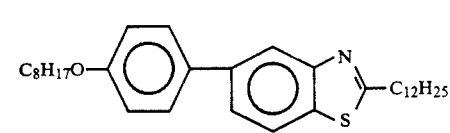 (I-46)
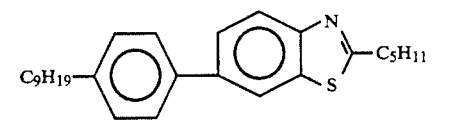 (I-47)
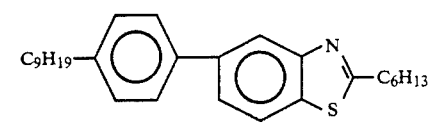 (I-48)

-continued
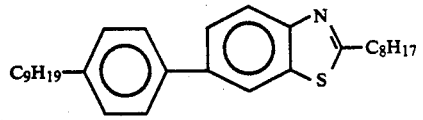 (I-49)
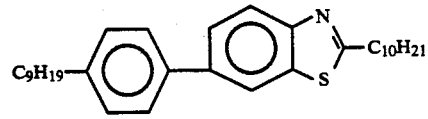 (I-50)
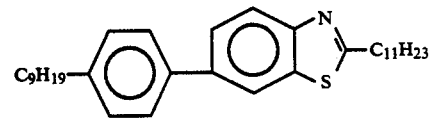 (I-51)
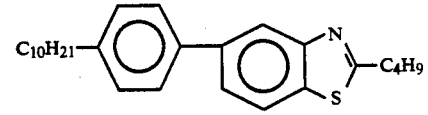 (I-52)
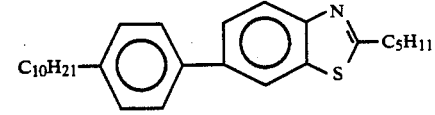 (I-53)
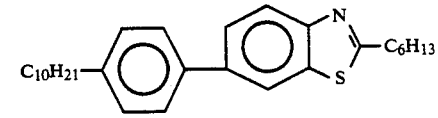 (I-54)
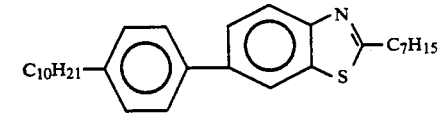 (I-55)
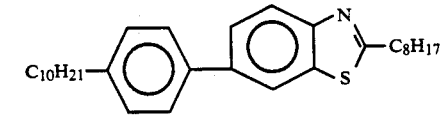 (I-56)
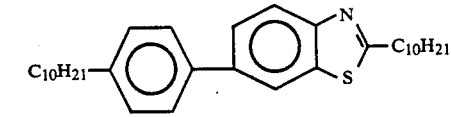 (I-57)
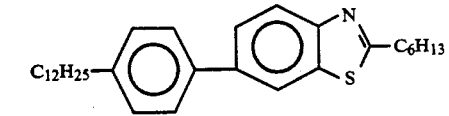 (I-58)
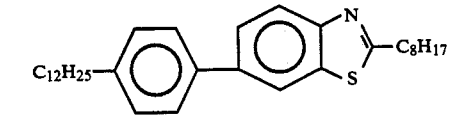 (I-59)
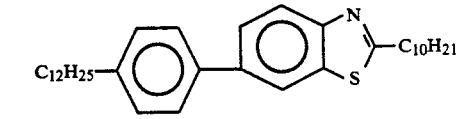 (I-60)

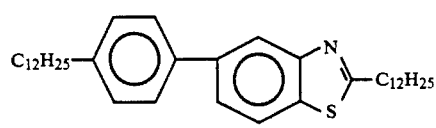
(I-61)
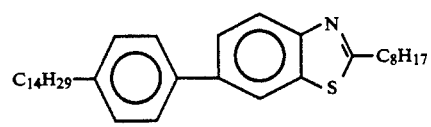
(I-62)
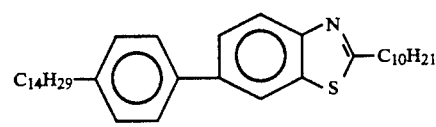
(I-63)
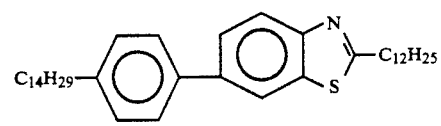
(I-64)
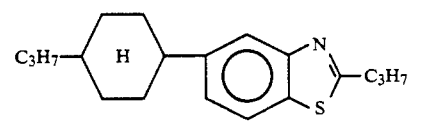
(I-65)
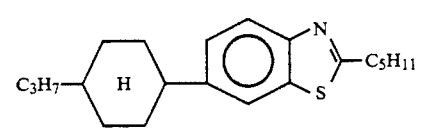
(I-66)
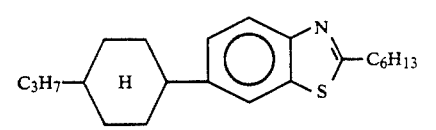
(I-67)
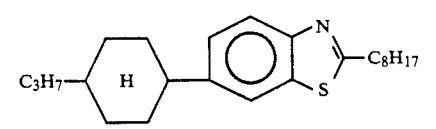
(I-68)
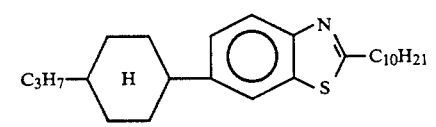
(I-69)
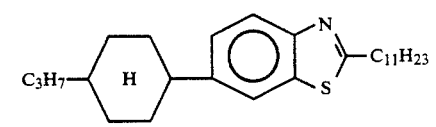
(I-70)
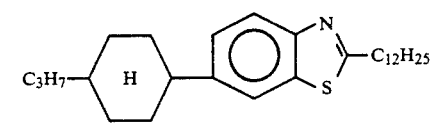
(I-71)

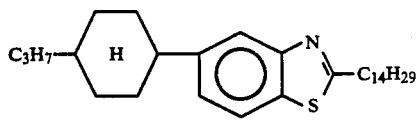 (I-72)
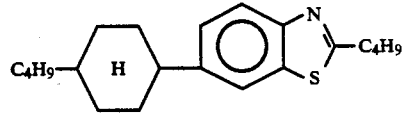 (I-73)
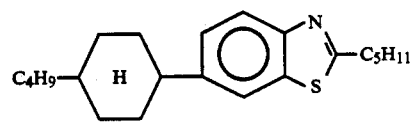 (I-74)
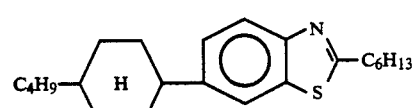 (I-75)
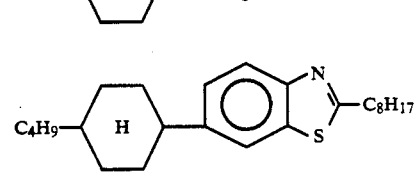 (I-76)
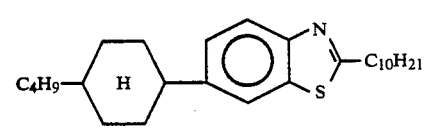 (I-77)
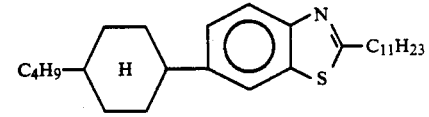 (I-78)
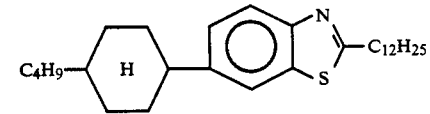 (I-79)
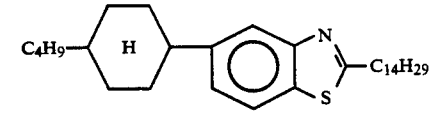 (I-80)
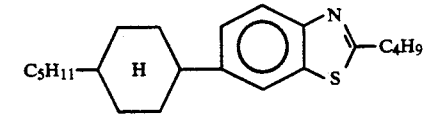 (I-81)
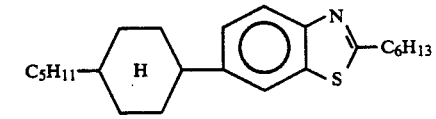 (I-82)
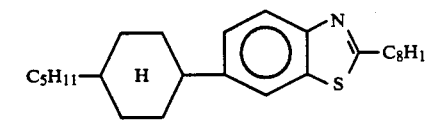 (I-83)

-continued
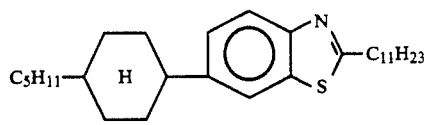 (I-84)
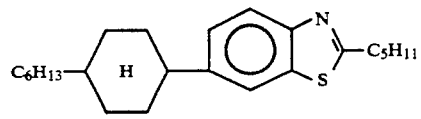 (I-85)
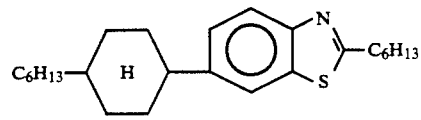 (I-86)
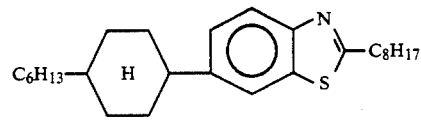 (I-87)
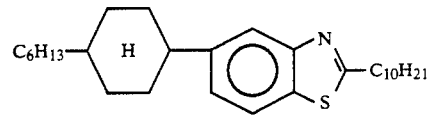 (I-88)
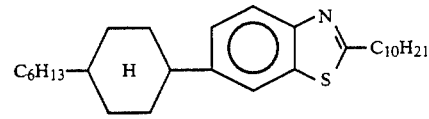 (I-89)
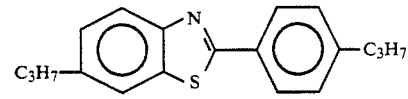 (I-90)
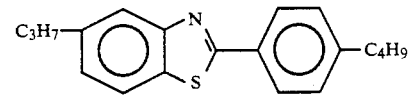 (I-91)
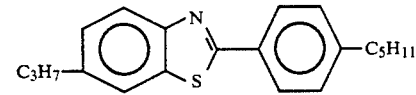 (I-92)
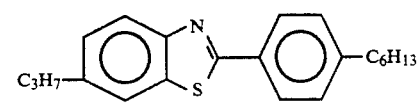 (I-93)
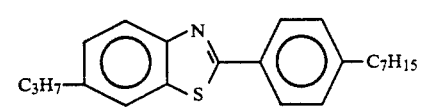 (I-94)
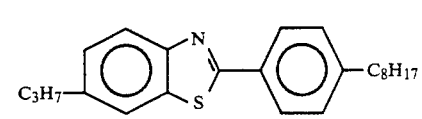 (I-95)

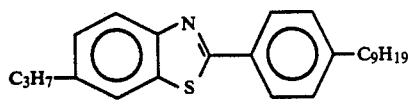 (I-96)
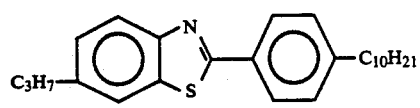 (I-97)
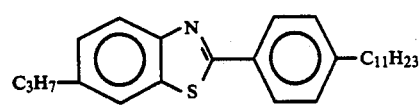 (I-98)
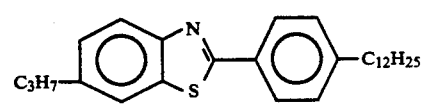 (I-99)
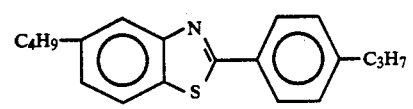 (I-100)
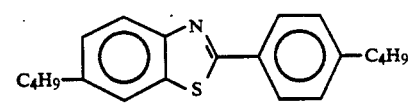 (I-101)
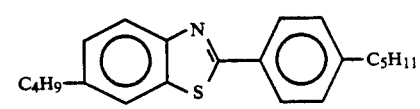 (I-102)
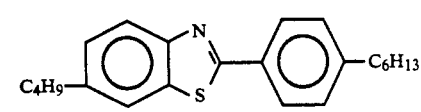 (I-103)
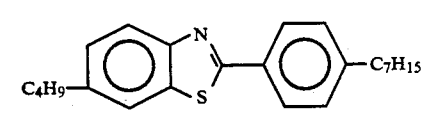 (I-104)
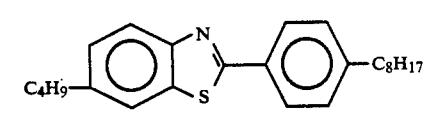 (I-105)
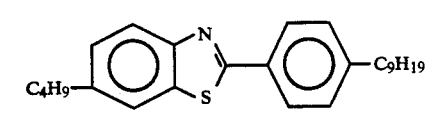 (I-106)
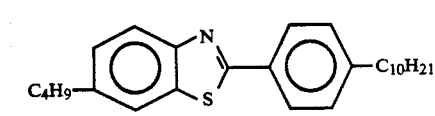 (I-107)
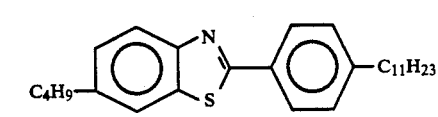 (I-108)
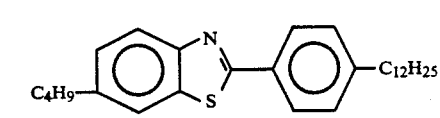 (I-109)

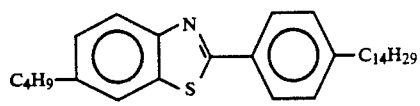 (I-110)
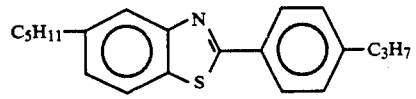 (I-111)
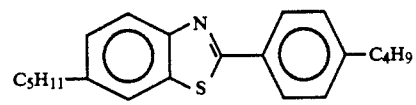 (I-112)
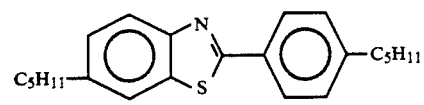 (I-113)
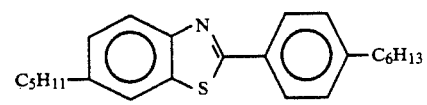 (I-114)
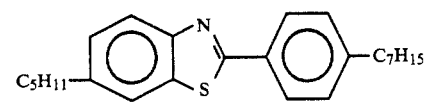 (I-115)
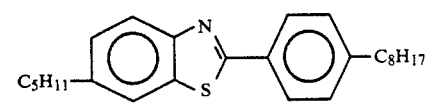 (I-116)
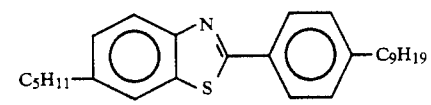 (I-117)
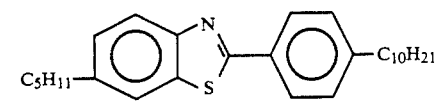 (I-118)
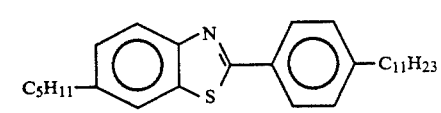 (I-119)
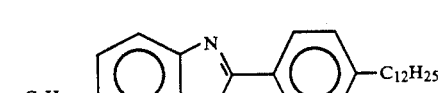 (I-120)
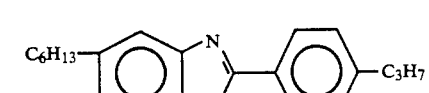 (I-121)
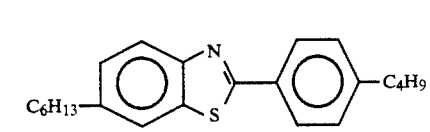 (I-122)

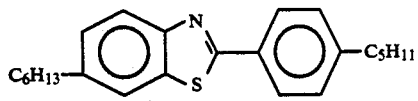 (I-123)
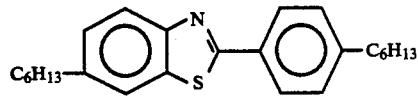 (I-124)
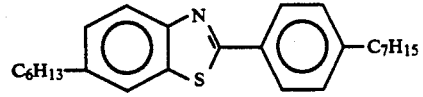 (I-125)
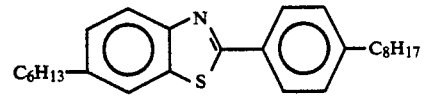 (I-126)
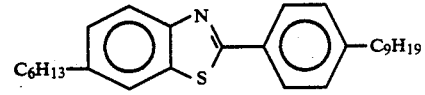 (I-127)
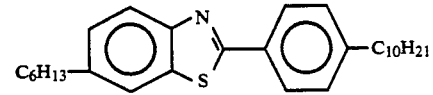 (I-128)
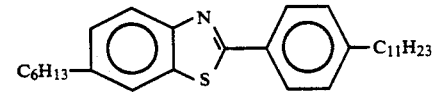 (I-129)
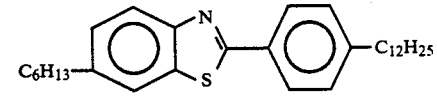 (I-130)
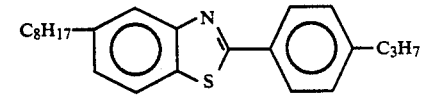 (I-131)
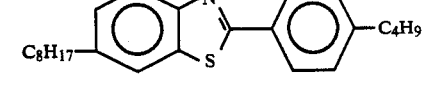 (I-132)
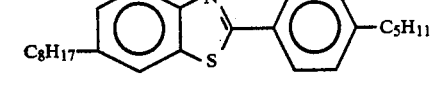 (I-133)
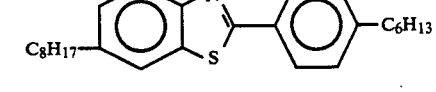 (I-134)
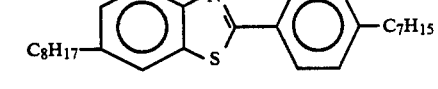 (I-135)

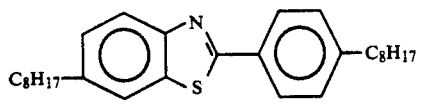 (I-136)
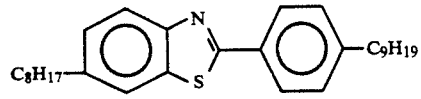 (I-137)
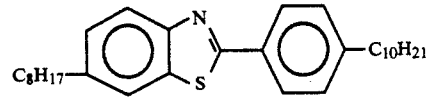 (I-138)
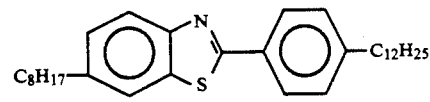 (I-139)
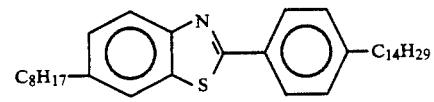 (I-140)
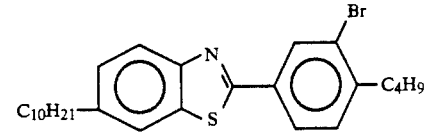 (I-141)
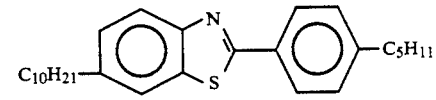 (I-142)
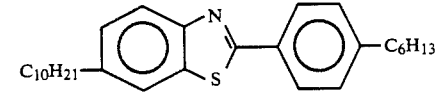 (I-143)
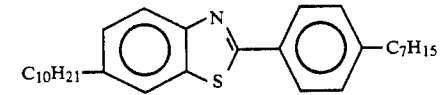 (I-144)
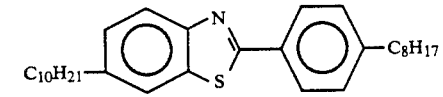 (I-145)
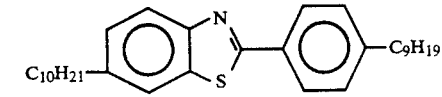 (I-146)
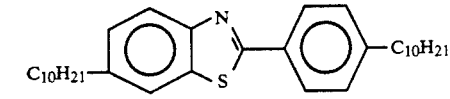 (I-147)
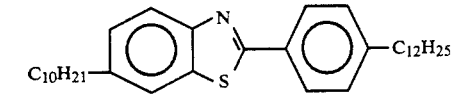 (I-148)

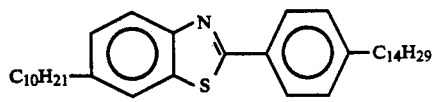 (I-149)
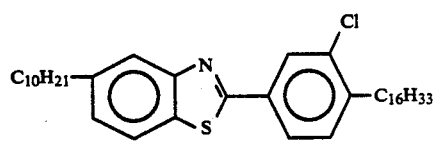 (I-150)
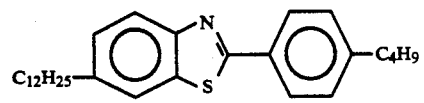 (I-151)
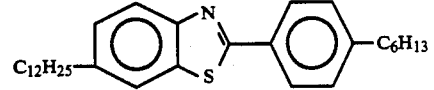 (I-152)
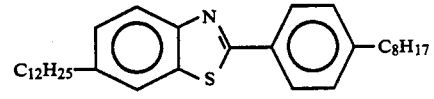 (I-153)
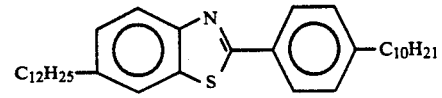 (I-154)
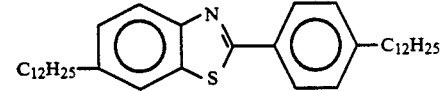 (I-155)
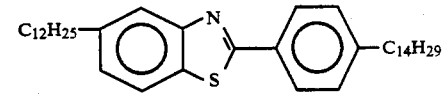 (I-156)
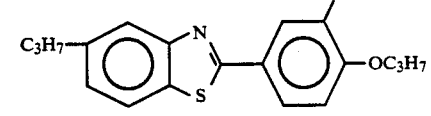 (I-157)
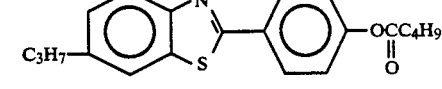 (I-158)
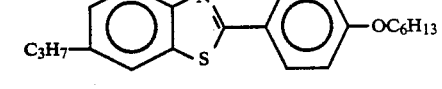 (I-159)
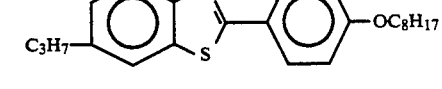 (I-160)
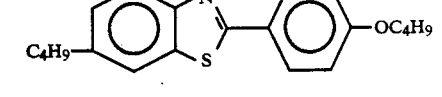 (I-161)

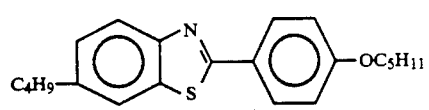 (I-162)
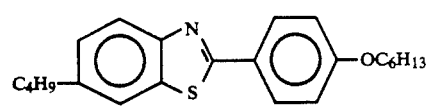 (I-163)
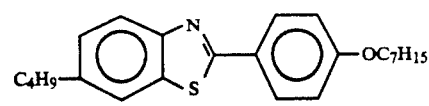 (I-164)
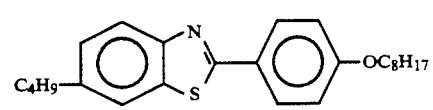 (I-165)
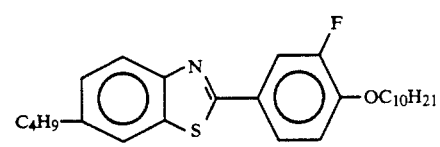 (I-166)
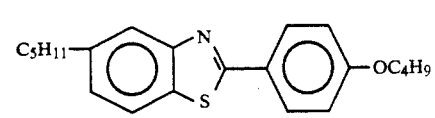 (I-167)
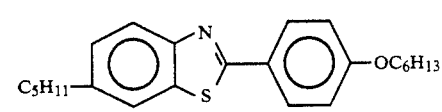 (I-168)
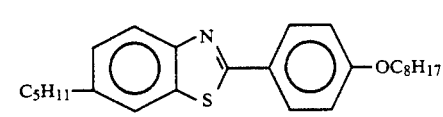 (I-169)
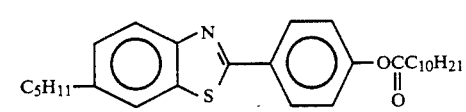 (I-170)
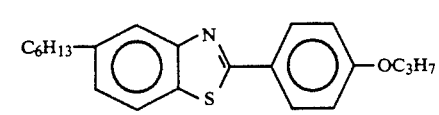 (I-171)
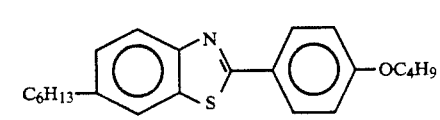 (I-172)
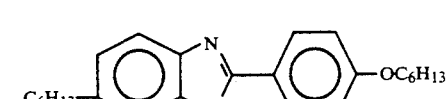 (I-173)
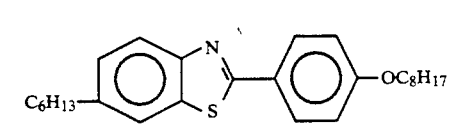 (I-174)

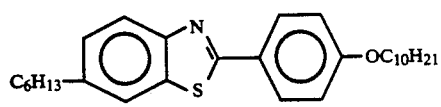 (I-175)
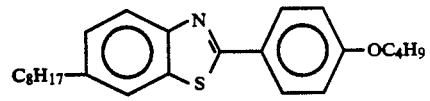 (I-176)
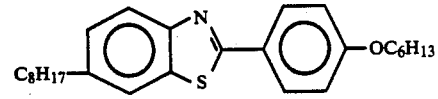 (I-177)
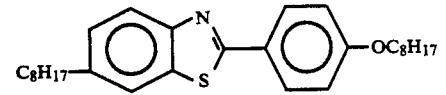 (I-178)
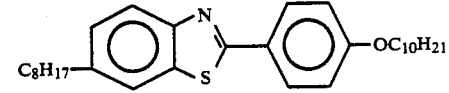 (I-179)
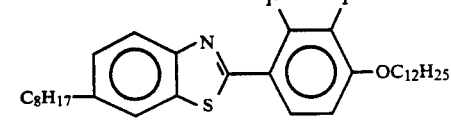 (I-180)
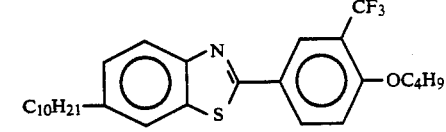 (I-181)
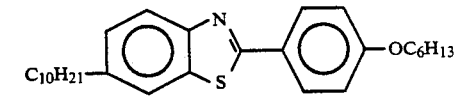 (I-182)
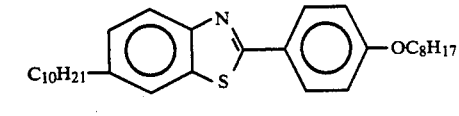 (I-183)
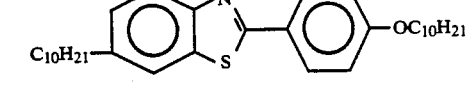 (I-184)
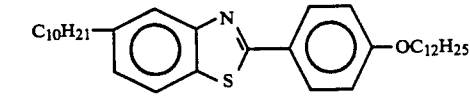 (I-185)
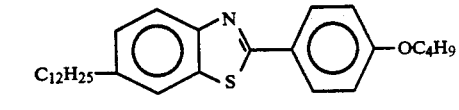 (I-186)
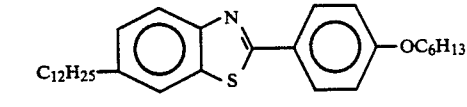 (I-187)

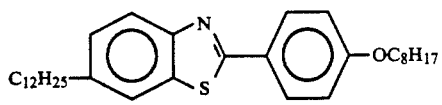 (I-188)
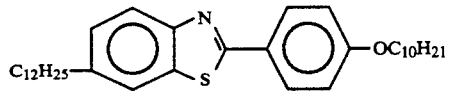 (I-189)
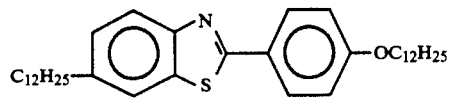 (I-190)
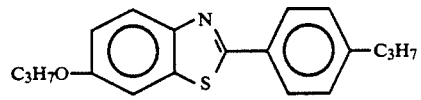 (I-191)
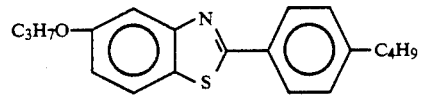 (I-192)
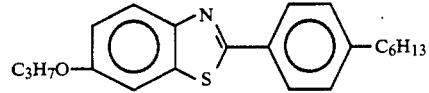 (I-193)
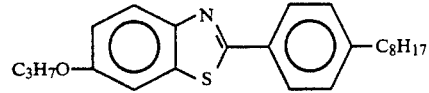 (I-194)
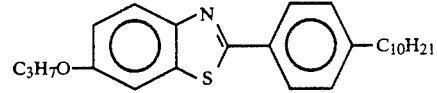 (I-195)
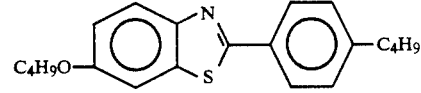 (I-196)
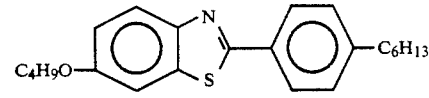 (I-197)
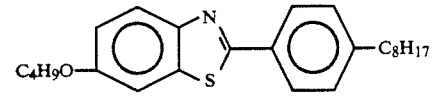 (I-198)
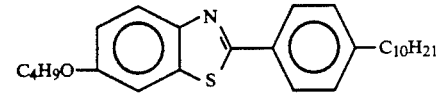 (I-199)
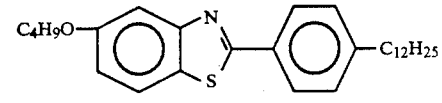 (I-200)
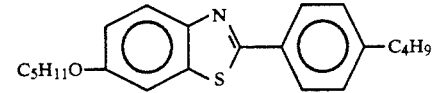 (I-201)

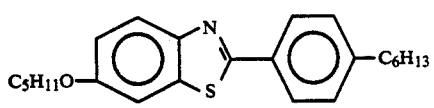 (I-202)
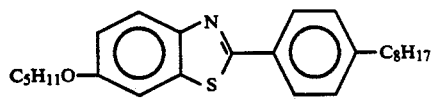 (I-203)
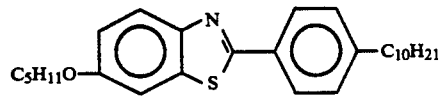 (I-204)
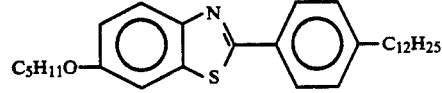 (I-205)
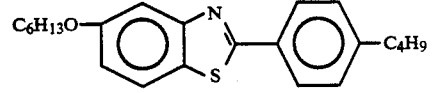 (I-206)
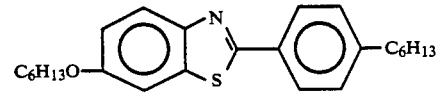 (I-207)
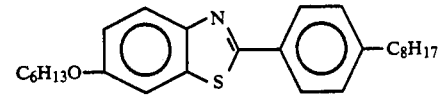 (I-208)
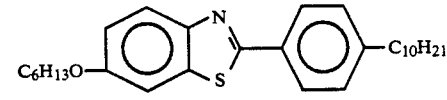 (I-209)
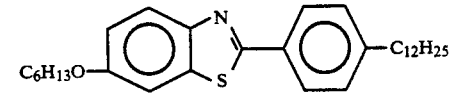 (I-210)
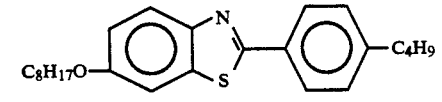 (I-211)
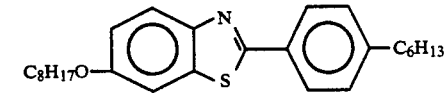 (I-212)
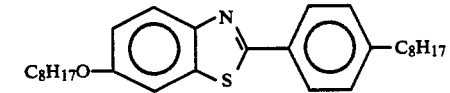 (I-213)
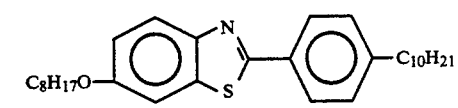 (I-214)

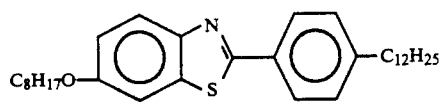 (I-215)
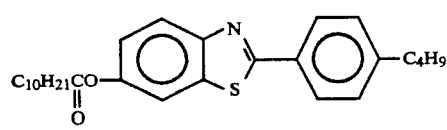 (I-216)
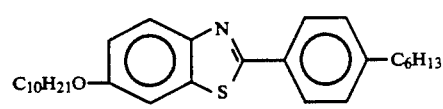 (I-217)
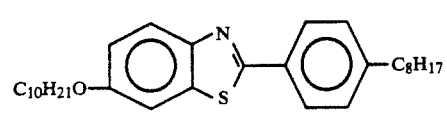 (I-218)
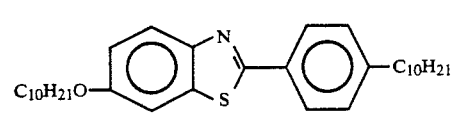 (I-219)
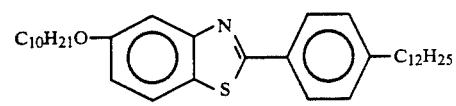 (I-220)
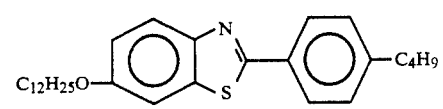 (I-221)
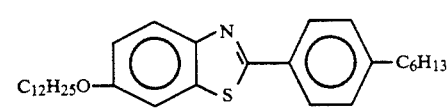 (I-222)
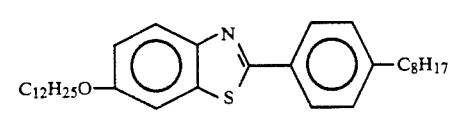 (I-223)
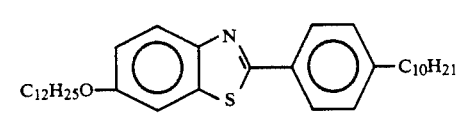 (I-224)
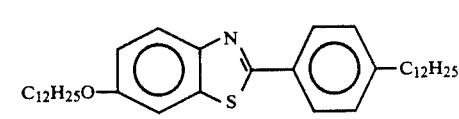 (I-225)
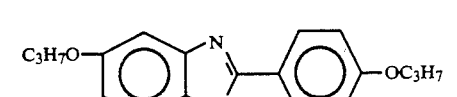 (I-226)
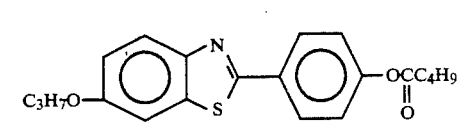 (I-227)

-continued
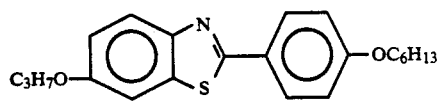 (I-228)
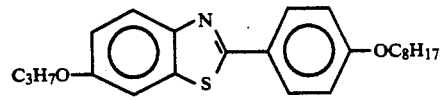 (I-229)
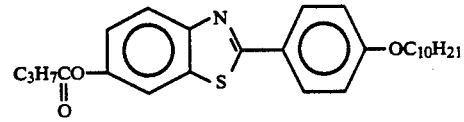 (I-230)
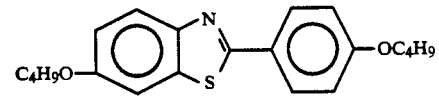 (I-231)
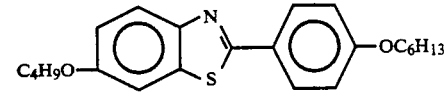 (I-232)
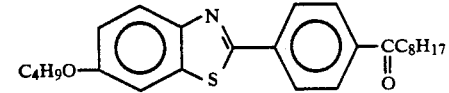 (I-233)
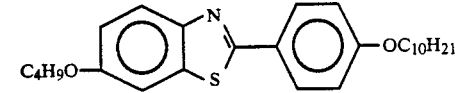 (I-234)
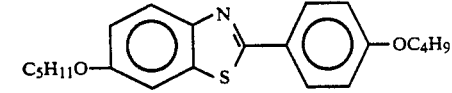 (I-235)
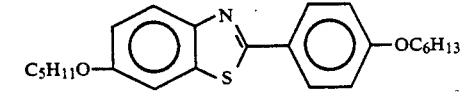 (I-236)
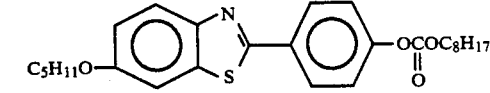 (I-237)
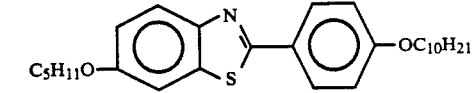 (I-238)
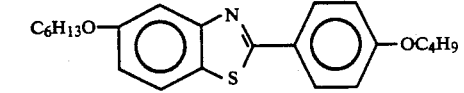 (I-239)
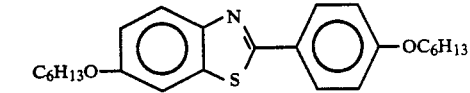 (I-240)

-continued
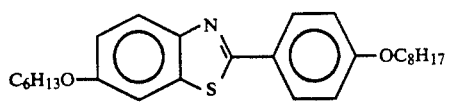 (I-241)
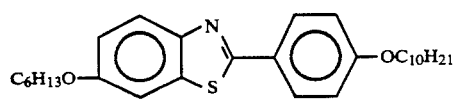 (I-242)
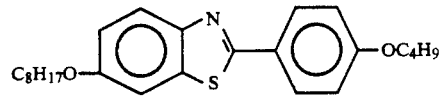 (I-243)
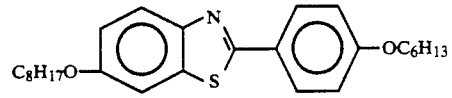 (I-244)
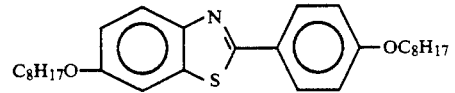 (I-245)
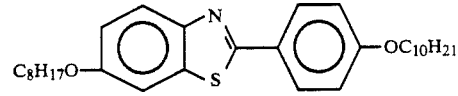 (I-246)
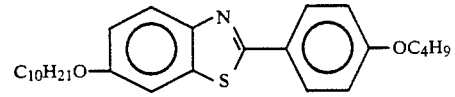 (I-247)
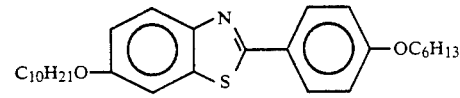 (I-248)
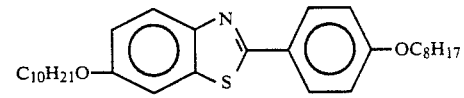 (I-249)
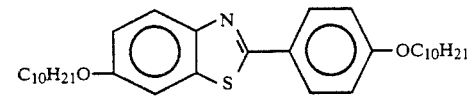 (I-250)
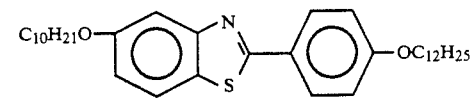 (I-251)
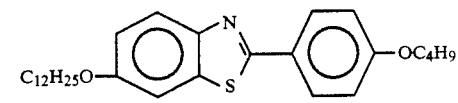 (I-252)
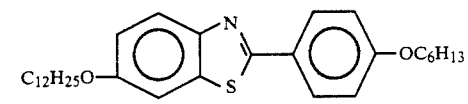 (I-253)

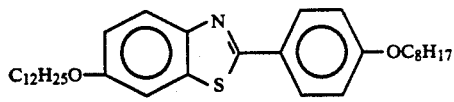
(I-254)
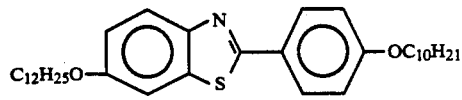
(I-255)
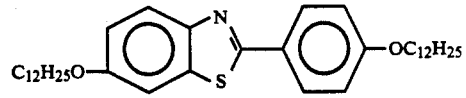
(I-256)
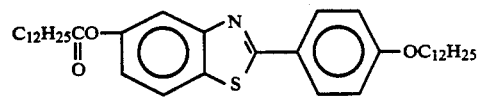
(I-257)
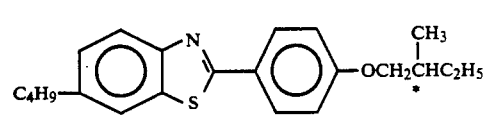
(I-258)
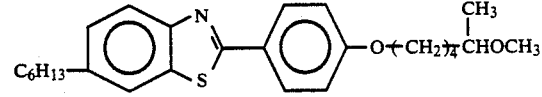
(I-259)
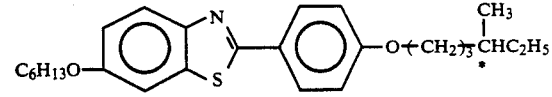
(I-260)
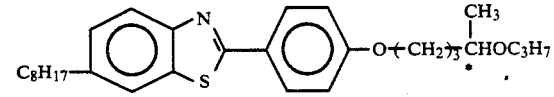
(I-261)
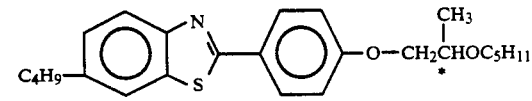
(I-262)
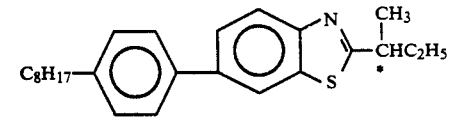
(I-263)
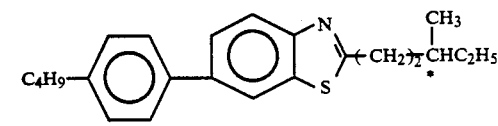
(I-264)
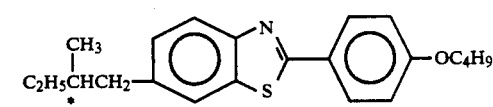
(I-265)
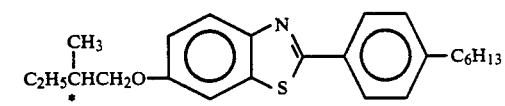
(I-266)

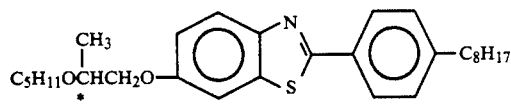 (I-267)
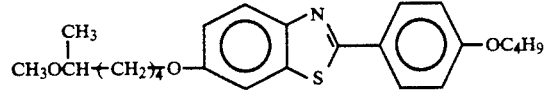 (I-268)
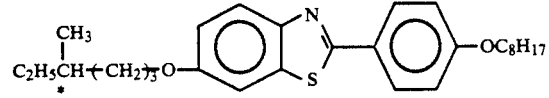 (I-269)
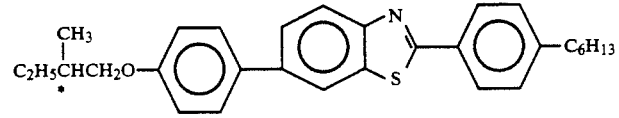 (I-270)
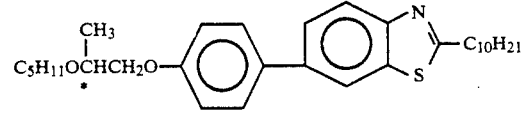 (I-271)
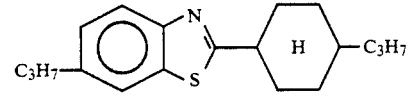 (I-272)
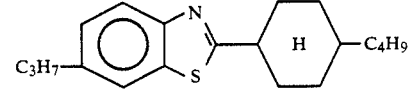 (I-273)
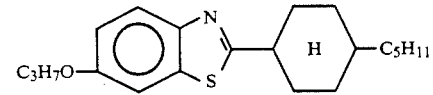 (I-274)
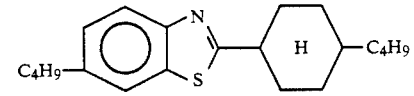 (I-275)
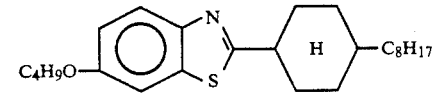 (I-276)
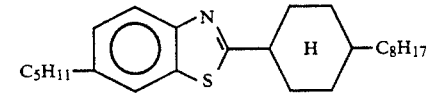 (I-277)
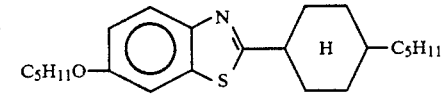 (I-278)
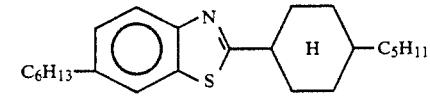 (I-279)

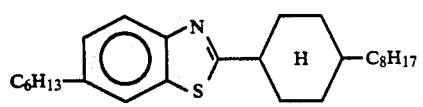 (I-280)
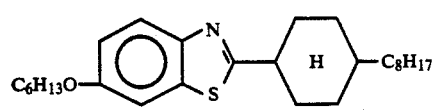 (I-281)
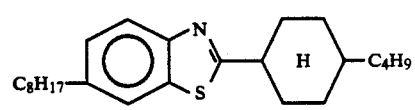 (I-282)
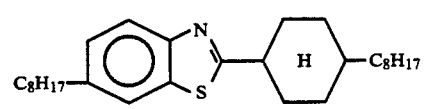 (I-283)
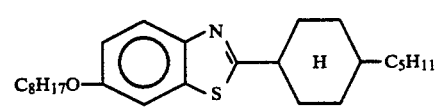 (I-284)
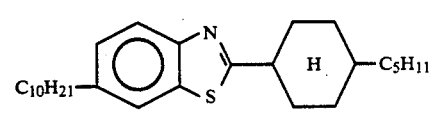 (I-285)
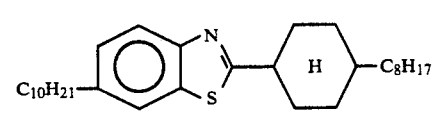 (I-286)
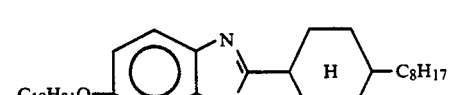 (I-287)
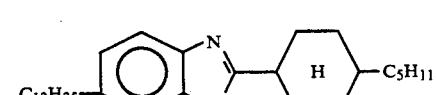 (I-288)
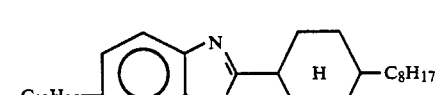 (I-289)
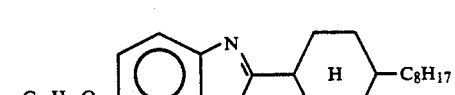 (I-290)
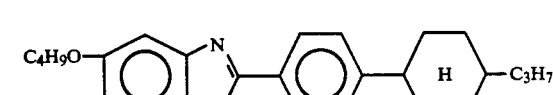 (I-291)
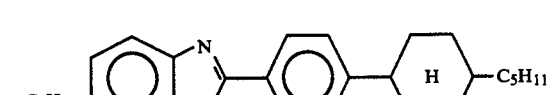 (I-292)
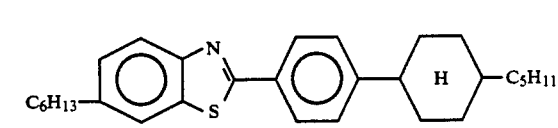 (I-293)

-continued
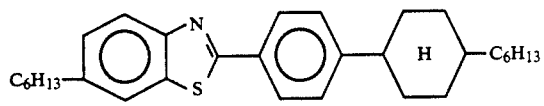 (I-294)
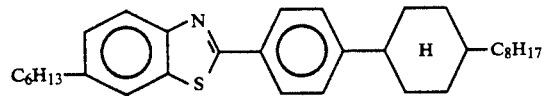 (I-295)
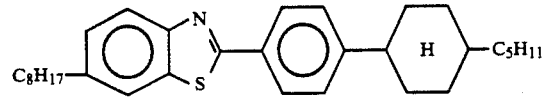 (I-296)
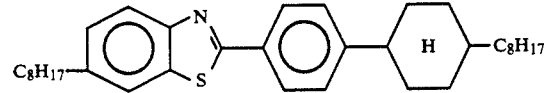 (I-297)
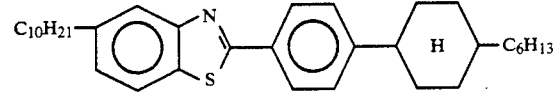 (I-298)
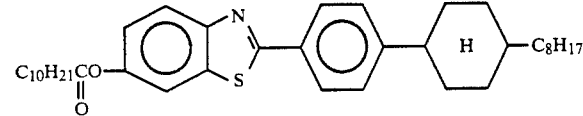 (I-299)
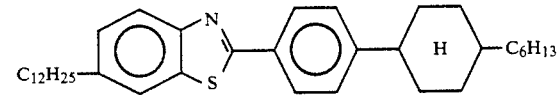 (I-300)
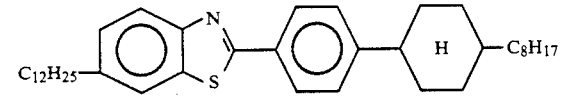 (I-301)
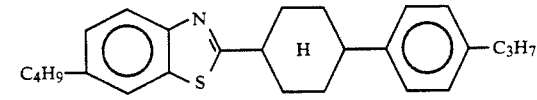 (I-302)
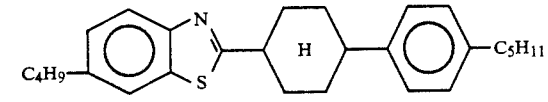 (I-303)
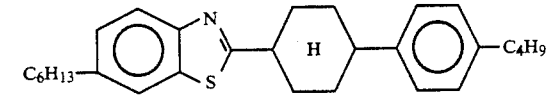 (I-304)
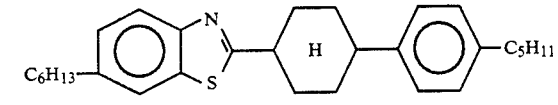 (I-305)
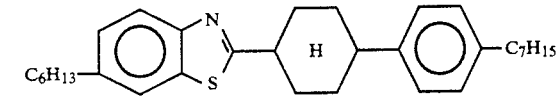 (I-306)

-continued
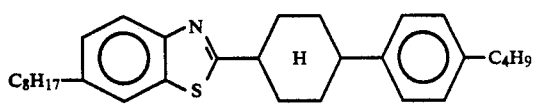 (I-307)
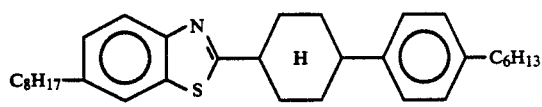 (I-308)
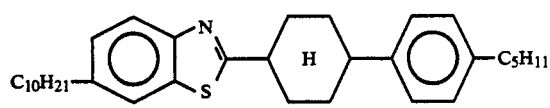 (I-309)
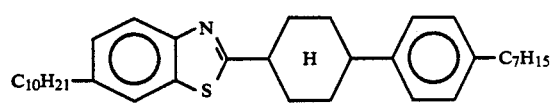 (I-310)
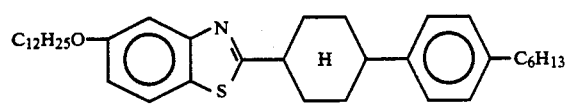 (I-311)
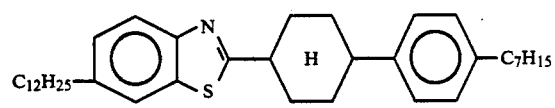 (I-312)
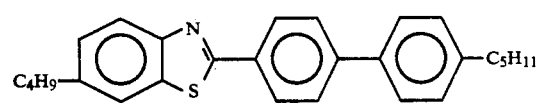 (I-313)
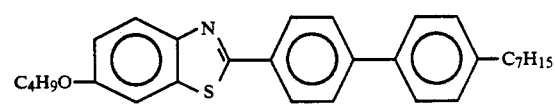 (I-314)
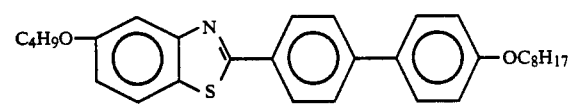 (I-315)
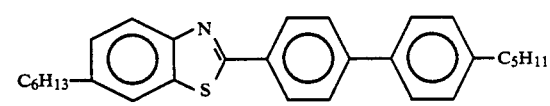 (I-316)
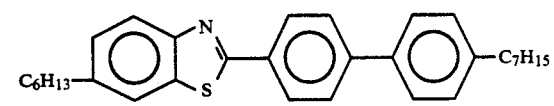 (I-317)
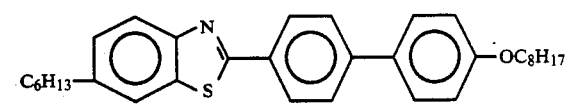 (I-318)
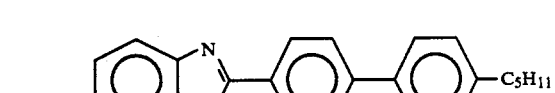 (I-319)
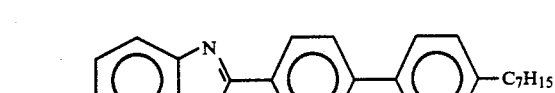 (I-320)

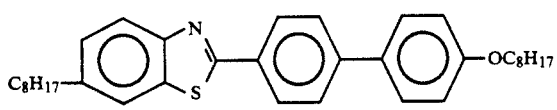 (I-321)
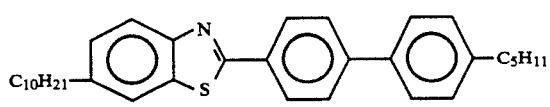 (I-322)
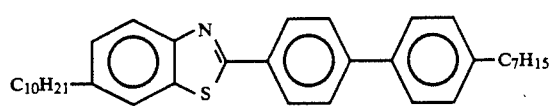 (I-323)
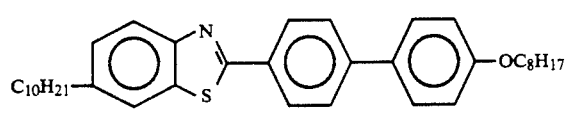 (I-324)
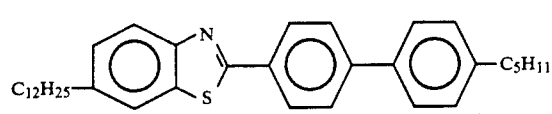 (I-325)
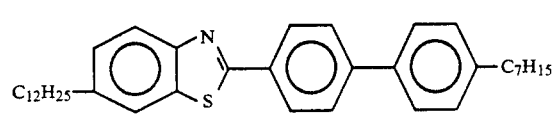 (I-326)
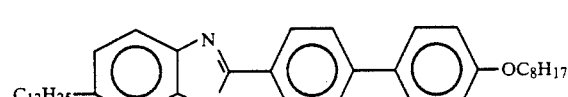 (I-327)
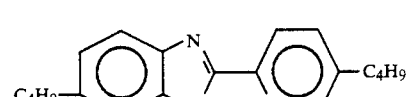 (I-328)
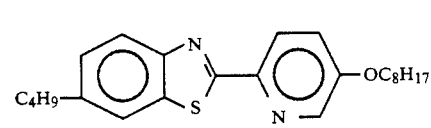 (I-329)
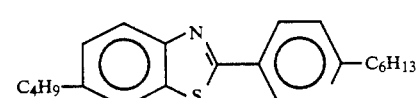 (I-330)
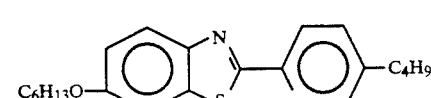 (I-331)
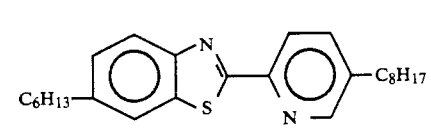 (I-332)
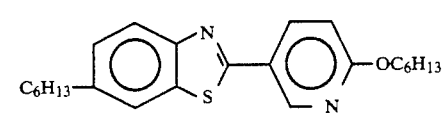 (I-333)

-continued
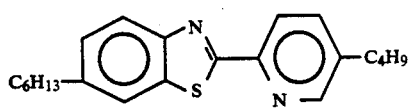 (I-334)
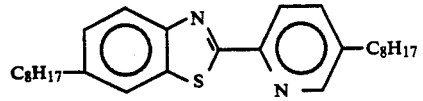 (I-335)
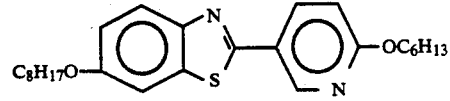 (I-336)
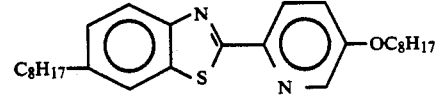 (I-337)
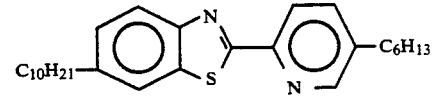 (I-338)
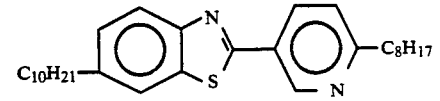 (I-339)
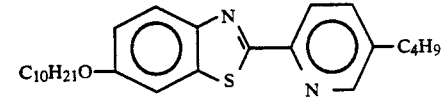 (I-340)
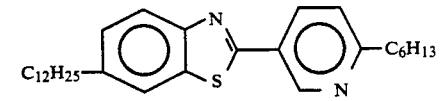 (I-341)
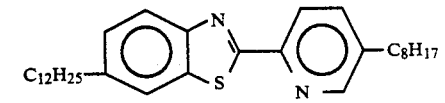 (I-342)
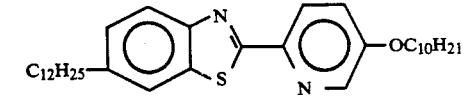 (I-343)
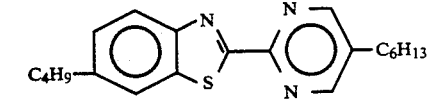 (I-344)
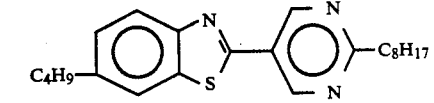 (I-345)
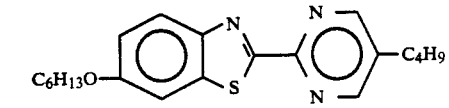 (I-346)

-continued
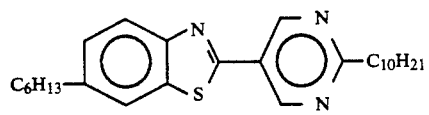 (I-347)
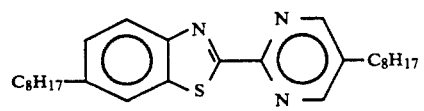 (I-348)
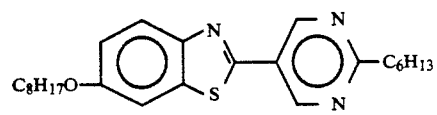 (I-349)
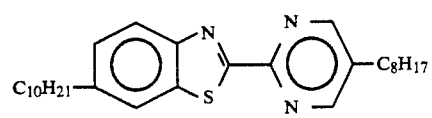 (I-350)
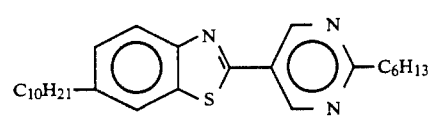 (I-351)
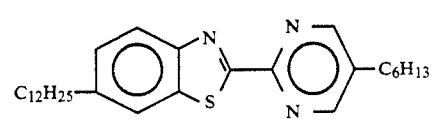 (I-352)
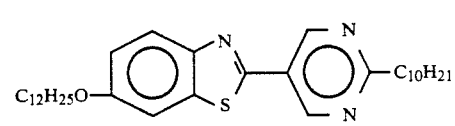 (I-353)
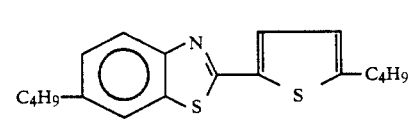 (I-354)
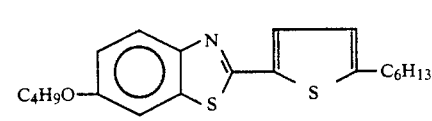 (I-355)
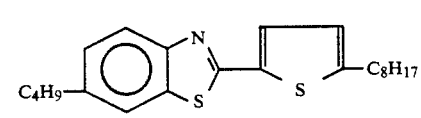 (I-356)
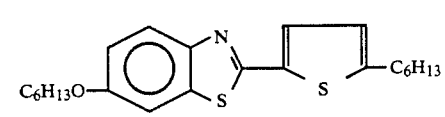 (I-357)
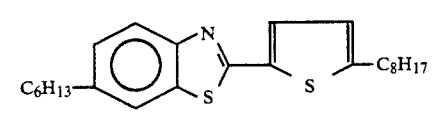 (I-358)
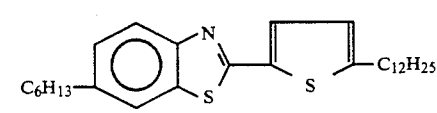 (I-359)

-continued (I-360)
(I-361)
(I-362)
(I-363)
(I-364)
(I-365)
(I-366)
(I-367)
(I-368)
(I-369)
(I-370)
(I-371)
(I-372)

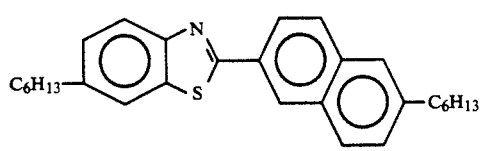
(I-373)
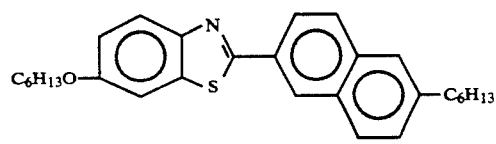
(I-374)
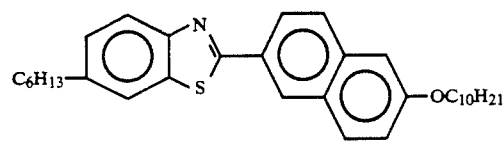
(I-375)
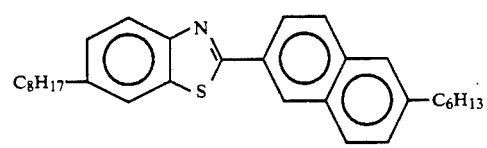
(I-376)
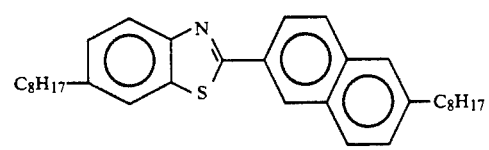
(I-377)
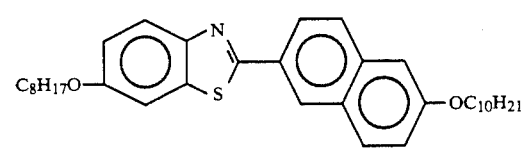
(I-378)
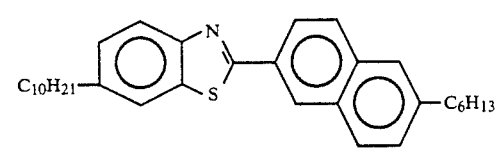
(I-379)
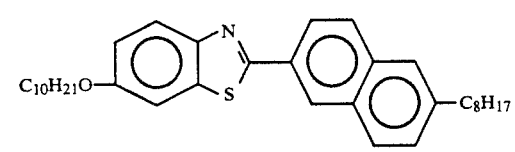
(I-380)
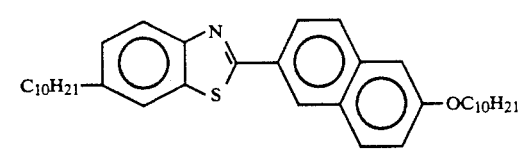
(I-381)
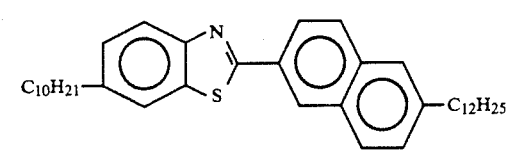
(I-382)

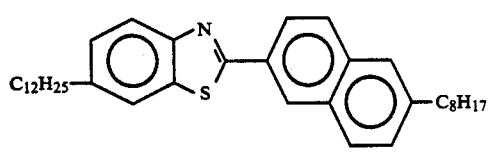
(I-383)
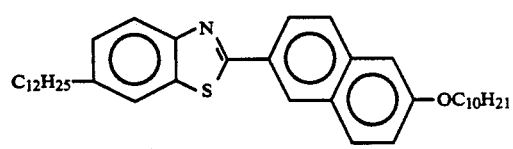
(I-384)
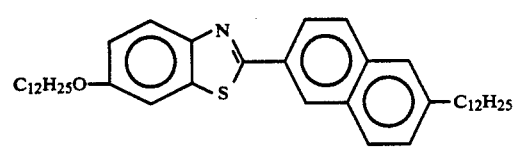
(I-385)
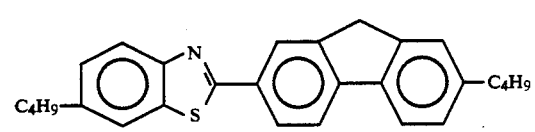
(I-386)
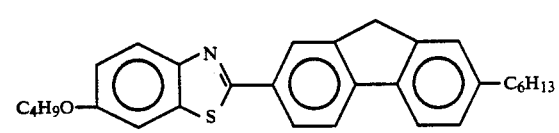
(I-387)
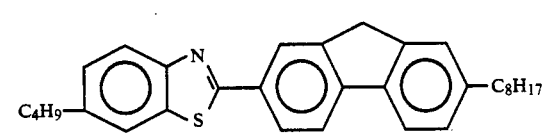
(I-388)
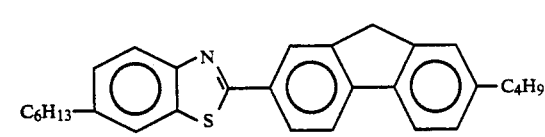
(I-389)
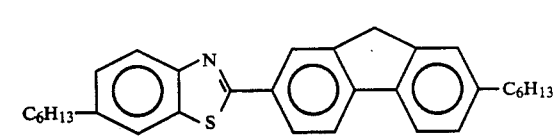
(I-390)
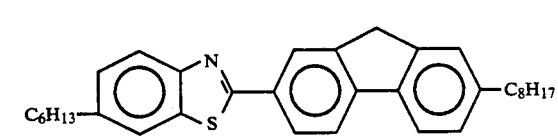
(I-391)
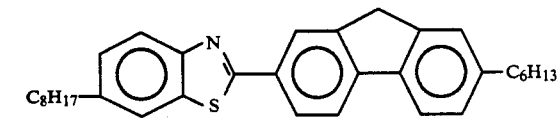
(I-392)
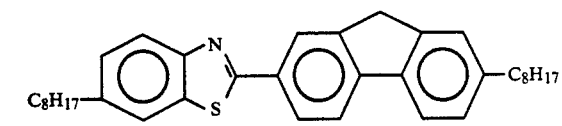
(I-393)

-continued
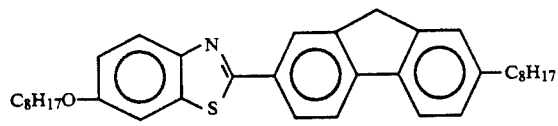
(I-394)
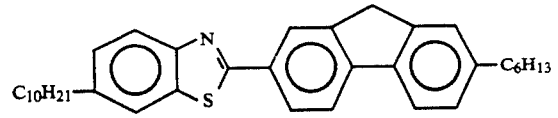
(I-395)
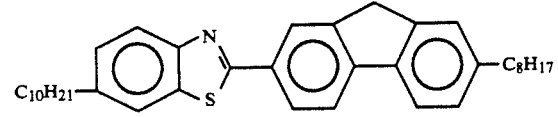
(I-396)
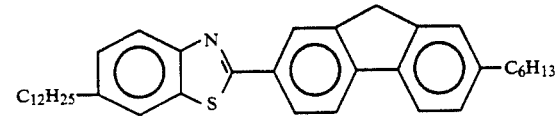
(I-397)
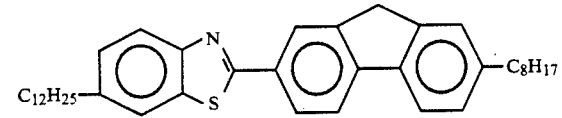
(I-398)
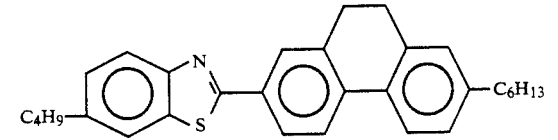
(I-399)
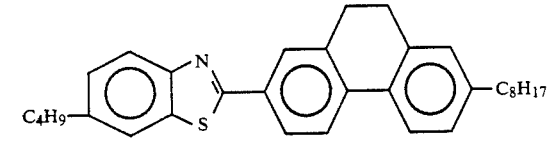
(I-400)
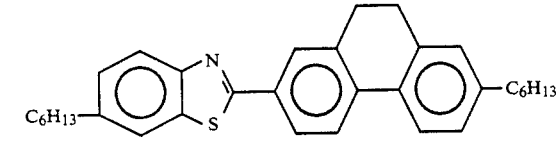
(I-401)
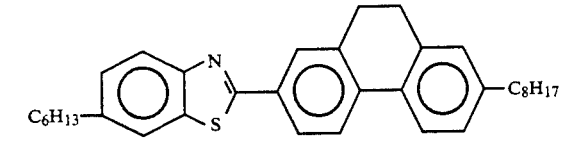
(I-402)
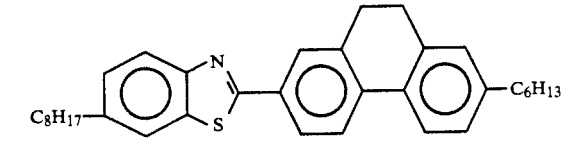
(I-403)
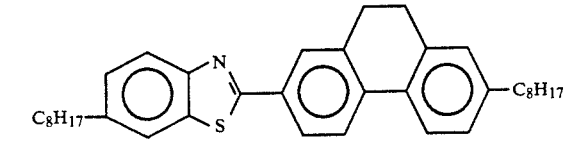
(I-404)

-continued
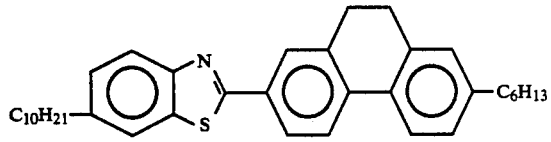
(I-405)
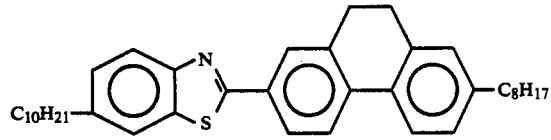
(I-406)
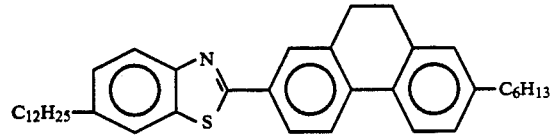
(I-407)
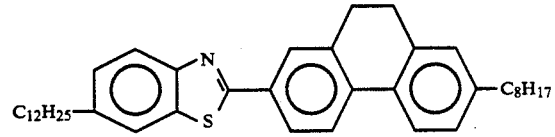
(I-408)
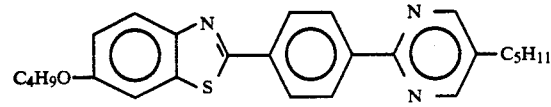
(I-409)
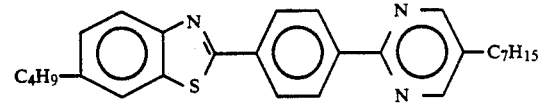
(I-410)
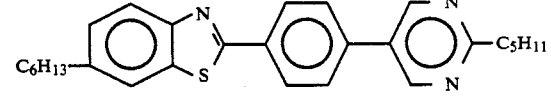
(I-411)
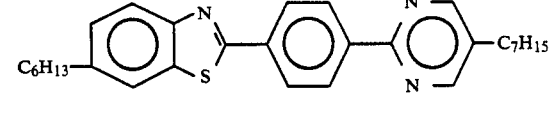
(I-412)
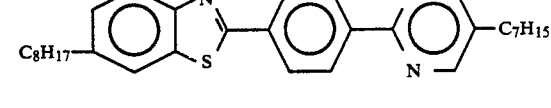
(I-413)
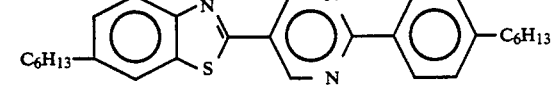
(I-414)
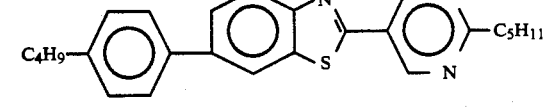
(I-415)
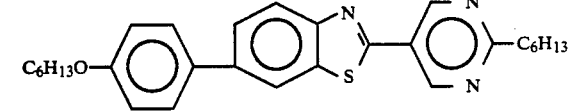
(I-416)

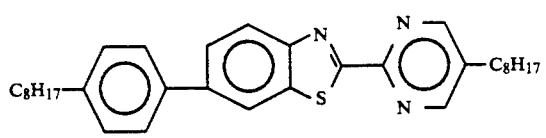 (I-417)
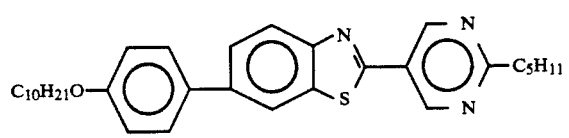 (I-418)
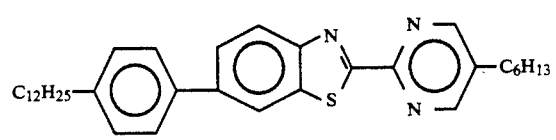 (I-419)
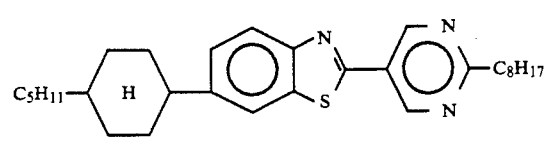 (I-420)
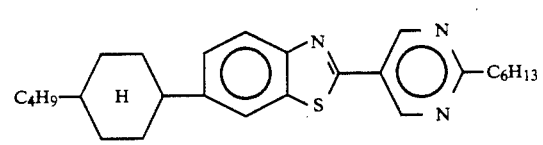 (I-421)
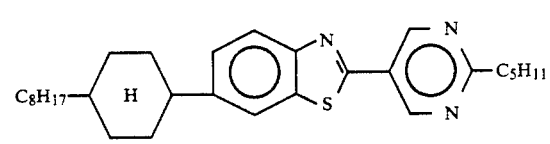 (I-422)
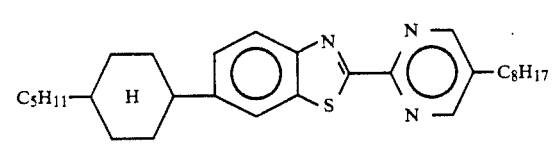 (I-423)
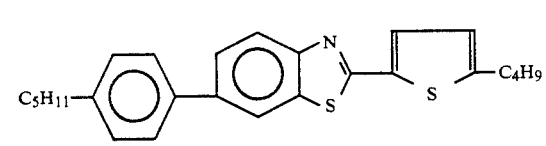 (I-424)
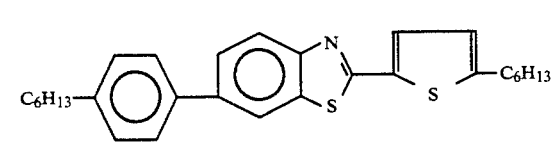 (I-425)
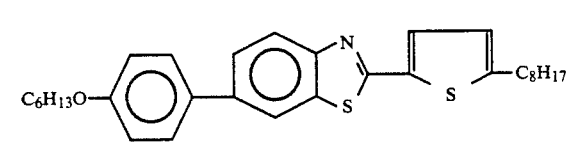 (I-426)
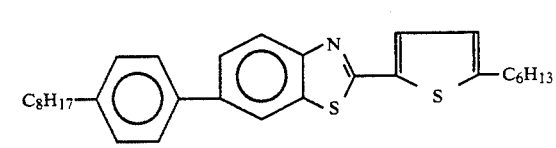 (I-427)

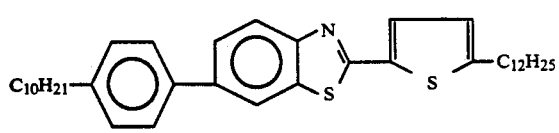 (I-428)
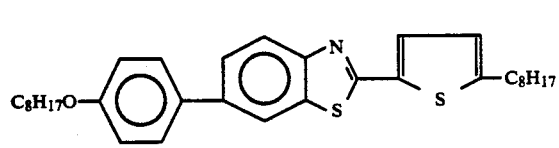 (I-429)
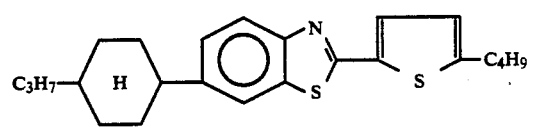 (I-430)
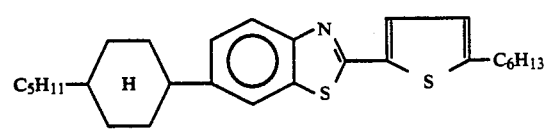 (I-431)
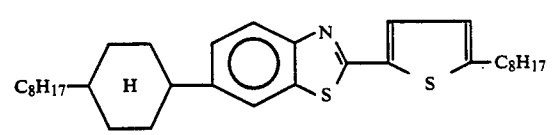 (I-432)
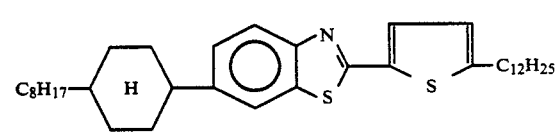 (I-433)
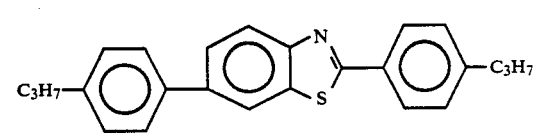 (I-434)
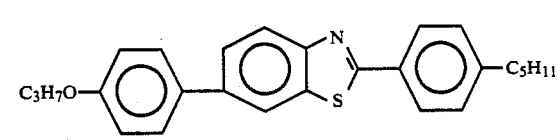 (I-435)
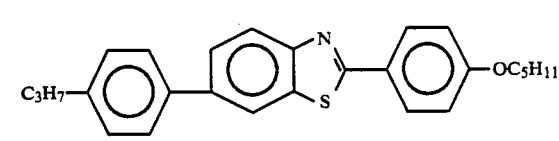 (I-436)
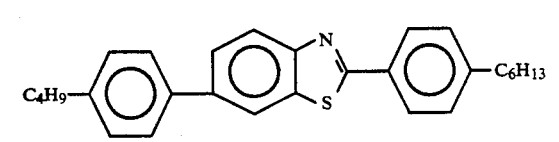 (I-437)
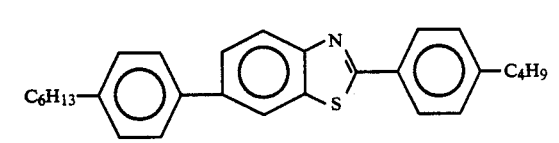 (I-438)
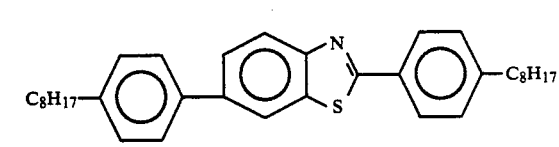 (I-439)

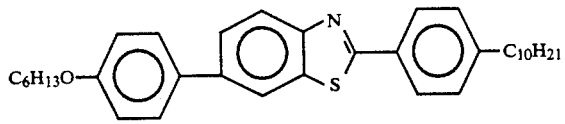
(I-440)
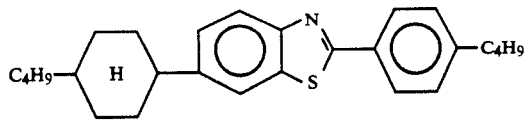
(I-441)
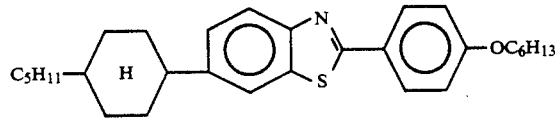
(I-442)
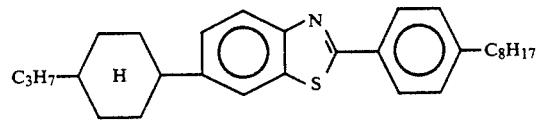
(I-443)
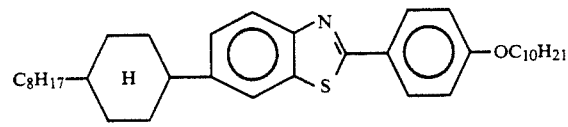
(I-444)
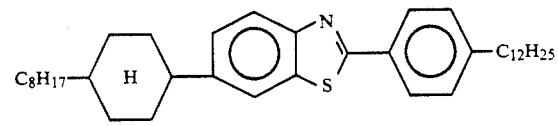
(I-445)
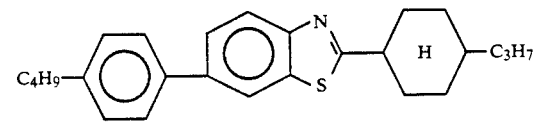
(I-446)
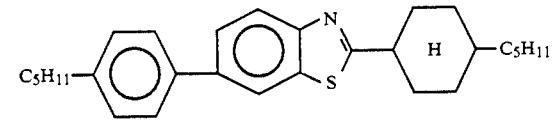
(I-447)
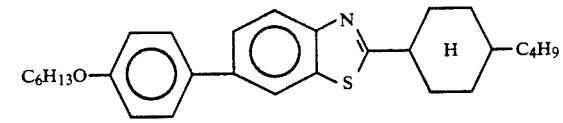
(I-448)
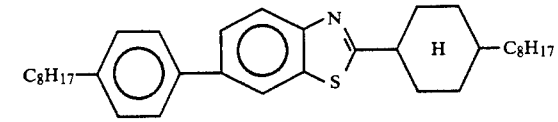
(I-449)
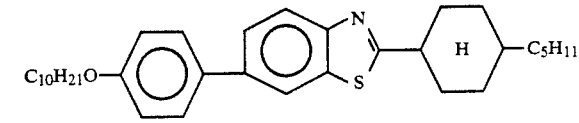
(I-450)

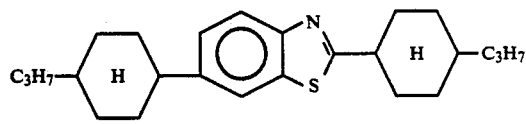
(I-451)
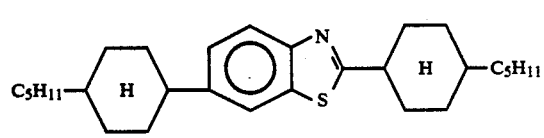
(I-452)
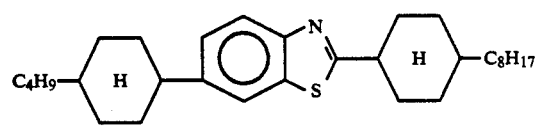
(I-453)
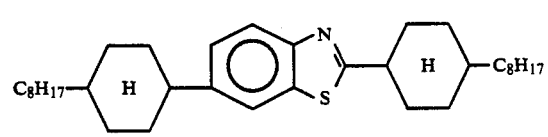
(I-454)
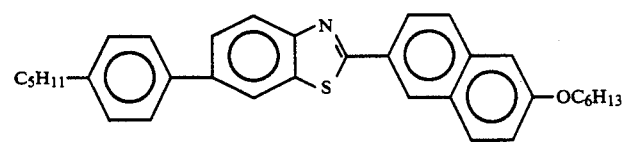
(I-455)
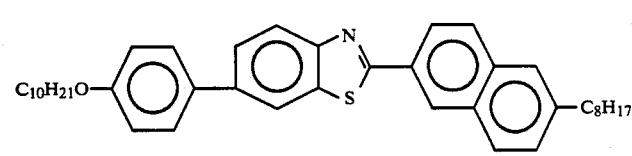
(I-456)
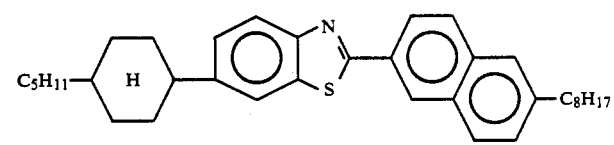
(I-457)
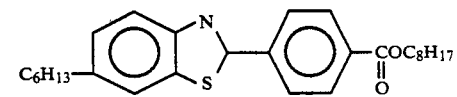
(I-458)
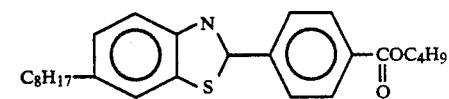
(I-459)
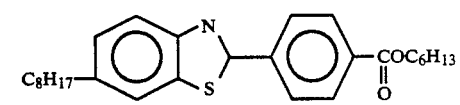
(I-460)
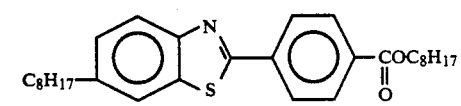
(I-461)
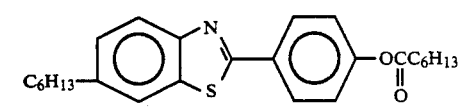
(I-462)

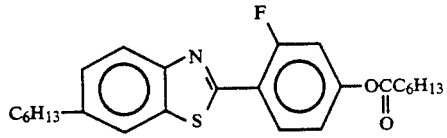
(I-463)
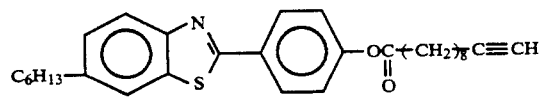
(I-464)
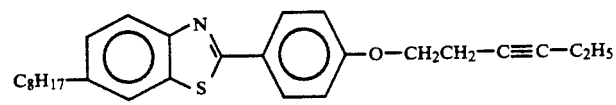
(I-465)
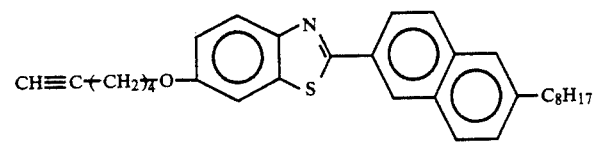
(I-466)
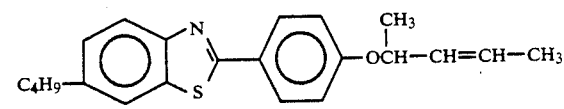
(I-467)
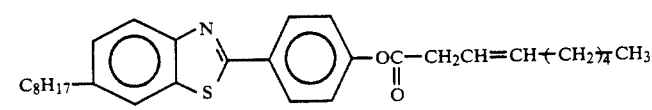
(I-468)
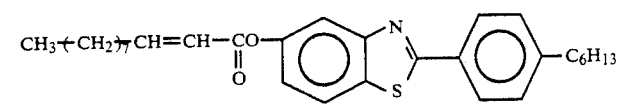
(I-469)
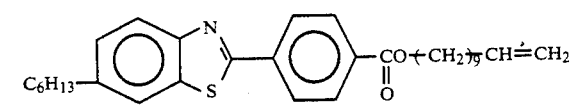
(I-470)
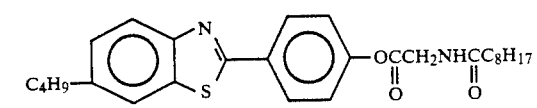
(I-471)
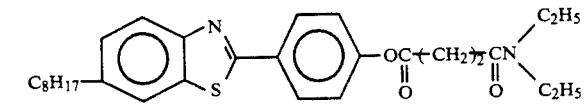
(I-472)
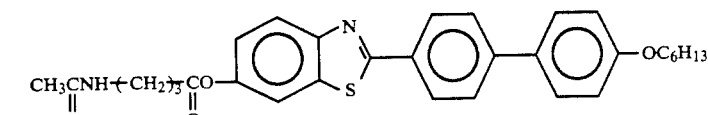
(I-473)
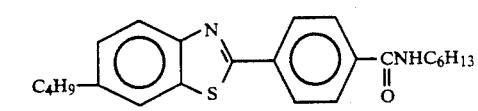
(I-474)
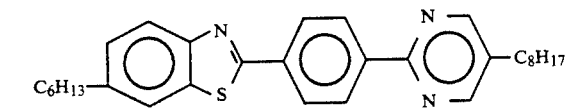
(I-475)

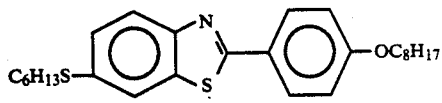 (I-476)
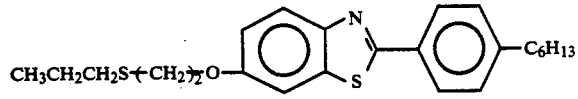 (I-477)
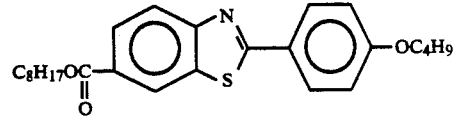 (I-478)
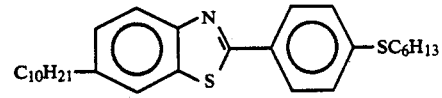 (I-479)
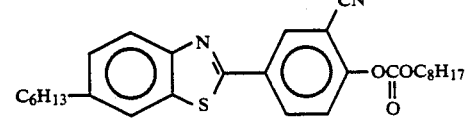 (I-480)
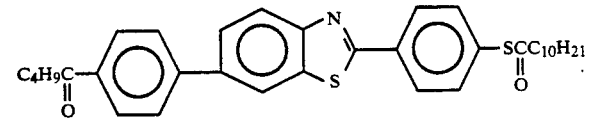 (I-481)
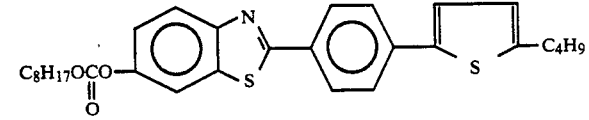 (I-482)
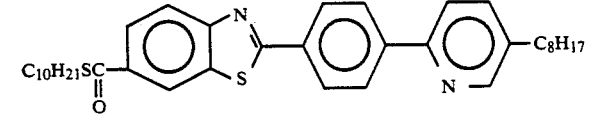 (I-483)
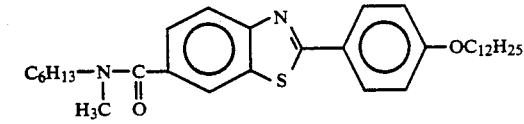 (I-484)
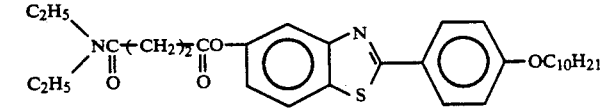 (I-485)
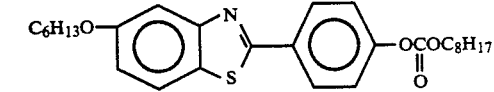 (I-486)
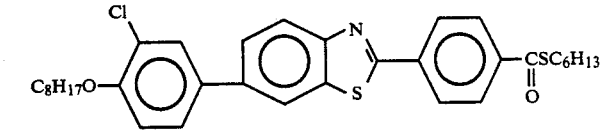 (I-487)

-continued

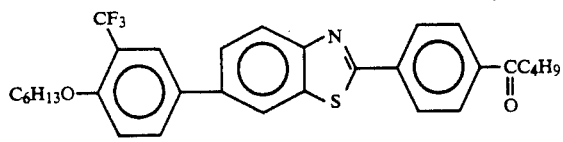
(I-488)

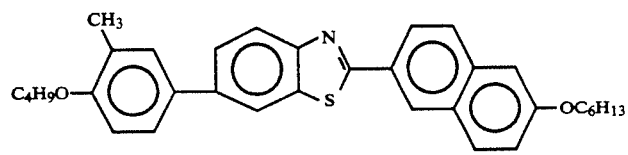
(I-489)

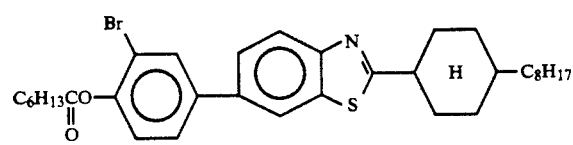
(I-490)

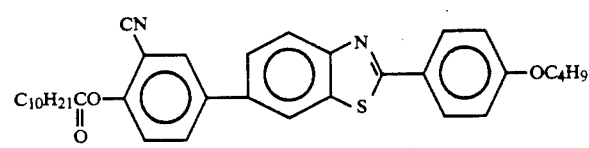
(I-491)

The liquid crystal composition according to the present invention may be obtained by mixing at least one species of the compound represented by the formula (I) and another mesomorphic compound in appropriate proportions. The liquid crystal composition according to the present invention may preferably be formulated as a liquid crystal composition capable of utilizing ferroelectricity, particularly a liquid crystal composition showing a chiral smectic phase.

Specific examples of another mesomorphic compound as described above may include those denoted by the following formulas (III) to (XI).

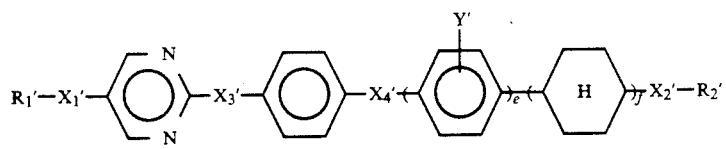
(III)

wherein e denotes 0 or 1 and f denotes 0 or 1 with proviso that e+f=0 or 1; Y' denotes H, halogen, $CH_3$ or $CF_3$; $X_1'$ and $X_2'$ respectively denote a single bond,

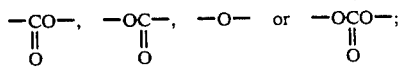

and $X_3'$ and $X_4'$ respectively denote a single bond,

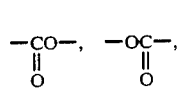

—$OCH_2$ or —$CH_2O$—.

In the formula (III), preferred compounds thereof may include those represented by the following formulas (IIIa) to (IIId):

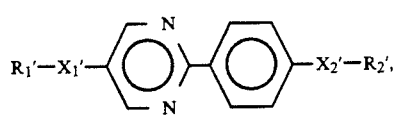
(IIIa)

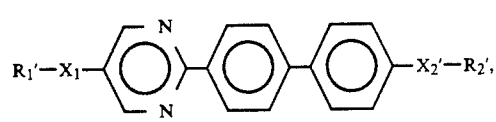
(IIIb)

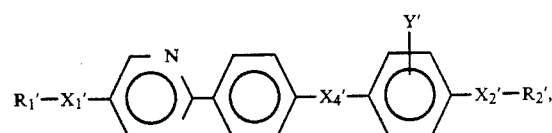
(IIIc)

and

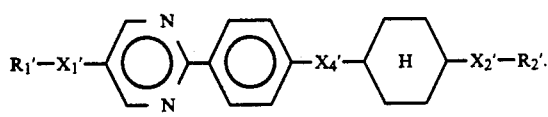  (IIId)

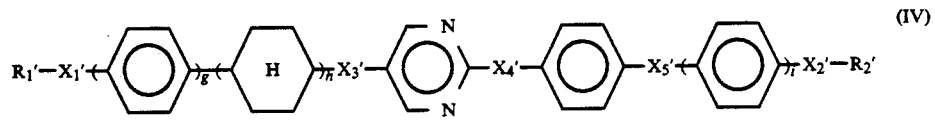  (IV)

wherein g and h respectively denote 0 or 1 with proviso that g+h=1; i denotes 0 or 1; $X_1'$ and $X_2'$ repectively denote a single bond,

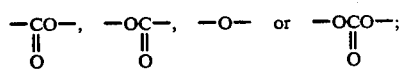

and $X_3'$, $X_4'$ and $X_5'$ respectively denote a single bond,

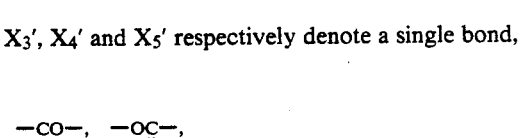

—CH$_2$O— or —OCH$_2$—.

In the formula (IV), preferred compounds thereof may include those represented by the following formulas (IVa) to (IVc):

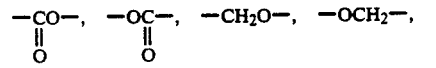

and $X_3'$ and $X_4'$ respectively denote a single bond,

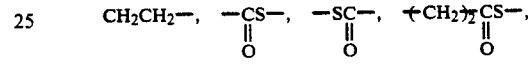

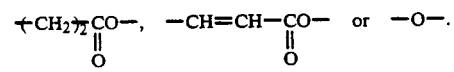

In the formula (V), preferred compounds thereof may

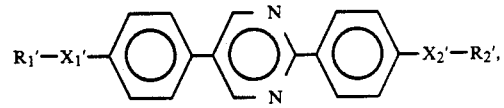  (IVa)

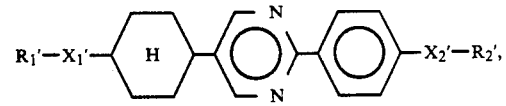  (IVb)

and

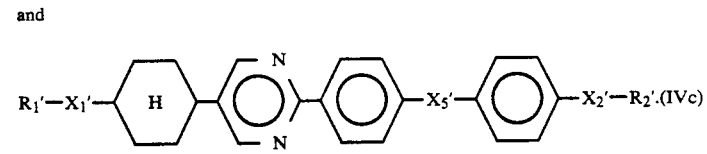

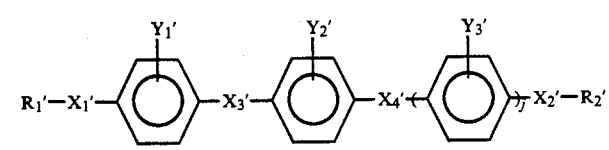  (V)

wherein j denotes 0 or 1; $Y_1'$, $Y_2'$ and $Y_3'$ respectively denote H, halogen, CH$_3$ or CF$_3$; $X_1'$ and $X_2'$ respectively denote a single bond, include those represented by the following formulas (Va) and (Vb);

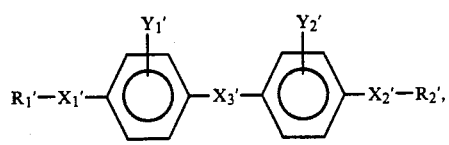  (Va)

and

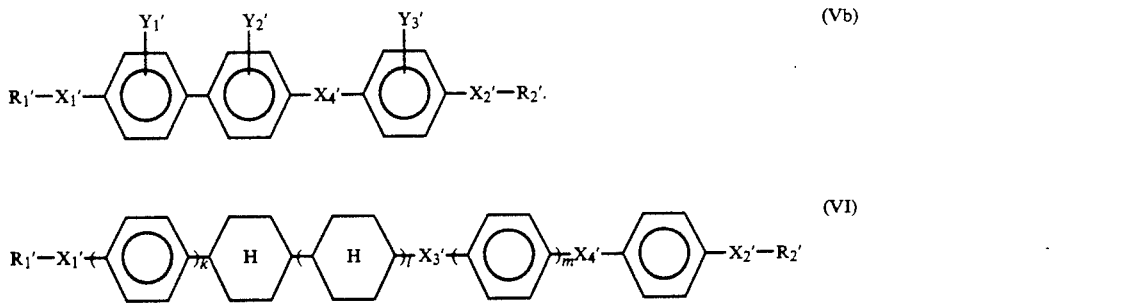

(Vb)

(VI)

wherein k, l and m respectively denote 0 or 1 with proviso that k+l+m=0, 1 or 2; X$_1'$ and X$_2'$ respectively denote a single bond,

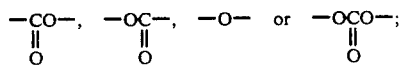

and X$_3'$ and X$_4'$ respectively denote a single bond,

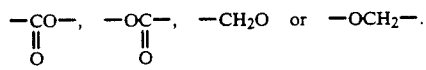

In the formula (VI), preferred compounds thereof may include those represented by the following formulas (VIa) to (VIf):

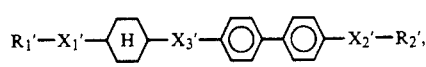  (VIa)

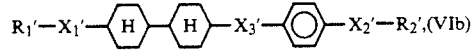  (VIb)

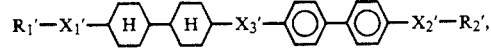  (VIc)

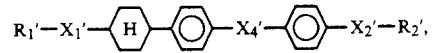  (VId)

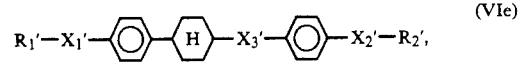  (VIe)

and

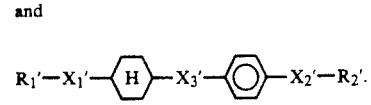  (VIf)

Herein, R$_1'$ and R$_2'$ respectively denote a linear or branched alkyl group having 1-18 carbon atoms capable of including one or two or more non-neighboring methylene groups which can be replaced with —CH halogen- and capable of further including one or two or more non-neighboring methylene groups other than those directly connected to X$_1'$ or X$_2'$ which can be replaced with at least one species of

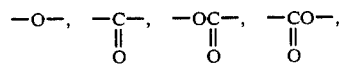

-continued

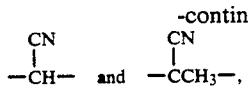

with proviso that R$_1'$ and R$_2'$ respectively do not connect to a ring structure when R$_1'$ and R$_2'$ respectively denote a halogenated alkyl group containing one methylene group replaced with —CH halogen-.

Further, preferred examples of R$_1'$ and R$_2'$ may respectively include those represented by the following groups (i) to (vii):

i) a linear alkyl group having 1-15 carbon atoms;

ii) 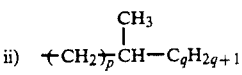

wherein p denotes an integer of 0-5 and g denotes an integer of 1-11 (optically active or inactive);

iii) 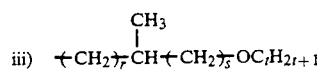

wherein r denotes an integer of 0-6, s denotes 0 or 1, and t denotes an integer of 1-14 (optically active or inactive);

iv) 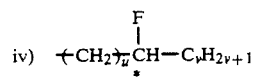

wherein u denotes 0 or 1 and v denotes an integer of 1-16;

v) 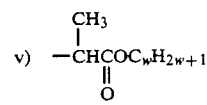

wherein w denotes an integer of 1-15 (optically active or inactive);

vi) 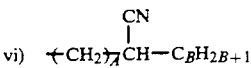

wherein A denotes an integer of 0-2 and B denotes an integer of 1-15 (optically active or inactive); and vii) 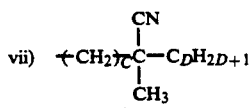

wherein C denotes an integer of 0–2 and D denotes an integer of 1–15 (optically active or inactive).

In the above-mentioned formula (III), more preferred compounds thereof may include those represented by the formulas (IIIaa) to (IIIdc):

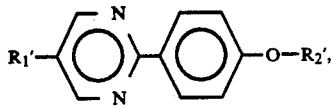 (IIIaa)

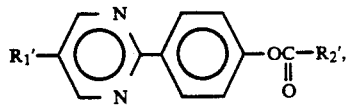 (IIIab)

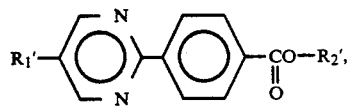 (IIIac)

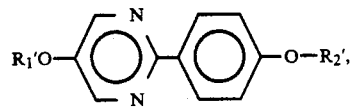 (IIIad)

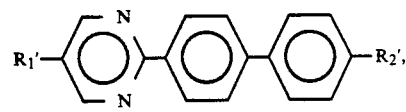 (IIIba)

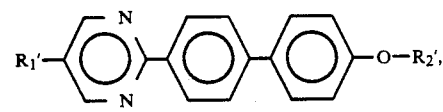 (IIIbb)

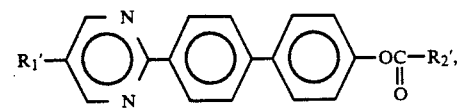 (IIIbc)

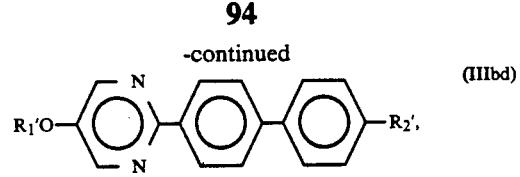 (IIIbd)

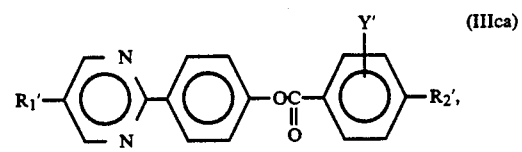 (IIIca)

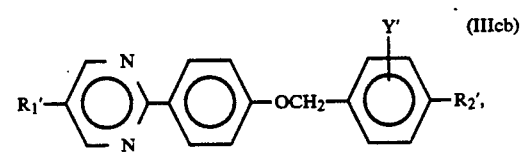 (IIIcb)

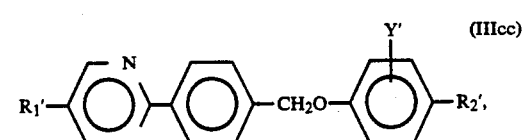 (IIIcc)

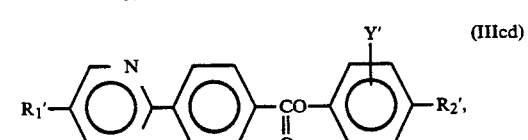 (IIIcd)

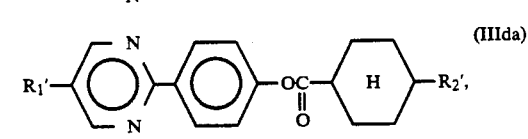 (IIIda)

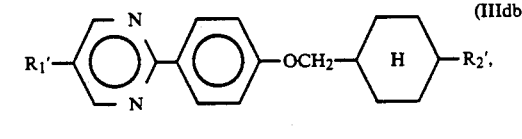 (IIIdb)

and

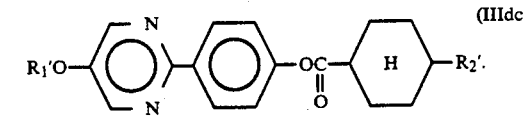 (IIIdc)

In the above-mentioned formula (IV), more preferred compounds thereof may include those represented by the formulas (IVaa) to (IVcd):

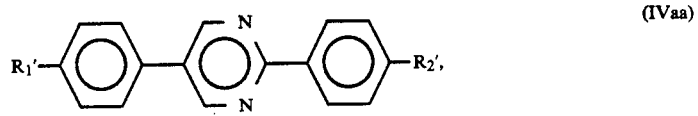 (IVaa)

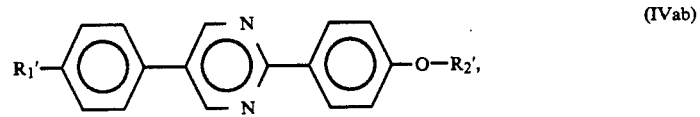 (IVab)

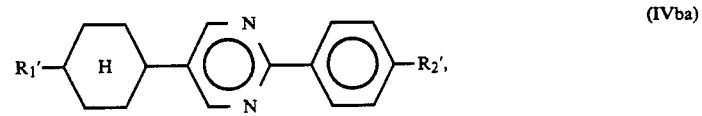 (IVba)

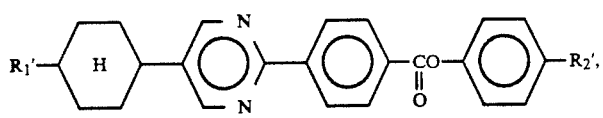
(IVca)
and
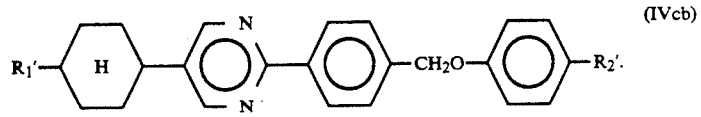
(IVcb)
In the above-mentioned formula (V), more preferred compounds thereof may include those represented by the formulas (Vaa) to (Vbf):
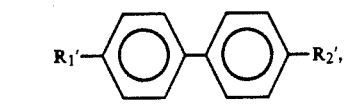
(Vaa)
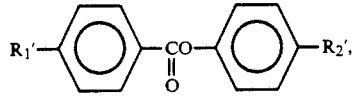
(Vab)
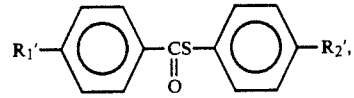
(Vac)
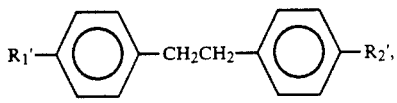
(Vad)
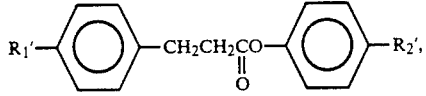
(Vae)
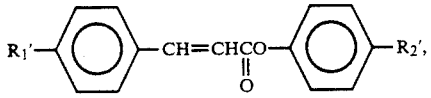
(Vaf)
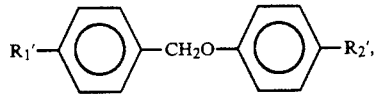
(Vag)
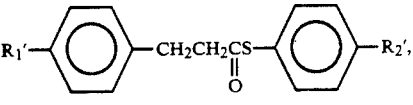
(Vah)
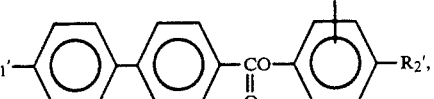
(Vba)
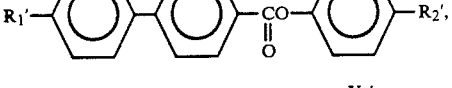
(Vbb)
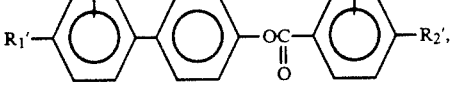
(Vbc)
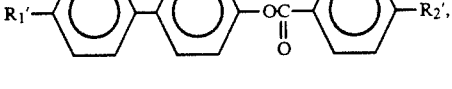
(Vbd)
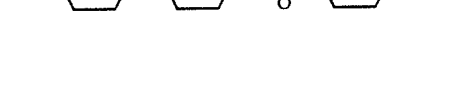
(Vbe)
and
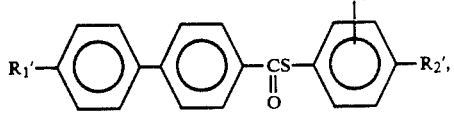
(Vbf)
In the above-mentioned formula (VI), more preferred compounds thereof may include those represented by the formulas (VIaa) to (VIfa):
(VIaa)
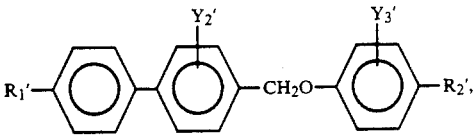
(VIab)
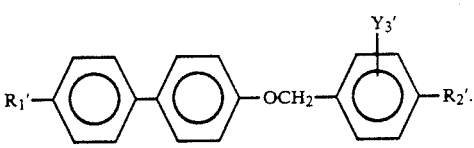
(VIba)
(VIbb)
(VIda)

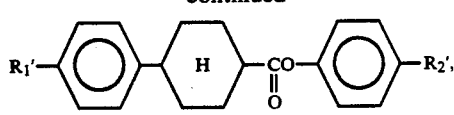 (VIea)

and

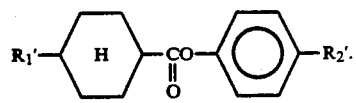 (VIfa)

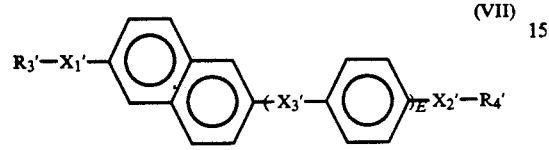 (VII)

wherein E denotes 0 or 1; $X_1'$ and $X_2'$ respectively denote a single bond,

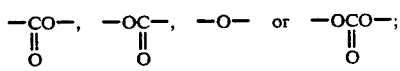

and $X_3'$ denotes a single bond,

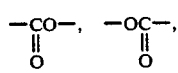

—CH₂O— or —OCH₂—.

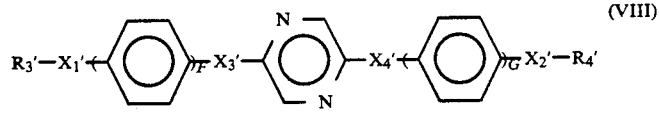 (VIII)

wherein F and G respectively denote 0 or 1; $X_1'$ and $X_2'$ respectively denote a single bond,

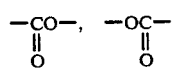

or —O—; and $X_3'$ and $X_4'$ respectively denote a single bond,

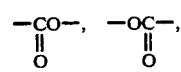

—CH₂O— or —OCH₂—.

In the above formula (VII), preferred compounds thereof may include those represented by the following formulas (VIIa) and (VIIb):

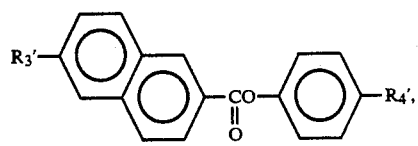 (VIIa)

and

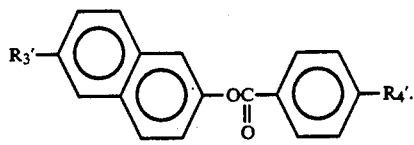 (VIIb)

In the above formula (VIII), preferred compounds thereof may include those represented by the follwoing formulas (VIIIa) and (VIIIb).

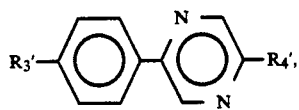 (VIIIa)

and

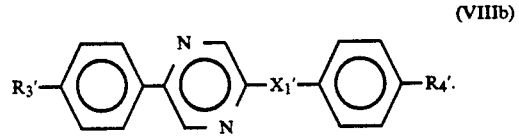 (VIIIb)

More preferred compounds of the formula (VIII) may include those represented by the formulas (VIIIaa) to (VIIIbb):

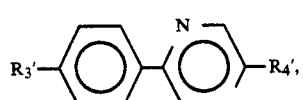 (VIIIaa)

 (VIIIba)

and

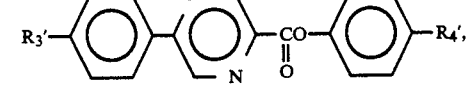 (VIIIbb)

Herein, $R_3'$ and $R_4'$ respectively denote a linear or branched alkyl group having 1-18 carbon atoms capable of including one or two or more non-neighboring methylene groups which can be replaced with —CH halogen- and capable of further including one or two or more non-neighboring methylene groups other than those directly connected to $X_1'$ or $X_2'$ which can be replaced with at least one species of —O—,

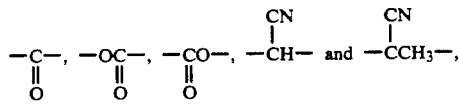

with proviso that $R_3'$ and $R_4'$ respectively do not connect to a ring structure when $R_3'$ and $R_4'$ respectively denote a halogenated alkyl group containing one methylene group replaced with —CH halogen-.

Further, preferred examples of $R_3'$ and $R_4'$ may respectively include those represented by the following groups (i) to (vii):

i) a linear alkyl group having 1-15 carbon atoms;

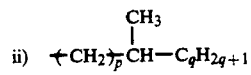

wherein p denotes an integer of 0-5 and q denotes an integer of 1-11 (optically active or in active);

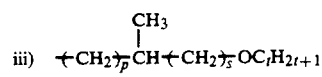

wherein r denotes an integer of 0-6, s denotes 0 or 1, and t denotes an integer of 1-14 (optically active or inactive);

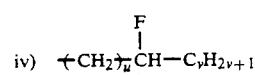

wherein u denotes an integer of 0-5 and v denotes an integer of 1-16;

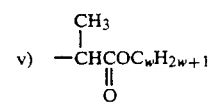

wherein w denotes an integer of 1-15 (optically active or inactive);

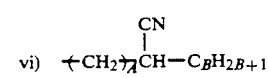

wherein A denotes an integer of 0-2 and B denotes an integer of 1-15 (optically active or inactive); and

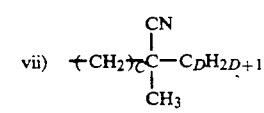

wherein C denotes an integer of 0-2 and D denotes an integer of 1-15 (optically active or inactive).

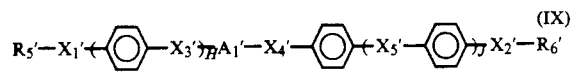

wherein H and J respectively denote 0 or 1 with proviso that H+J=0 or 1; $X_1'$— and $X_2'$ respectively denote a single bond,

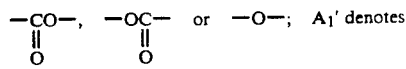

$A_1'$ denotes

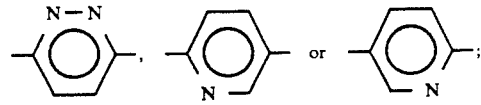

and $X_3'$ and $X_4'$ respectively denote a single bond,

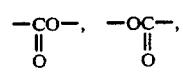

—CH$_2$O— or —OCH$_2$—.

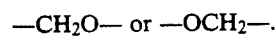

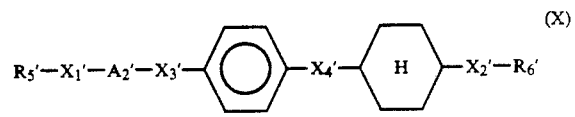

wherein $X_1'$ and $X_2'$ respectively denote a single bond,

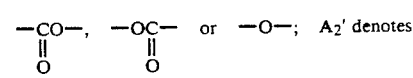

$A_2'$ denotes

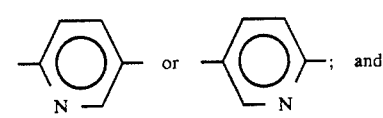

$X_3'$ and $X_4'$ respectively denote a single bond,

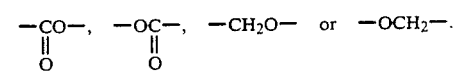

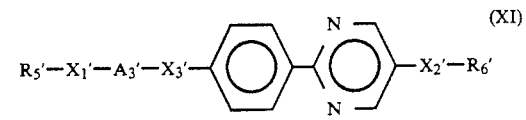

wherein $X_1'$ and $X_2'$ respectively denote a single bond,

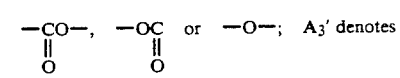

$A_3'$ denotes

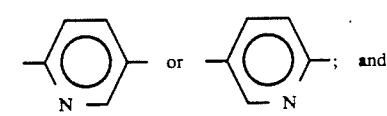

$X_3'$ respectively denotes a single bond,

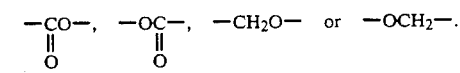

In the above formula (IX), preferred compounds thereof may include those represented by the following formulas (IXa) to (IXc):

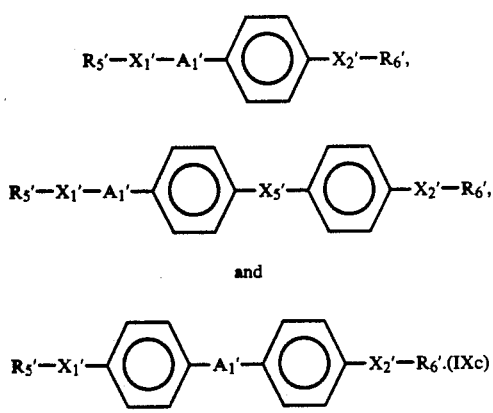
(IXa)
(IXb)
and
(IXc)

In the above formula (x), preferred compounds thereof may include those represented by the following formulas (Xa) and (Xb):

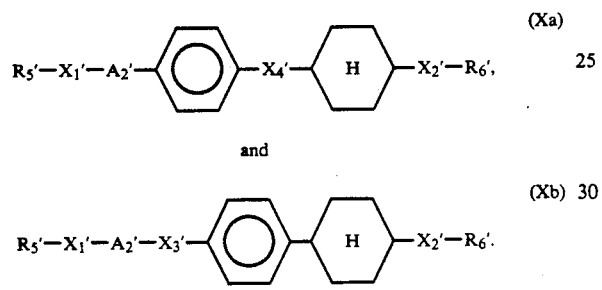
(Xa)
and
(Xb)

In the above-mentioned formula (IX), more preferred compounds thereof may include those represented by the formulas (IXaa) to (IXcc):

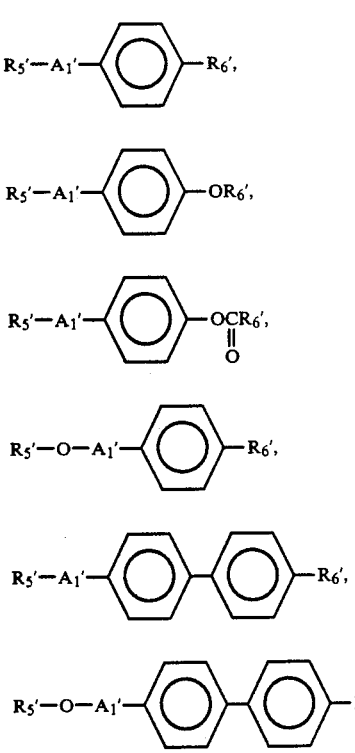
(IXaa)
(IXab)
(IXac)
(IXad)
(IXba)
(IXbb)

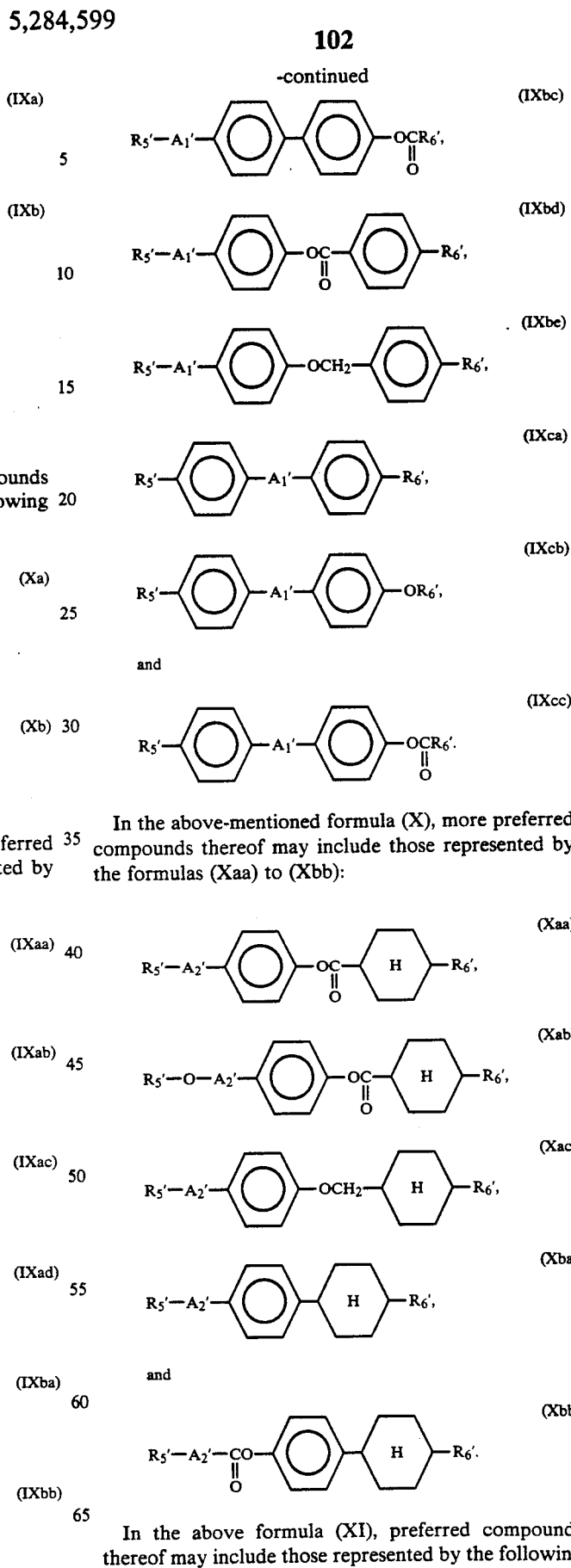
(IXbc)
(IXbd)
(IXbe)
(IXca)
(IXcb)
and
(IXcc)

In the above-mentioned formula (X), more preferred compounds thereof may include those represented by the formulas (Xaa) to (Xbb):

(Xaa)
(Xab)
(Xac)
(Xba)
and
(Xbb)

In the above formula (XI), preferred compounds thereof may include those represented by the following formulas (XIa) to (XIg):

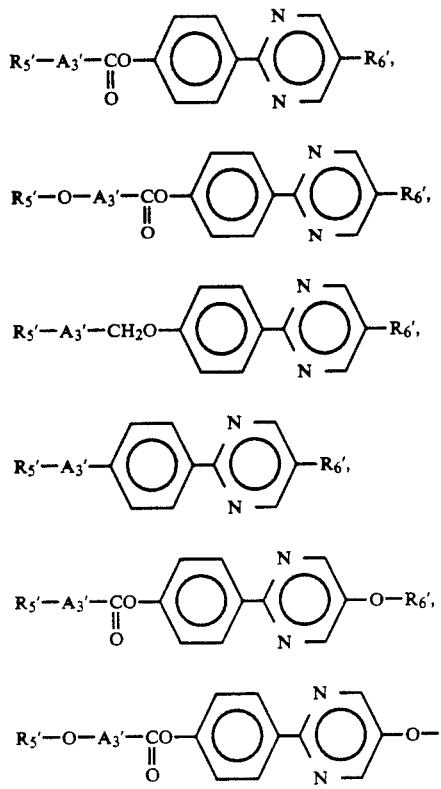

and

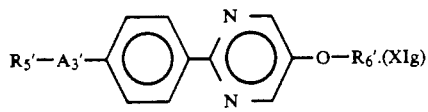

Herein, $R_5'$ and $R_6'$ respectively denote a linear or branched alkyl group having 1-18 carbon atoms capable of including one or two or more non-neighboring methylene groups other than those directly connected to $X_1'$ or $X_2'$ which can be replaced with at least one species of —O—,

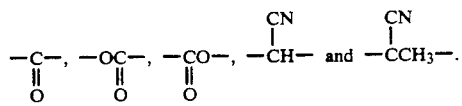

Further, preferred examples of $R_5'$ and $R_6'$ may respectively include those represented by the following groups (i) to (vi):

i) a linear alkyl group having 1-15 carbon atoms;

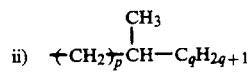

wherein p denotes an integer of 0-5 and q denotes an integer of 1-11 (optically active or inactive);

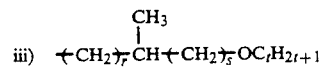

wherein r denotes an integer of 0-6, s denotes 0 or 1, and t denotes an integer of 1-14 (optically active or inactive);

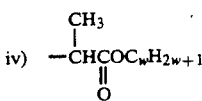

wherein w denotes an integer of 1-15 (optically active or inactive);

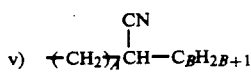

wherein A denotes an integer of 0-2 and B denotes an integer of 1-15 (optically active or inactive); and

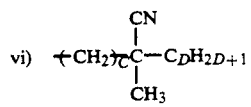

wherein C denotes an integer of 0-2 and D denotes an integer of 1-15 (optically active or inactive).

In formulating the liquid crystal composition according to the present invention, it is desirable to mix 1-500 wt. parts, preferably 2-200 wt. parts, more preferably 3-80 wt. parts, of a compound represented by the formula (I) with 100 wt. parts of at least one species of another mesomorphic compound other than the compound represented by the formula (I).

Alternatively, the liquid crystal composition may desirably contain 1-80 wt. %, preferably 1-60 wt. %, more preferably 1-40 wt. % of a mesomorphic compound represented by the formula (I).

Further, when two or more species of the compounds represented by the formula (I) are used, the two or more species of the compounds of the formula (I) may be used in a total amount of 1-500 wt. parts, preferably 2-200 wt. parts, more preferably 3-80 wt. parts, per 100 wt. parts of at least one species of another mesomorphic compound other than the two or more species of the compounds of the formula (I).

Alternatively, the liquid crystal composition may desirably contain 1-80 wt. %, preferably 1-60 wt. %, more preferably 1-40 wt. %, of the two or more species of the compounds represented by the formula (I).

In the above-mentioned formula (II), at least one of $R_4$ and $R_5$ has an asymmetric carbon atom connected to halogen. Preferred examples of the halogen may include fluorine and chlorine, particularly fluorine.

Further, preferred examples of another one of $R_4$ and $R_5$ may preferably include the following groups (i) to (iii):

(i) n-alkyl group having 1-18 carbon atoms, particularly having 3-12 carbon atom;

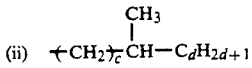

wherein c denotes an integer of 0-7 and d denotes an integer of 1-9 (optically active or inactive when d denotes an integer of 2 or above); and (iii) 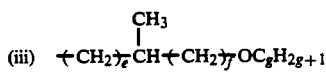

wherein e denotes an integer of 0–7, f denotes 0 or 1, and g denotes an integer of 1–14 (optically active or inactive).

In a case where a=b=1, preferred examples of

 and 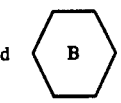 may respectively include

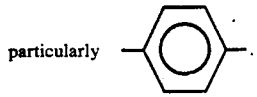

particularly .

In a case where a=1 and b=0 or a=0 and b=1, preferred examples of

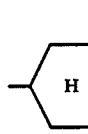 and 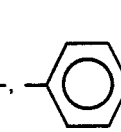 may respectively include  and

, particularly 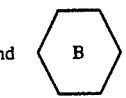.

The mesomorphic compound represented by the general formula (II) may be synthesized through the following reaction schemes.

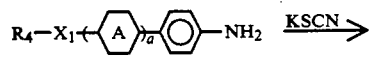

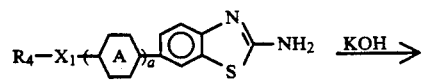

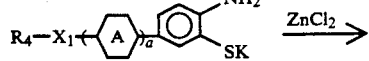

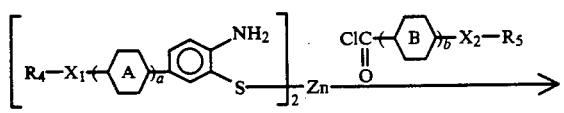

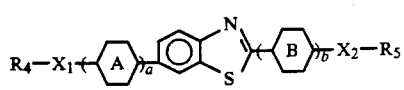

In the above, $R_4$, $R_5$, $X_1$, $X_2$,

, a and b are the same as defined in the general formula (II).

In a case where $X_1$ or $X_2$ is —O—,

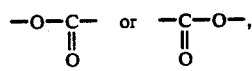

it is possible to form a group of

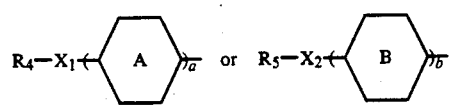

through the following steps (a) to (c):

(a) The hydroxyl group or carboxyl group combined with

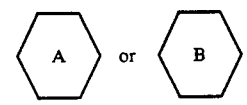

is modified with addition of a protective group into a non-reactive or less reactive group such as —OCH$_3$,

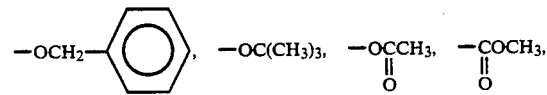

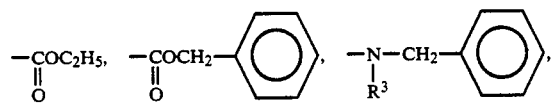

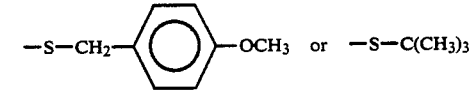

capable of elimination reaction.

(b) Ring closure is effected to form a thiadiazole ring.

(c) The protective group is eliminated and then the

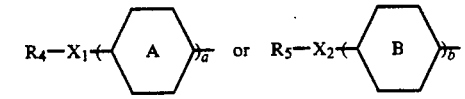

structure is formed.

Specific examples of the mesomorphic compounds represented by the above-mentioned general formula (II) may include those shown by the following structural formulas.

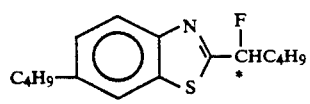 (II-1)
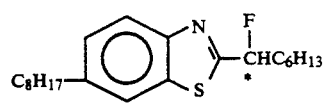 (II-2)
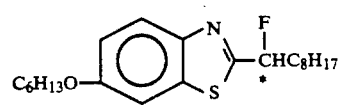 (II-3)
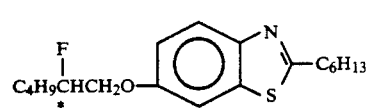 (II-4)
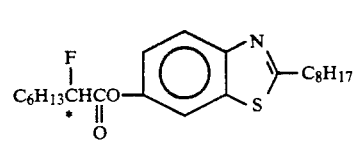 (II-5)
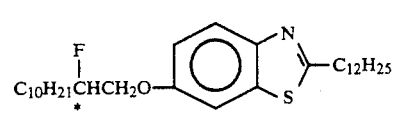 (II-6)
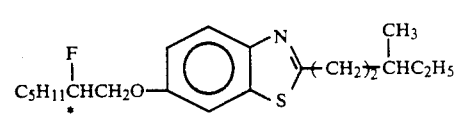 (II-7)
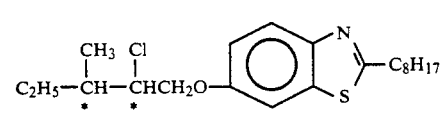 (II-8)
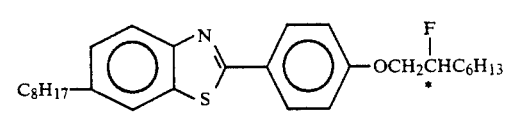 (II-9)
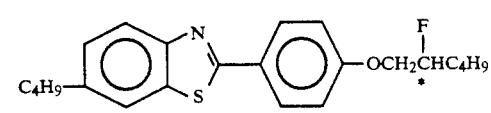 (II-10)
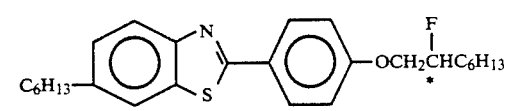 (II-11)
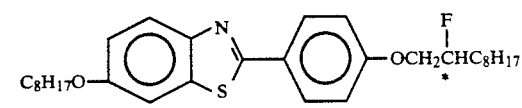 (II-12)
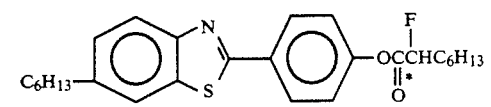 (II-13)

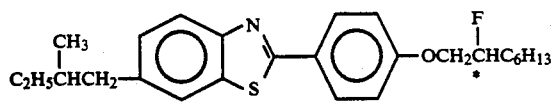 (II-14)
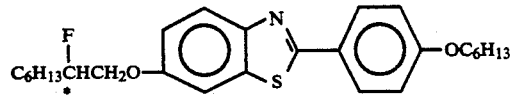 (II-15)
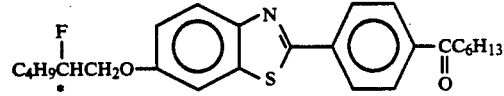 (II-16)
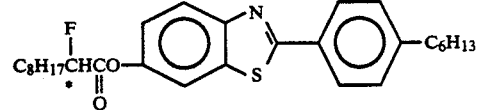 (II-17)
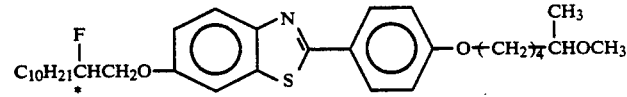 (II-18)
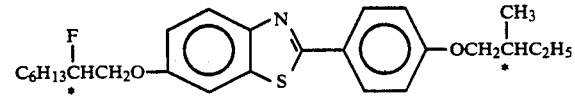 (II-19)
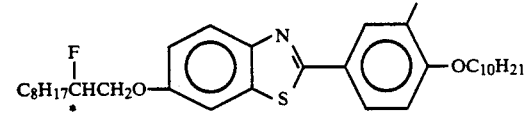 (II-20)
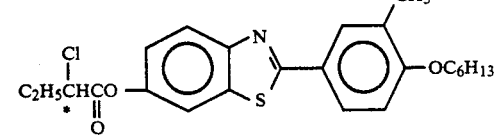 (II-21)
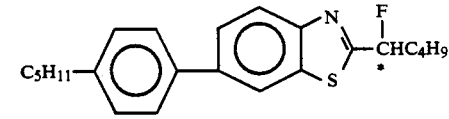 (II-22)
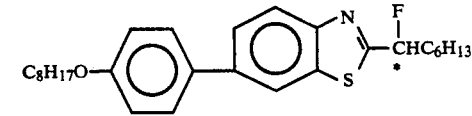 (II-23)
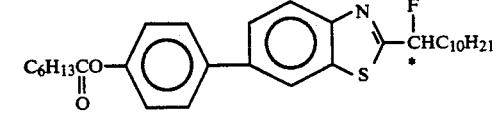 (II-24)
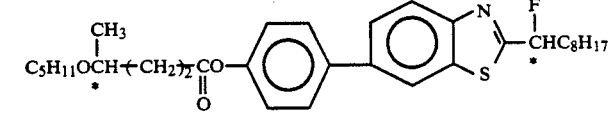 (II-25)

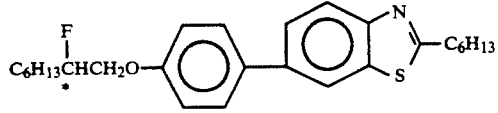 (II-26)
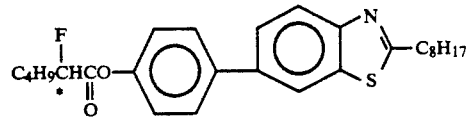 (II-27)
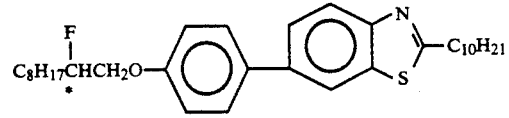 (II-28)
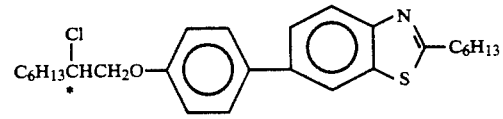 (II-29)
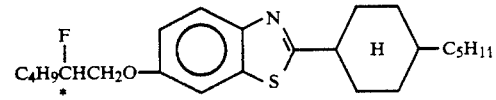 (II-30)
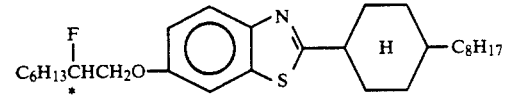 (II-31)
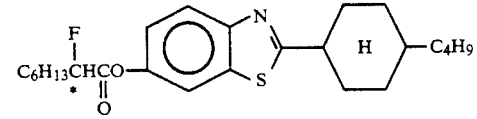 (II-32)
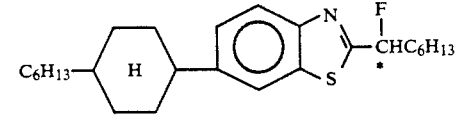 (II-33)
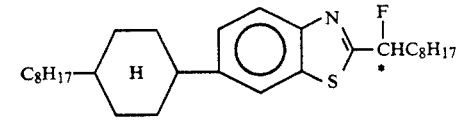 (II-34)
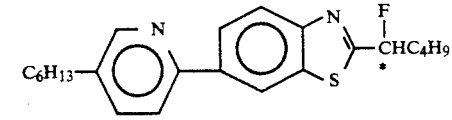 (II-35)
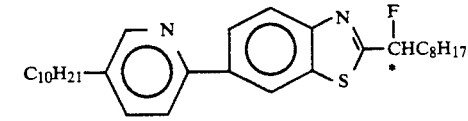 (II-36)
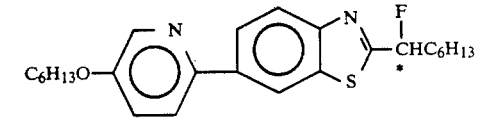 (II-37)

-continued
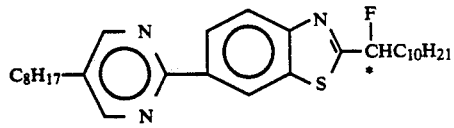 (II-38)
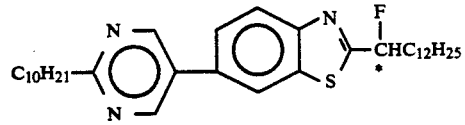 (II-39)
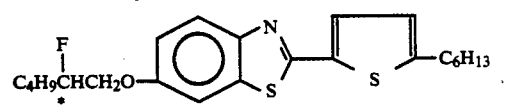 (II-40)
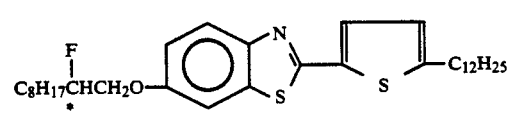 (II-41)
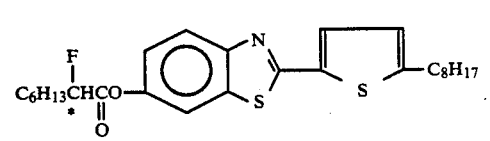 (II-42)
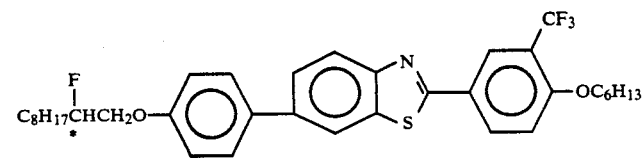 (II-43)
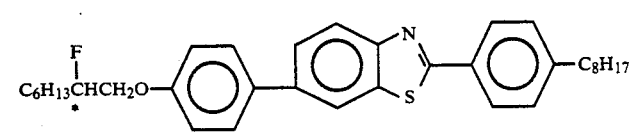 (II-44)
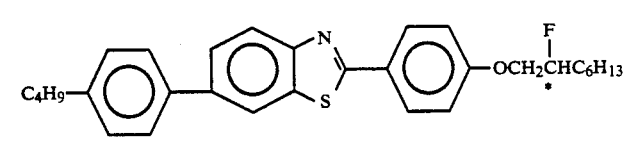 (II-45)
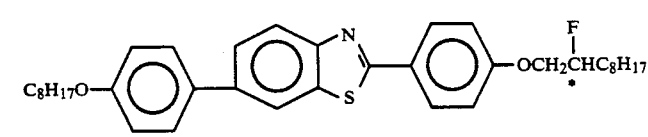 (II-46)
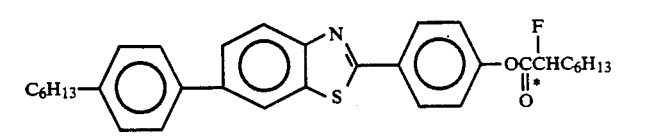 (II-47)
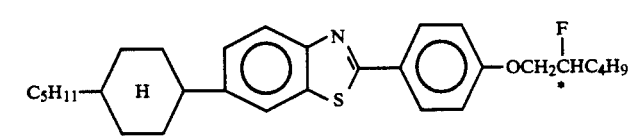 (II-48)
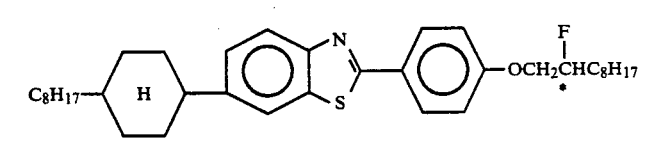 (II-49)

-continued
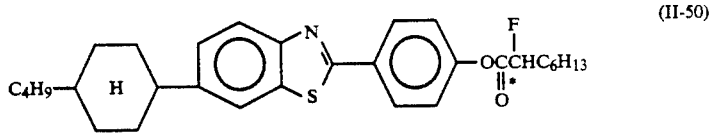 (II-50)
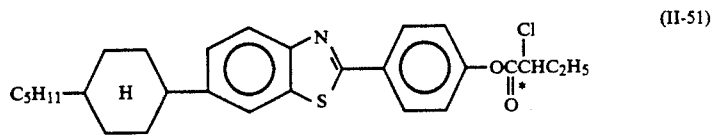 (II-51)
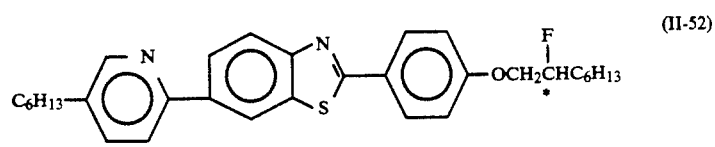 (II-52)
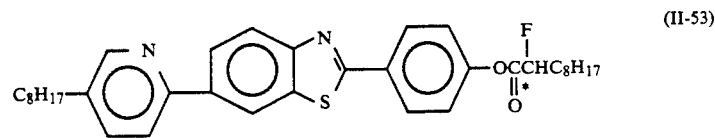 (II-53)
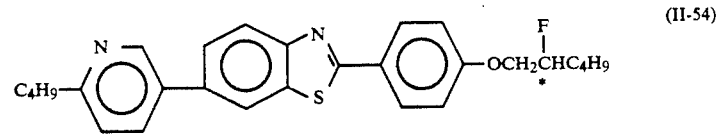 (II-54)
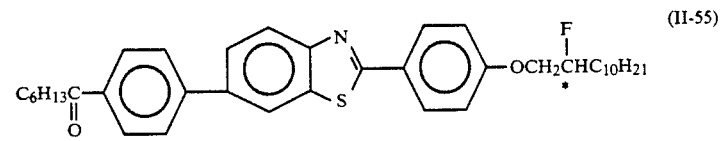 (II-55)
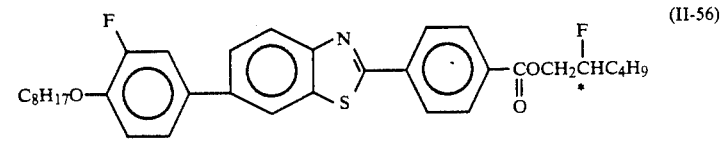 (II-56)
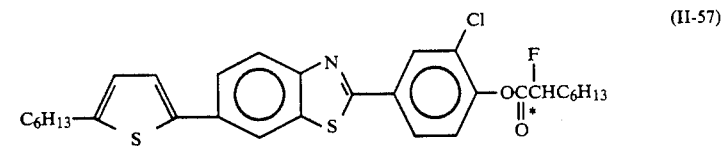 (II-57)
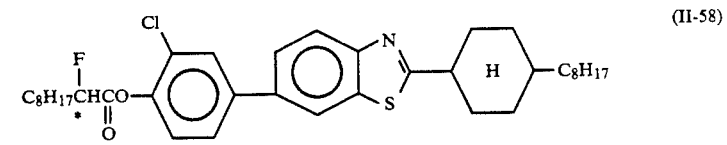 (II-58)
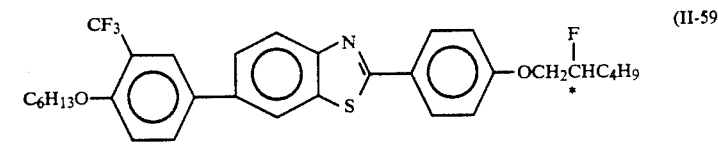 (II-59)
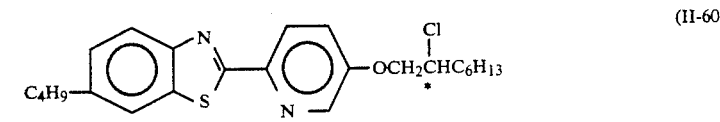 (II-60)

-continued

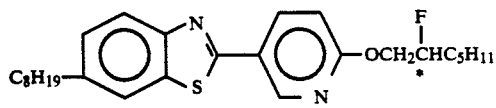 (II-61)

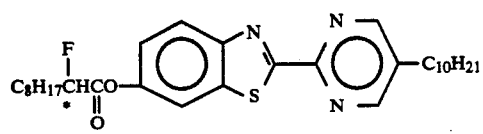 (II-62)

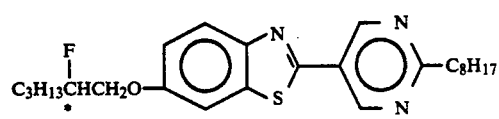 (II-63)

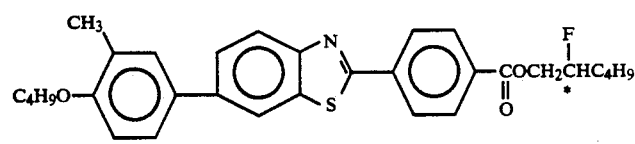 (II-64)

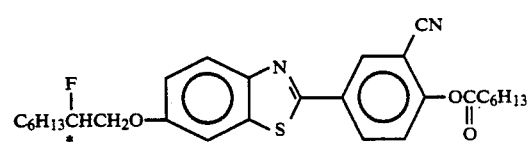 (II-65)

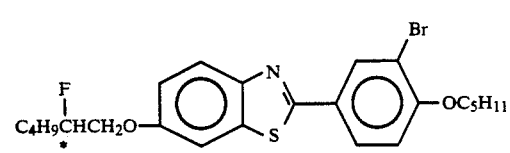 (II-66)

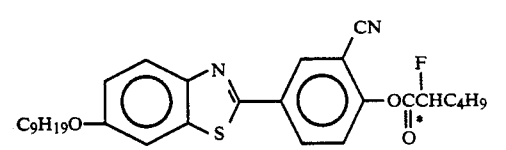 (II-67)

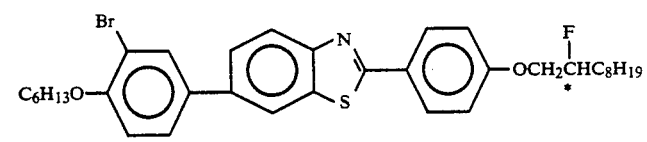 (II-68)

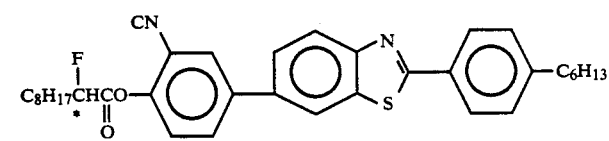 (II-69)

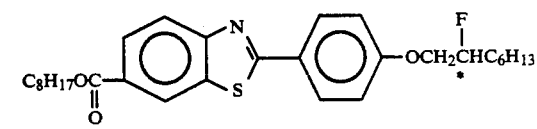 (II-70)

The liquid crystal composition according to the present invention comprises at least one species of the optically active mesomorphic compound represented by the formula (II). The above composition may be obtained by mixing the above compound and at least one species of the above-mentioned another mesomorphic compound represented by the formulas (III) to (XI). Further, the above composition may be obtained by mixing the above compound and at least one species of a ferroelectric liquid crystal, whereby a preferred composition having a larger spontaneous polarization can be obtained to provide improved response speed.

In formulating such a liquid crystal composition, the liquid crystal composition may desirably contain 0.1-99 wt. %, preferably 1-90 wt. %, more preferably 1-80 wt. %, of the optically active mesomorphic compound represented by the formula (II).

Herein, the respective symbols denote the following phases:

Cryst.: crystal,

SmC*: chiral smectic C phase,
SmH*: chiral smectic H phase,
SmA: smectic A phase,
Sm3: un-identified smectic phase,
Ch.: cholesteric phase,
N: nematic phase, and
Iso.: isotropic phase.

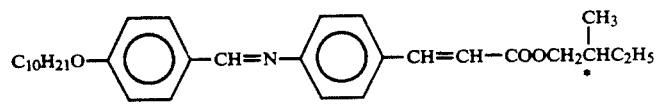  (1)

p-decyloxybenzylidene-p'-amino-2-methylbutylcinnamate (DOBAMBC)

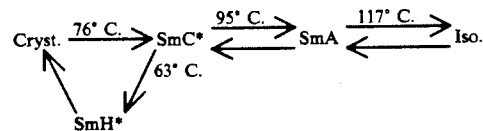

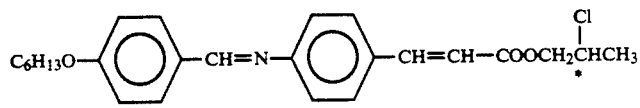  (2)

p-hexyloxybenzylidene-p'-amino-2-chloropropylcinnamate (HOBACPC)

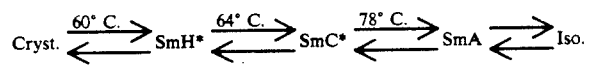

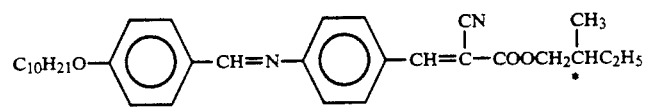  (3)

p-decyloxybenzylidene-p'-amino-2-methylbutyl-α-cyanocinnamate (DOBAMBCC)

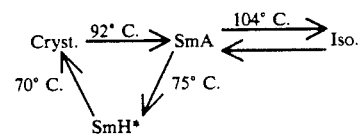

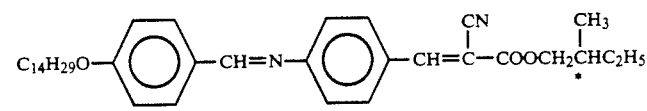  (4)

p-tetradecyloxybenzylidene-p'-amino-2-methylbutyl-α-cyanocinnamate (TDOBAMBCC)

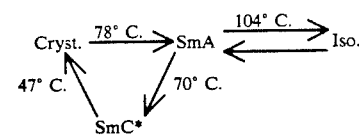

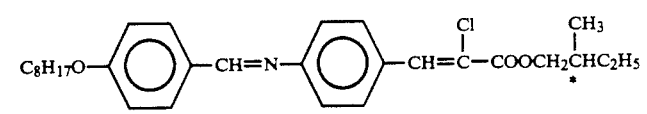  (5)

p-octyloxybenzylidene-p'-amino-2-methylbutyl-α-chlorocinnamate (OOBAMBCC)

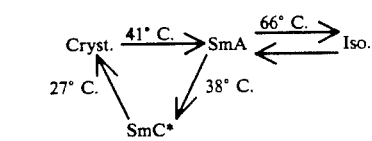

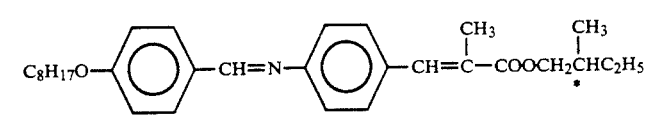  (6)

p-octyloxybenzylidene-p'-amino-2-methylbutyl-α-methylcinnamate

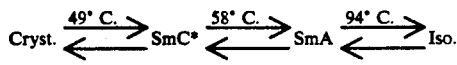

(7)

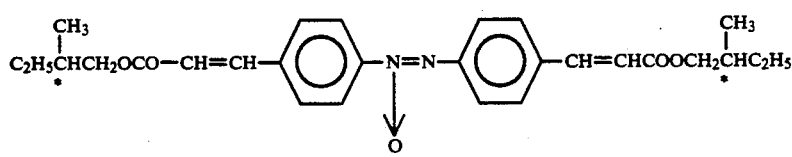

4,4'-azoxycinnamic acid-bis(2-methylbutyl)ester

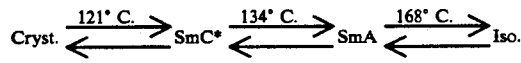

(8)

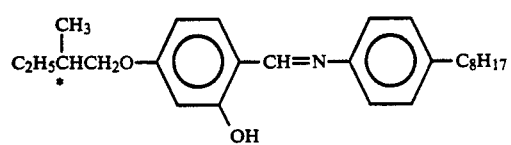

4-O-(2-methylbutyl)resorcylidene-4'-octylaniline (MBRA 8)

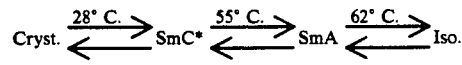

(9)

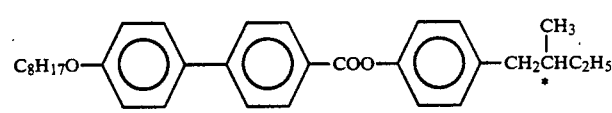

4-(2'-methylbutyl)phenyl-4'-octyloxybiphenyl-4-carboxylate

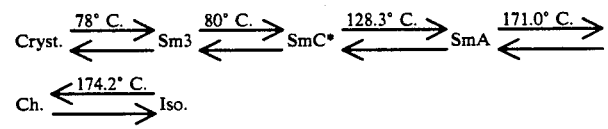

(10)

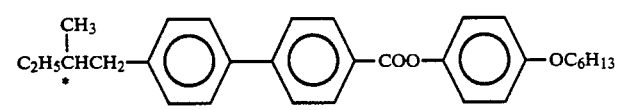

4-hexyloxyphenyl-4-(2''-methylbutyl)biphenyl-4'-carboxylate

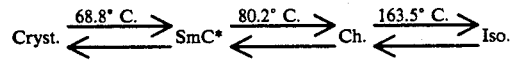

(11)

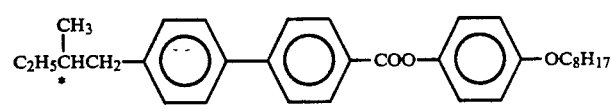

4-octyloxyphenyl-4-(2''-methylbutyl)biphenyl-4'-carboxylate

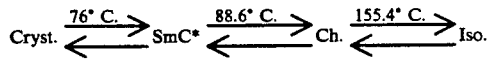

(12)

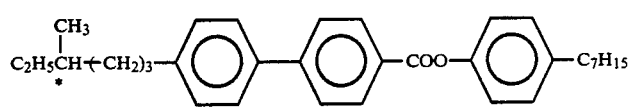

4-heptylphenyl-4-(4''-methylhexyl)biphenyl-4'-carboxylate

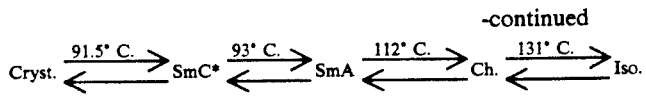

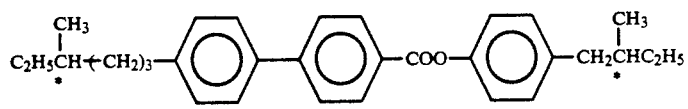

4-(2''-methylbutyl)phenyl-4-(4'''-methylhexyl)biphenyl-4'-carboxylate

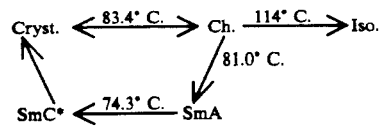

The liquid crystal composition according to the present invention may also comprise the following mesomorphic compounds.

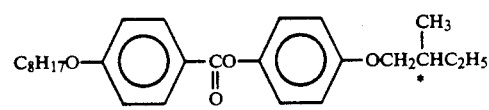

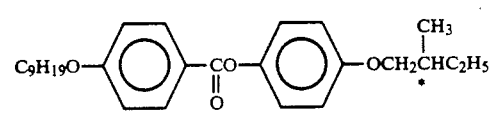

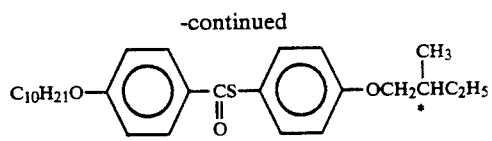

The optically active mesomorphic compound represented by the formula (II) may be mixed with a non-chiral smectic liquid crystal in itself as described hereinafter to provide a liquid crystal composition capable of being used as a ferroelectric liquid crystal.

In this instance, the resultant liquid crystal composition may desirably contain 0.1-99 wt. %, preferably 1-90 wt. %, more preferably 1-80 wt. %, of the optically active mesomorphic compound represented by the formula (II).

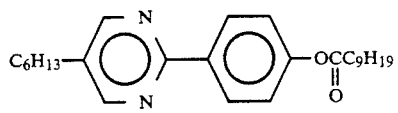

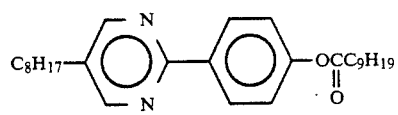

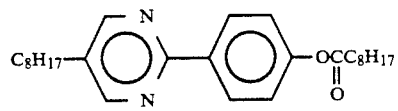

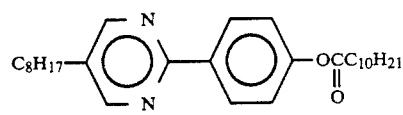

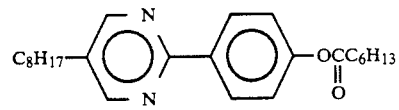

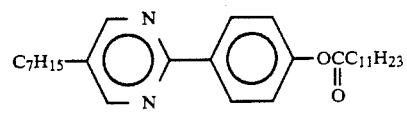

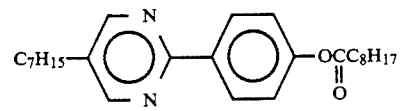

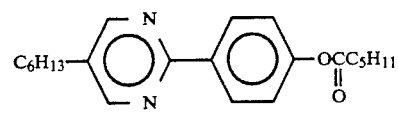

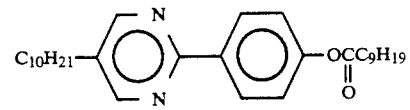

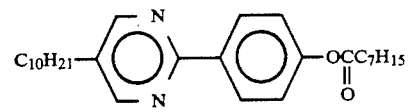

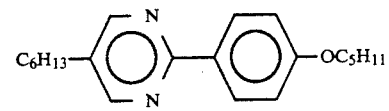

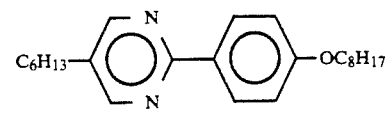

-continued
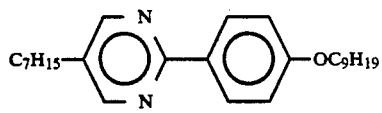
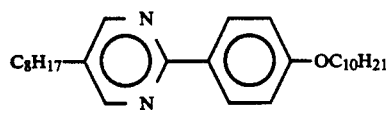
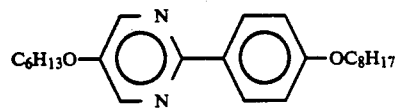
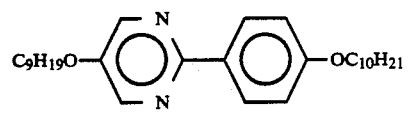
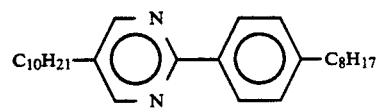
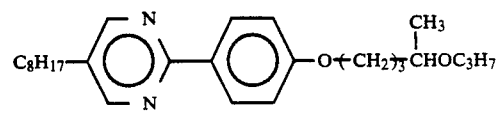
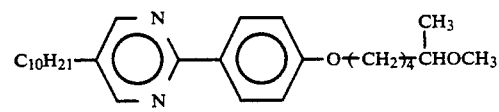
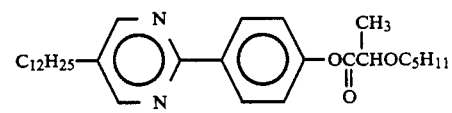
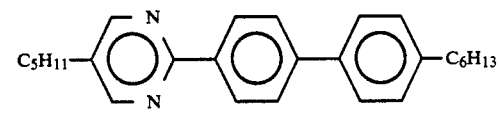
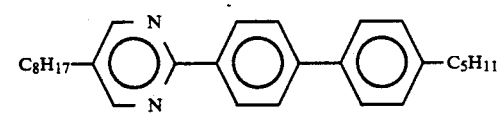
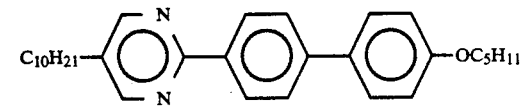
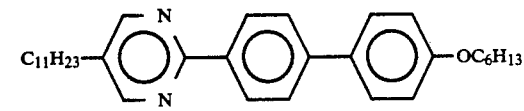
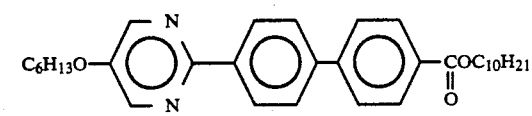
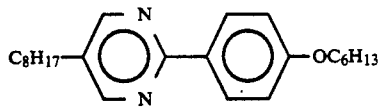
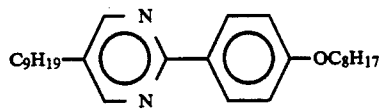
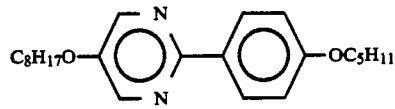
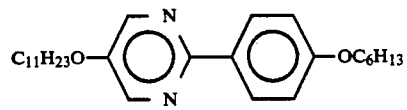
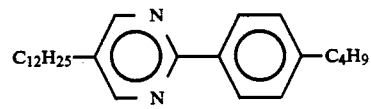
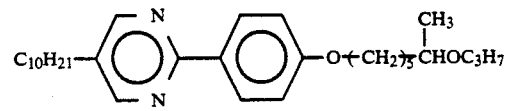
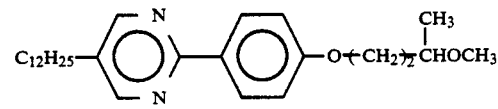
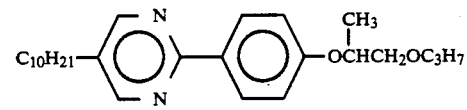
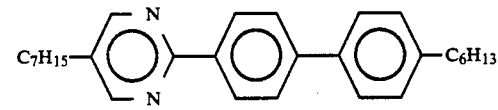
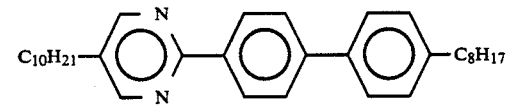
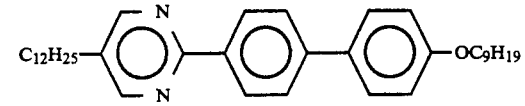
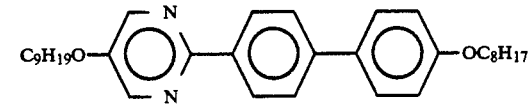
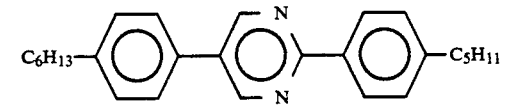

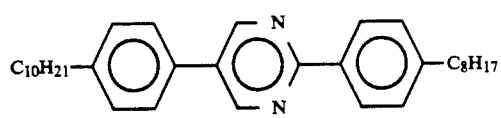
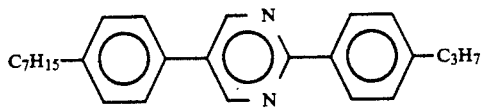
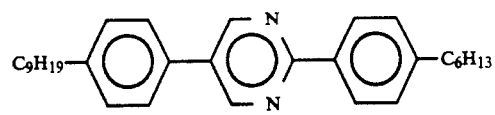
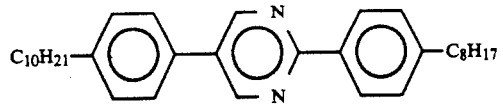
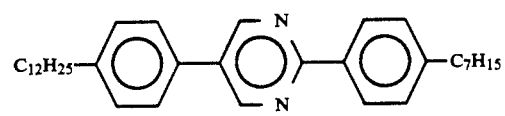
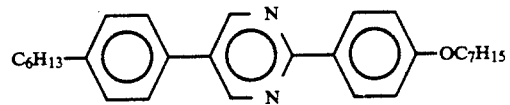
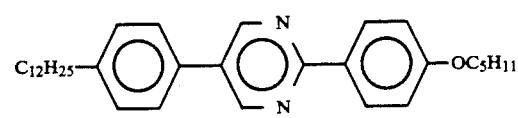
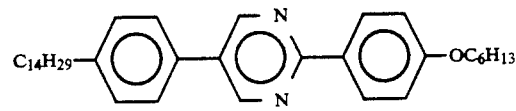
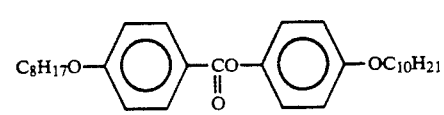
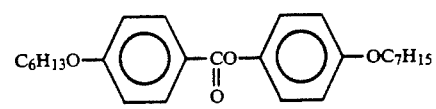
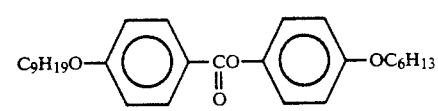
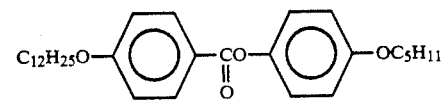
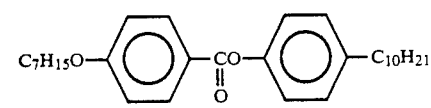
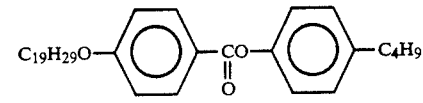
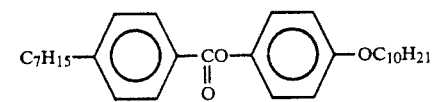
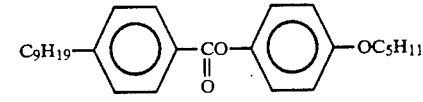
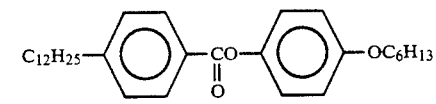
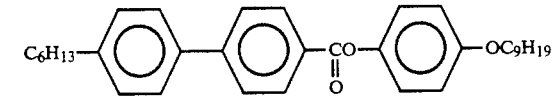
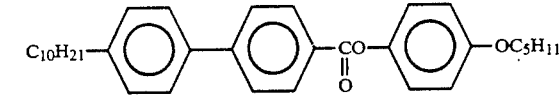
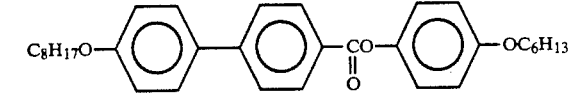
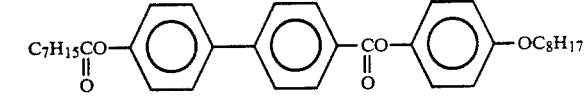

-continued
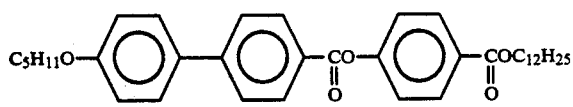
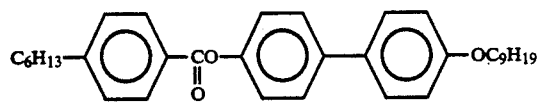
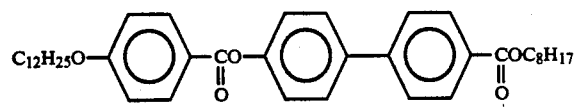
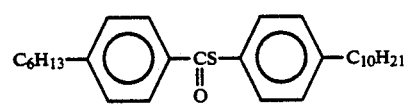
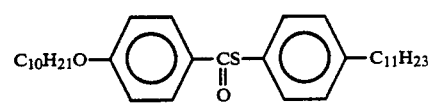
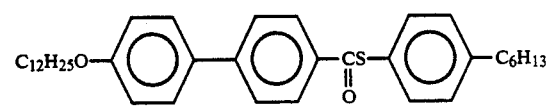
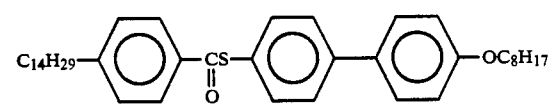
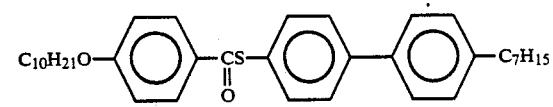
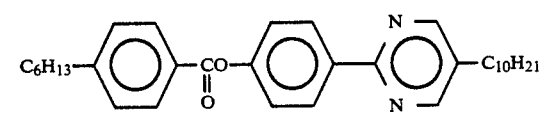
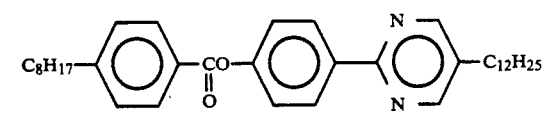
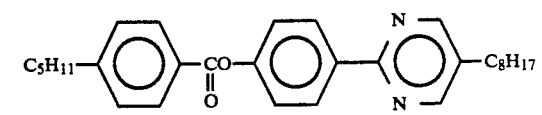
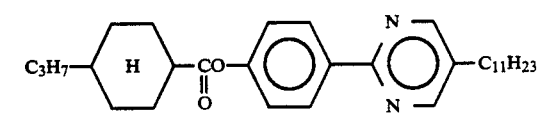
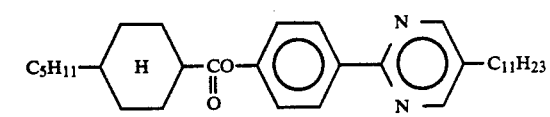

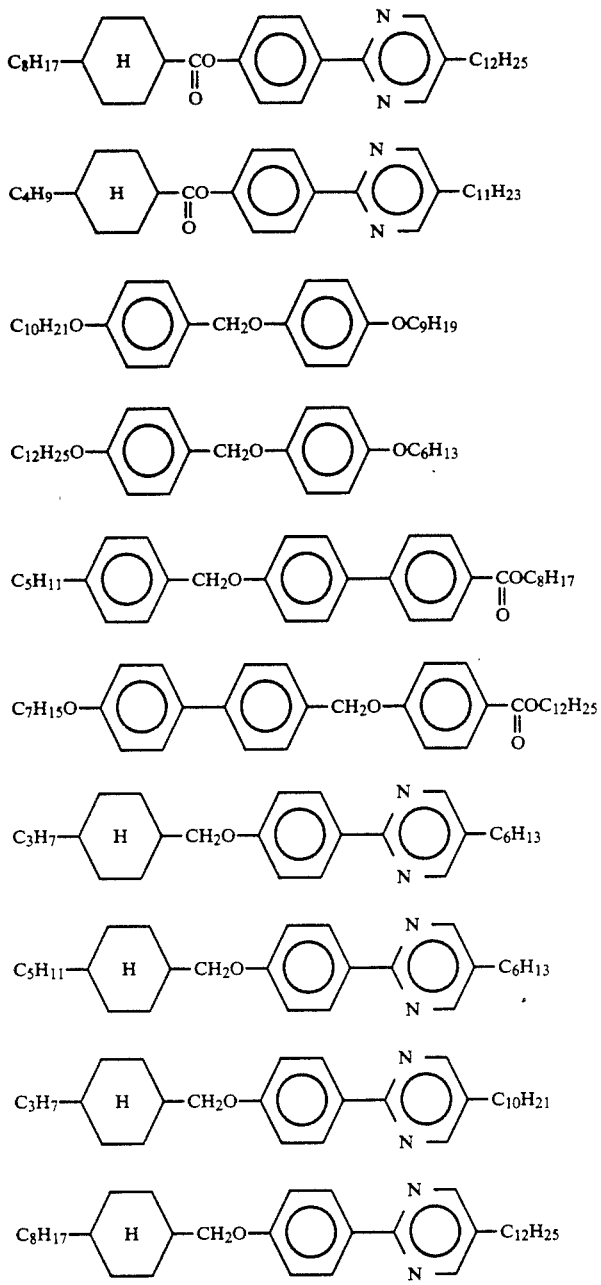

-continued

The resultant liquid crystal composition can have a larger spontaneous polarization depending on its content.

Further, when the optically active mesomorphic compound represented by the formula (II) is added to a nematic liquid crystal, occurrence of a reverse domain (i.e., a striped pattern) in the resultant TN type cell can effectively be prevented.

In this case, the resultant liquid crystal composition may desirably contain 0.01-50 wt. % of the optically active mesomorphic compound represented by the formula (II).

Still further, when the optically active compound represented by the formula (II) is added to a nematic liquid crystal or chiral nematic liquid crystal, the resultant liquid crystal composition can be used for a phase change type liquid crystal device or White-Taylor type GH (guest-host) liquid crystal device, as a chiral nematic liquid crystal.

In this case, the resultant liquid crystal composition may desirably contain 0.01-80 wt. % of the optically active mesomorphic compound represented by the formula (II).

The liquid crystal device according to the present invention may preferably be prepared by heating the liquid crystal composition prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the liquid crystal device utilizing ferroelectricity prepared as described above for explanation of the structure thereof.

Referring to FIG. 1, the liquid crystal device includes a liquid crystal layer 1 assuming a chiral smectic phase disposed between a pair of glass substrates 2 each having thereon a transparent electrode 3 and an insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2–10 wt. %, by spinner coating, dip coating, screen printing, spray coating or roller coating, followed by curing or hardening under prescribed hardening condition (e.g., by heating). The insulating alignment control layer may have a thickness of ordinarily 30 Å–1 micron, preferably 30–3000 Å, further preferably 50–1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a liquid crystal assuming a chiral smectic phase is sealed up to provide a liquid crystal layer 1 in a thickness of generally 0.5 to 20 microns, preferably 1 to 5 microns.

The liquid crystal provided by the composition of the present invention may desirably assume a SmC* phase (chiral smectic C phase) in a wide temperature range including room temperature (particularly, broad in a lower temperature side) and also shows wide drive voltage margin and drive temperature margin when contained in a device.

Particularly, in order to show a good alignment characteristic to form a uniform monodomain, the liquid crystal may show a phase transition series comprising isotropic phase—Ch phase (cholesteric phase)—SmA phase (smectic A phase)—SmC* phase (chiral smectic C phase) on temperature decrease.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

Figure 2:
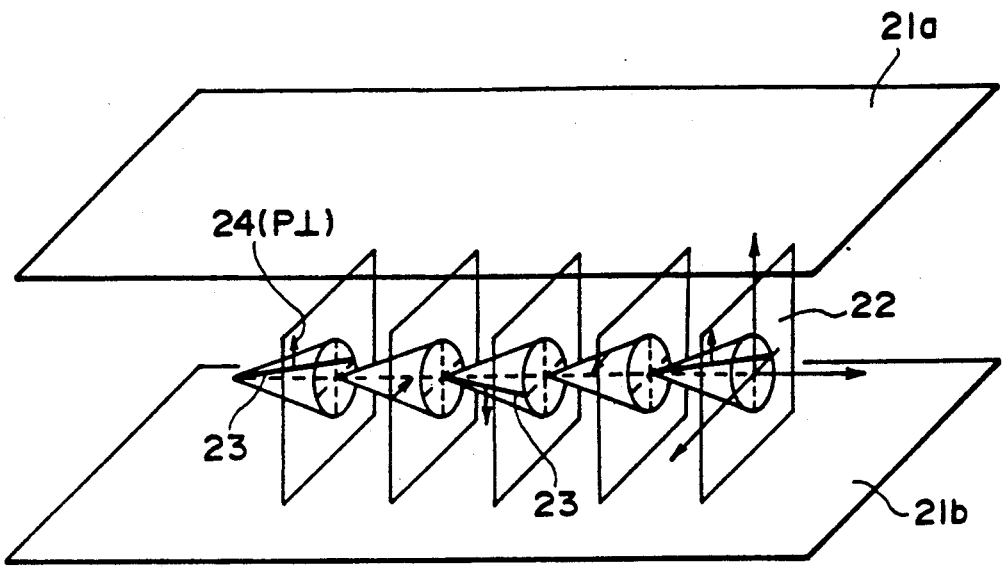
FIGS. 2 and 3 are schematic perspective views of a device cell embodiment for illustrating the operation principle of a liquid crystal device utilizing ferroelectricity of a liquid crystal composition.

FIG. 2 is a schematic illustration of a liquid crystal cell (device) utilizing ferroelectricity for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment (P⊥) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments (P⊥) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
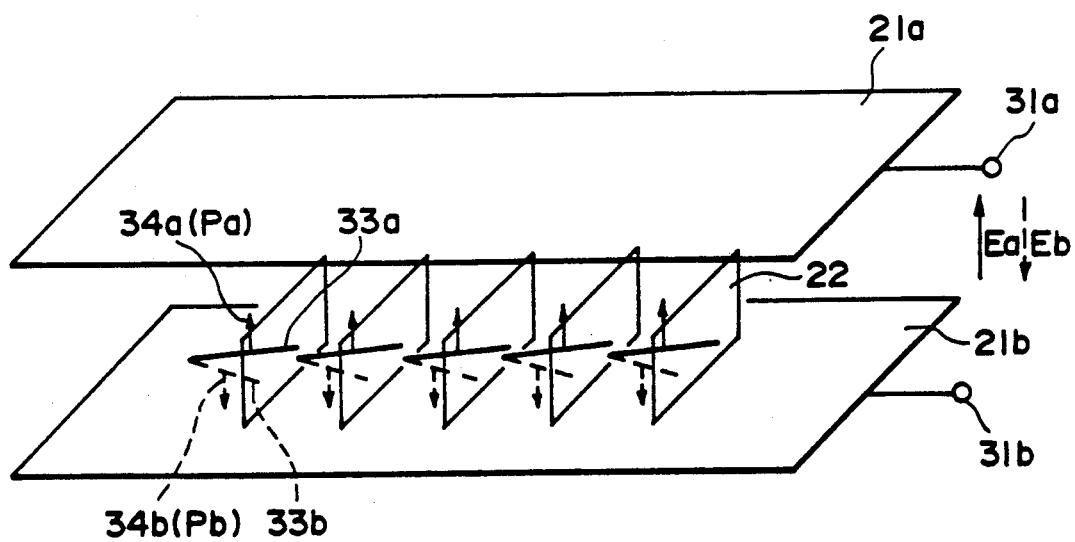

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics by using voltage application means 31a and 31b, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

Figure 4:
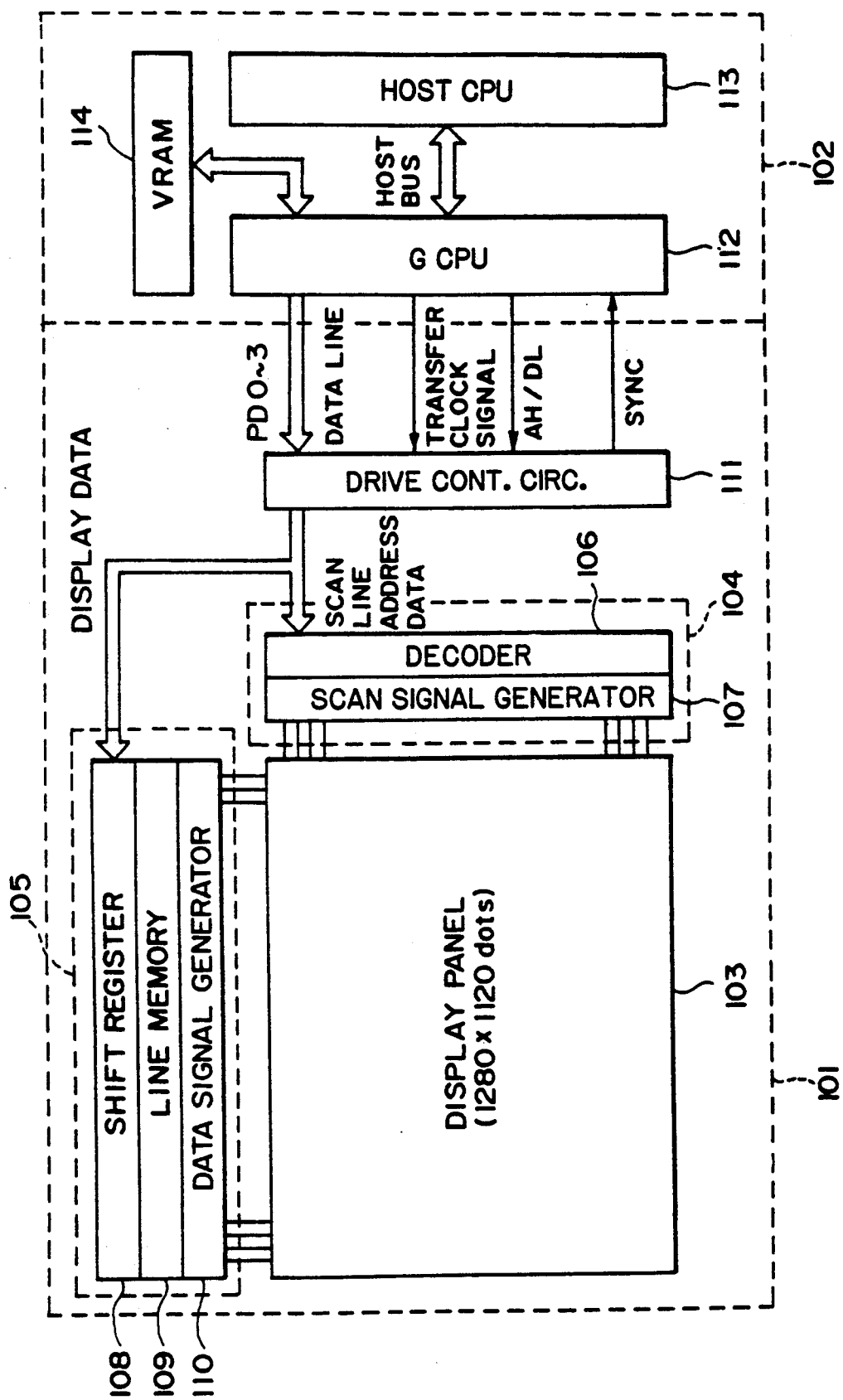
FIG. 4 is a block diagram showing a display apparatus comprising a liquid crystal device utilizing ferroelectricity of a liquid crystal composition and a graphic controller.
Figure 5:
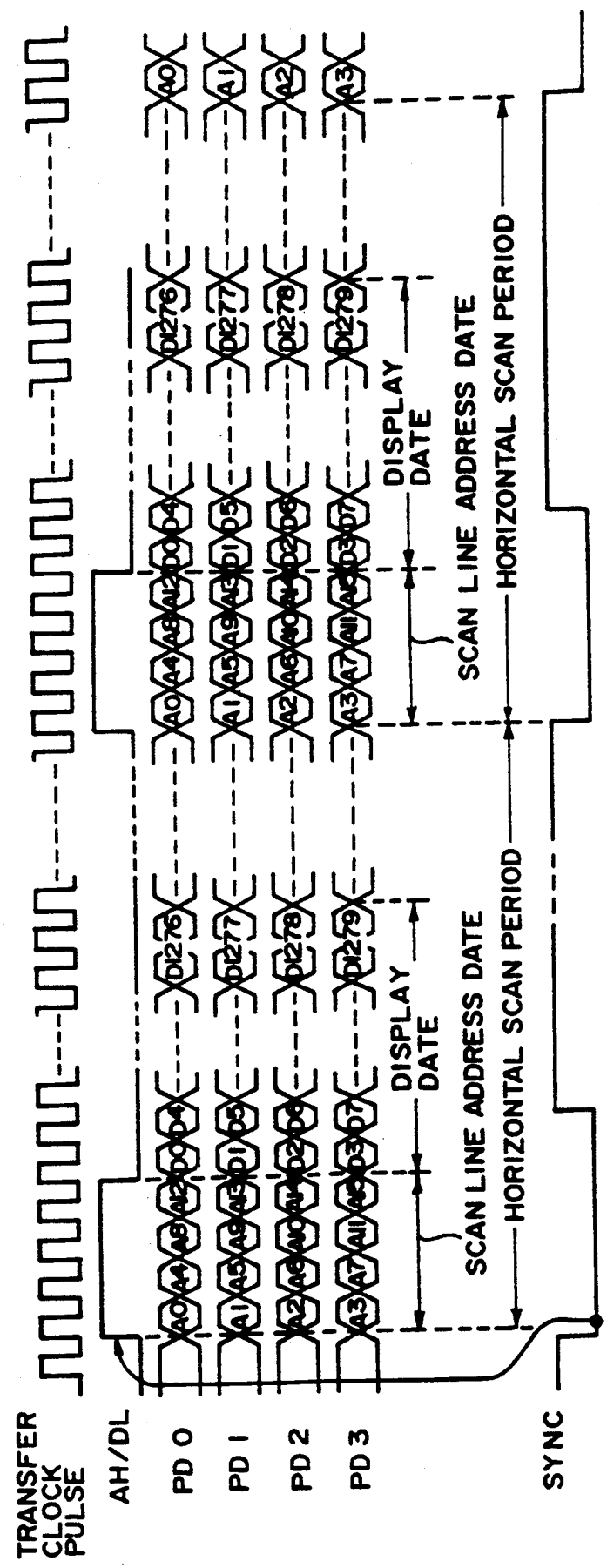
FIG. 5 is a time chart of image data communication showing time correlation between signal transfer and driving with respect to a liquid crystal display apparatus and a graphic controller.

Based on the arrangement and data format comprising image data accompanied with scanning line address data and by adopting communication synchronization using a SYNC signal as shown in FIGS. 4 and 5, there is provided a liquid crystal display apparatus of the present invention which uses the liquid crystal device according to the present invention as a display panel portion.

Image data are generated in a graphic controller 102 in an apparatus body and transferred to a display panel 103 by signal transfer means shown in FIGS. 4 and 5. The graphic controller 102 principally comprises a CPU (central processing unit, hereinafter referred to as "GCPU") 112 and a VRAM (video-RAM, image data storage memory) 114 and is in charge of management and communication of image data between a host CPU 113 and the liquid crystal display apparatus (FLCD) 101. The control method according to the present invention is principally realized in the graphic controller 102.

A light source is disposed at the back of the display panel 103.

Hereinbelow, the present invention will be explained more specifically with reference to examples. It is however to be understood that the present invention is not restricted to these examples.

EXAMPLE 1

2-(p-octylphenyl)-6-hexylbenzothiazole (Example Compound No. I-126) was synthesized through the following steps i)–iii).

C. To the mixture, a solution f 45.0 g of bromine in 135 ml of acetic acid was added dropwise in 40 minutes below 10° C. under strong stirring, followed by reaction for 1.5 hours below 10° C. After the reaction, 500 ml of water was poured into the reaction mixture, followed by heating to dissolve the resultant precipitate. The resultant solution was filtered when hot. Ammonia water was added to the filtrate until the resultant solution became basic, followed by cooling with ice to precipitate a crystal. The crystal was recovered by filtration, followed by washing and drying to obtain a crude product. The crude product was recrystallized from a mixture solvent of n-hexane/benzene (1/1) to obtain 33.0 g of 2-amino-6-hexylbenzothiazole (Yield: 49.9%).

Step ii) Production of zinc 5-hexyl-2-aminobenzenethiol

In a 1 liter-reaction vessel, 30.0 g (0.128 M), 136 ml of water and 136.4 g of KOH were placed, followed by heat-refluxing for 6.5 hours. After the reaction, the reaction mixture was cooled to precipitate a crystal. Then, ethanol was added to the resultant reaction mixture to dissolve the crystal. To the solution, 5N-acetic acid aqueous solution was added dropwise until the resultant mixture showed pH=9 to provide precipitate. The precipitate was filtered off and a solution of 8.9 g of $ZnCl_2$ in 40 ml of 15% acetic acid aqueous solution was added dropwise to the resultant filtrate to precipitate a crystal. The crystal was recovered by filtration after heating for 30 minutes at 70° C., followed by washing with hot water, ethanol and water in succession. The resultant crystal was dried to obtain 27.0 g of zinc 5-hexyl-2-aminobenzenethiol (Yield: 73.4%).

Step iii) Production of 2-(p-octylphenyl)-6-hexylbenzothiazole 20 ml of thionyl chloride was added to 3.74 g (16.0 mM) of p-octylbenzoic acid, followed by heat-refluxing for 1 hour. After the heat-refluxing, excessive thionyl chloride was distilled off under reduced pressure, followed by distilling-off thereof with benzene. To the resultant acid chloride, 3.84 g (8.0 mM) of zinc 5-hexyl-2-aminobenzenethiol was added, followed by stirring for 30 minutes at 200° C. After the reaction, the reaction

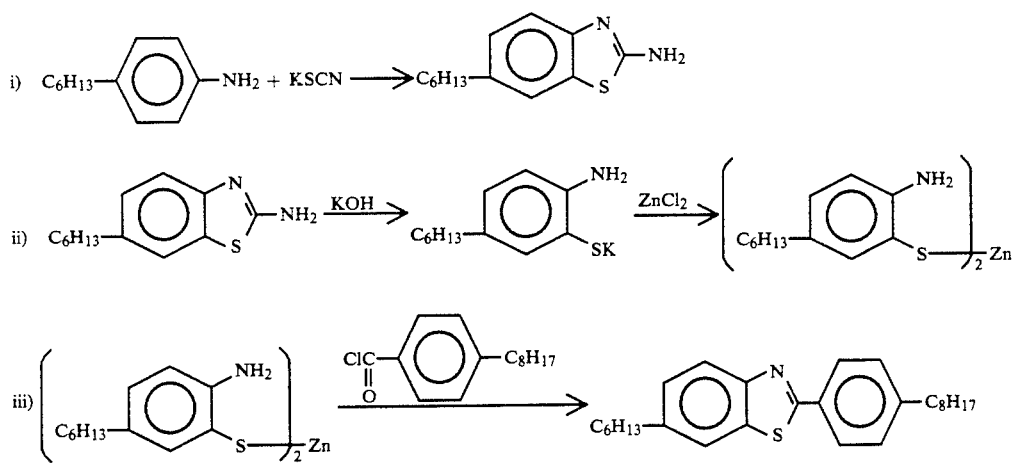

Step i) Production of 2-amino-6-hexylbenzothiazole

In a 2 liter-reaction vessel, 50.0 g(0.28M) of p-hexylaniline, 54.8 g (0.56M) of potassium thiocyanate and 400 ml of acetic acid were placed and cooled below 10° mixture was cooled under room temperature. To the resultant reaction mixture, 40 ml of dilute sodium hydroxide aqueous solution was added, followed by extraction with ethyl acetate, washing with water, drying with anhydrous magnesium sulfate and distilling-off of the solvent to obtain a crude product. The crude product was purified by silica gel column chromatography (eluent: hexane/benzene=10/1) and treated with activated carbon, followed by recrystallization from ethanol to obtain 3.45 g of 2-(p-octylphenyl)-6-hexylbenzothiazole (Yield: 52.9%).

Phase transition temperature (°C.)

Cryst. ⇌(55/41) SmC ⇌(106/104) Iso.

EXAMPLE 5

2-[2-(5-butylpyridyl)]-6-hexylbenzothiazole (Example Compound No. I-334) was synthesized through the following steps i) and ii).

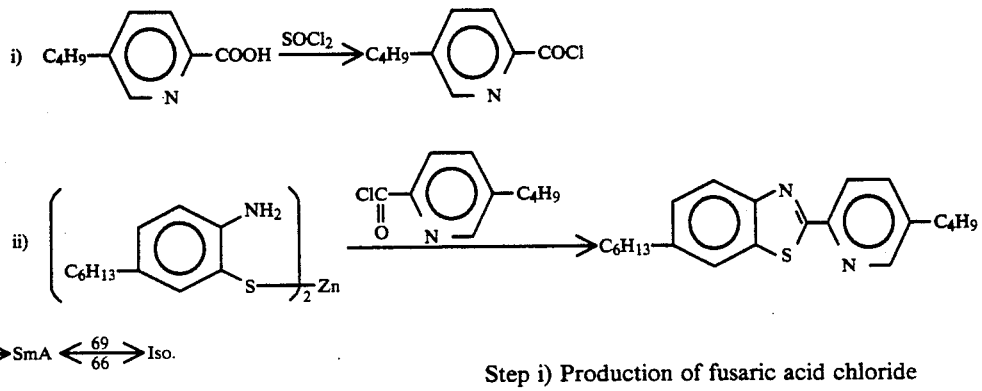

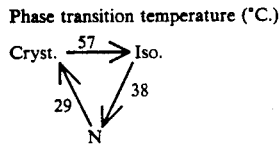

EXAMPLE 2

2-(p-butylphenyl)-6-hexylbenzothiazole (Example Compound No. I-122) was prepared in the same manner as in Example 1.

Phase transition temperature (°C.)

EXAMPLE 3

2-(p-hexylphenyl)-6-hexylbenzothiazole (Example Compound No. I-124) was prepared in the same manner as in Example 1.

Phase transition temperature (°C.)

EXAMPLE 4

2-(p-octyloxyphenyl)-6-hexylbenzothiazole (Example Compound No. I-174) was prepared in the same manner as in Example 1.

Step i) Production of fusaric acid chloride

To 0.72 g. (4.0 mM) of fusaric acid, 10 ml of thionyl chloride was added, followed by heat-refluxing for 1 hour. After the reaction, excessive thionyl chloride in the reaction mixture was distilled off and further distilled off with benzene to obtain fusaric acid chloride.

Step ii) Production of 2-[2-(5-butylpyridyl)]-6-hexylbenzothiazole

To the above-prepared fusaric acid chloride, 0.96 g (2.0 mm) of zinc 5-hexyl-2-aminobenzenethiol was added, followed by stirring for 20 minutes at 230° C. After the reaction, the reaction mixture was cooled under room temperature. To the resultant reaction mixture, 10 ml of dilute sodium hydroxide aqueous solution was added, followed by traction with ethyl acetate, washing with water, drying with anhydrous magnesium sulfate and distilling-off of the solvent to obtain a crude product. The crude product was purified by silica gel column chromatography (eluent: hexane/benzene=10/7) and treated with activated carbon, followed by recrystallization from ethanol to obtain 0.36 g of 2-[2-(5-butylpyridyl)]-6-hexylbenzothiazole (Yield: 51.0%).

Phase transition temperature (°C.)

Cryst. ⇌(80/45) Iso.

EXAMPLE 6

2-[p-(trans-4-pentylcyclohexyl)phenyl]-6-hexylbenzothiazole (Example Compound No. I-293) was synthesized through the following steps i) and ii).

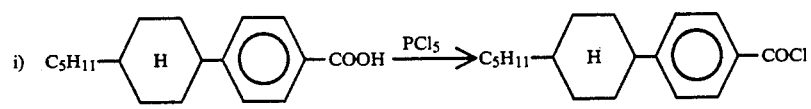

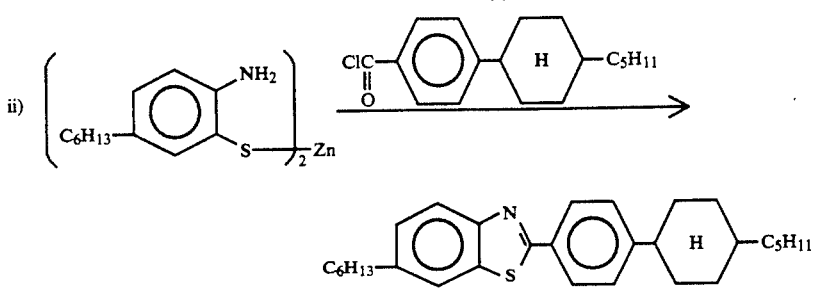

Step i) Production of p-(trans-4-pentylcyclohexyl)benzoic acid chloride

In a 30 ml-reaction vessel, 2.0 g (7.3 mM) of p-(trans-4-pentylcyclohexyl)benzoic acid and 10 ml of benzene were placed. To the mixture, 1.55 g (7.4 mM) of PCl$_5$ was added in 25 minutes to room temperature, followed by heat-refluxing for 4 hours and distilling-off of the solvent to obtain p-(trans-4-pentylcyclohexyl)benzoic acid chloride.

Step ii) Production of 2-[p-(trans-4-pentylcyclohexyl)phenyl]-6-hexylbenzothiazole In a 20 ml-reaction vessel, 1.76 g (3.7 mM) of zinc 5-hexyl-2-aminobenzenethiol and the above-prepared p-(trans-4-pentylcyclohexyl)benzoic acid chloride were placed, followed by stirring for 30 minutes at 200° C. After the reaction, 10 ml of dilute sodium hydroxide aqueous solution was added to the reaction mixture, followed by extraction with chloroform, washing with water, drying with anhydrous magnesium sulfate and distilling-off of the solvent to obtain a crude product. The crude product was purified by silica gel column chromatography (eluent: n-hexane/ethyl acetate=50/1) to obtain 2.4 g of a purified product. The purified product was recrystallized from ethanol to obtain 1.7 g of 2-[p-(trans-4-pentylcyclohexyl)phenyl]-6-hexylbenzothiazole (Yield: 52.1%).

Phase transition temperature (°C.)

Cryst. $\xleftrightarrow{67}$ Sm3 $\xleftrightarrow[124]{125}$ SmA $\xleftrightarrow[204]{204}$ N $\xleftrightarrow[214]{214}$ Iso.

EXAMPLE 7

2-[2-(7-hexyl)fluorenyl]-6-hexylbenzothiazole (Example Compound No. I-390) was prepared in the same manner as in Example 6.

Phase transition temperature (°C.)

Cryst. $\xleftrightarrow[158]{170}$ Sm3 $\xleftrightarrow[169]{172}$ SmA $\xleftrightarrow[235]{236}$ Iso.

EXAMPLE 8

2-(trans-4-pentylcyclohexyl)-6-hexylbenzothiazole (Example Compound No. I-279) was prepared in the following manner.

To 0.867 g (4.0 mM) of trans-4-pentylcyclohexanecarbonyl chloride, 0.964 g (2.0 mM) of zinc 5-hexyl-2-aminobenzene thiol was added, followed by stirring for 30 minutes at 200° C. After the reaction, the reaction mixture was cooled under room temperature. To the resultant reaction mixture, 10 ml of dilute sodium hydroxide aqueous solution was added, followed by extraction with ethyl acetate, washing with water, drying with anhydrous magnesium sulfate and distilling-off off of the solvent to obtain a crude product. The crude product was purified by silica gel column chromatography (eluent: hexane/benzene=30/1) and treated with activated carbon to obtain 0.357 g of 2-(trans-4-pentylcyclohexyl)-6-hexylbenzothiazole (Yield: 48.0%)

Phase transition temperature (°C.)

Cryst. $\xrightarrow{10}$ Iso.

EXAMPLE 9

A liquid crystal composition A was prepared by mixing the following compounds in respectively indicated proportions.

| Structural formula | wt. parts |
|---|---|
| C$_6$H$_{13}$O—⬡—(pyrazine)—C$_8$H$_{17}$ | 46.14 |
| C$_9$H$_{19}$O—⬡—(pyrazine)—C$_8$H$_{17}$ | 23.07 |
| C$_8$H$_{17}$O—⬡—(pyrazine)—C$_{10}$H$_{21}$ | 11.54 |
| C$_3$H$_7$—⟨H⟩—CO—O—⬡—(pyrimidine)—C$_{11}$H$_{23}$ | 3.56 |
| C$_4$H$_9$—⟨H⟩—CO—O—⬡—(pyrimidine)—C$_{11}$H$_{23}$ | 3.56 |
| C$_5$H$_{11}$—⟨H⟩—CO—O—⬡—(pyrimidine)—C$_{11}$H$_{23}$ | 7.13 |

| Structural formula | wt. parts |
|---|---|
| 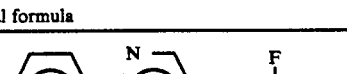 C₁₂H₂₅—〈ring〉—〈ring with N,N〉—OCH₂CHC₆H₁₃ (F) | 2.50 |
| 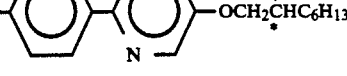 C₁₀H₂₁—〈ring with N,N〉—〈ring〉—OCH₂CHC₆H₁₃ (F) | 2.50 |

The liquid crystal composition A was further mixed with the following Example Compound No. I-124 in the proportions indicated below to provide a liquid crystal composition B.

| Ex. Comp. No. | Structural formula | wt. parts |
|---|---|---|
| I-124 |  C₆H₁₃—〈benzothiazole〉—〈phenyl〉—C₆H₁₃ | 5 |
| | Composition A | 95 |

The liquid crystal composition B showed the following phase transition series.

Phase transition temperature (°C.)

Cryst. —8→ SmC* —53→ SmA —63→ Ch. —76→ Iso.

EXAMPLE 10

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After alumina beads with an average particle size of 2.0 microns were dispersed on one of the glass plates, the two glass plates were applied to each other with a bonding sealing agent (Lixoin Bond, available from Chisso K.K.) so that their rubbed directions were parallel to each other and heated at 100° C. for 60 min. to form a blank cell. The cell gap was found to be about 2 microns as measured by a Berek compensator.

Then, the liquid crystal composition B prepared in Example 9 was heated into an isotropic liquid, and injected into the above prepared cell under vacuum and, after sealing, was gradually cooled at a rate of 20° C./hour to 25° C. to prepare a ferroelectric liquid crystal device.

The ferroelectric liquid crystal device was subjected to measurement of the magnitude of spontaneous polarization Ps and an optical response time (time from voltage application until the transmittance change reaches 90% of the maximum under the application of a peak-to-peak voltage Vpp of 20 V in combination with right-angle cross-nicol polarizers).

The results are shown below.

|  | 10° C. | 30° C. | 45° C. |
|---|---|---|---|
| Response time (μsec) | 528 | 240 | 136 |
| Ps (nC/cm²) | 3.4 | 2.2 | 1.2 |

EXAMPLE 11

A liquid crystal composition C was prepared in the same manner as in Example 9 except that the following Example Compound No. I-174 was used instead of Example Compound No. I-124 in the proportions indicated below.

| Ex. Comp. No. | Structural formula | wt. parts |
|---|---|---|
| I-174 |  C₆H₁₃—〈benzothiazole〉—〈phenyl〉—OC₈H₁₇ | 5 |
| | Composition A | 95 |

The liquid crystal composition C showed the following phase transition series.

Phase transition temperature (°C.)

Cryst. —9→ SmC* —57→ SmA —66→ Ch. —78→ Iso.

EXAMPLE 12

A ferroelectric liquid crystal device was prepared in the same manner as in Example 10 except for using the composition C. The ferroelectric liquid crystal device was subjected to measurement of the magnitude of spontaneous polarization Ps and response time in the same manner as in Example 10, whereby the following results were obtained.

|  | 10° C. | 30° C. | 45° C. |
|---|---|---|---|
| Response time (μsec) | 518 | 226 | 140 |
| Ps (nC/cm²) | 4.1 | 2.9 | 1.9 |

EXAMPLE 13

A liquid crystal composition D was prepared by mixing the following compounds in respectively indicated proportions.

| Structural formula | wt. parts |
|---|---|
| C$_7$H$_{15}$—[pyrimidine]—[phenyl]—OC$_9$H$_{19}$ | 12 |
| C$_{11}$H$_{23}$—[pyrimidine]—[phenyl]—OC$_6$H$_{13}$ | 10 |
| C$_8$H$_{17}$—[pyrimidine]—[phenyl]—O(CH$_2$)$_2$*CH(CH$_3$)CH$_2$C$_2$H$_5$ | 10 |
| C$_{10}$H$_{21}$—[pyrimidine]—[phenyl]—O(CH$_2$)$_2$*CH(CH$_3$)CHOCH$_3$ | 3 |
| C$_8$H$_{17}$—[pyrimidine]—[phenyl]—[phenyl]—OC$_6$H$_{13}$ | 8 |
| C$_6$H$_{13}$O—[phenyl]—OC(O)—[naphthyl]—OC$_9$H$_{19}$ | 4 |
| C$_3$H$_7$—[cyclohexyl-H]—C(O)O—[phenyl]—[pyrimidine]—C$_{11}$H$_{23}$ | 6 |
| C$_8$H$_{17}$—[cyclohexyl-H]—C(O)O—[phenyl]—[pyrimidine]—C$_{11}$H$_{23}$ | 2 |
| C$_5$H$_{11}$—[cyclohexyl-H]—C(O)O—[phenyl]—[pyrimidine]—C$_{11}$H$_{23}$ | 8 |
| C$_{10}$H$_{21}$O—[phenyl]—C(O)O—[phenyl]—OCH$_2$*CH(CH$_3$)CH$_2$C$_2$H$_5$ | 15 |
| C$_4$H$_9$—[cyclohexyl-H]—CH$_2$O—[phenyl]—[pyrimidine]—C$_6$H$_{13}$ | 7 |
| C$_5$H$_{11}$—[cyclohexyl-H]—CH$_2$O—[phenyl]—[pyrimidine]—C$_6$H$_{13}$ | 7 |

-continued

| Structural formula | wt. parts |
|---|---|
| $C_9H_{19}O-\langle\bigcirc\rangle-OCH_2-\langle\bigcirc\rangle-\langle\bigcirc\rangle-C_7H_{15}$ | 4 |
| $C_6H_{13}\overset{CH_3}{\underset{*}{C}}HO-\langle\bigcirc\rangle-\underset{O}{\overset{\parallel}{C}}O-\langle\bigcirc\rangle-\langle\bigcirc\rangle-O\underset{O}{\overset{\parallel}{C}}\overset{CH_3}{\underset{*}{C}}HOC_4H_9$ | 2 |
| $C_{12}H_{25}-[\text{pyrimidine}]-\langle\bigcirc\rangle-O\underset{O}{\overset{\parallel}{C}}\overset{Cl}{\underset{*}{C}}H-\overset{CH_3}{\underset{*}{C}}HC_2H_5$ | 2 |

The liquid crystal composition D was further mixed with the following Example Compounds in the proportions indicated below to provide a liquid crystal composition E.

| Ex. Comp. No. | Structural formula | wt. parts |
|---|---|---|
| I-13 | $C_8H_{17}O-[\text{benzothiazole}]-C_{12}H_{25}$ | 3 |
| I-23 | $C_4H_9-\langle\bigcirc\rangle-[\text{benzothiazole}]-C_6H_{13}$ | 3 |
| | Composition D | 94 |

A ferroelectric liquid crystal device was prepared in the same manner as in Example 10 except for using the composition E. The ferrroelectric liquid crystal device was subjected to measurement of response time in the same manner as in Example 10, whereby the following results were obtained.

| | 10° C. | 25° C. | 40° C. |
|---|---|---|---|
| Response time (μsec) | 730 | 355 | 191 |

COMPARATIVE EXAMPLE 13

A ferroelectric liquid crystal device was prepared in the same manner as in Example 10 except that the liquid crystal composition D prepared in Example 13 was injected into a cell. The measured values of the response time of the device were as follows.

| | 10° C. | 25° C. | 40° C. |
|---|---|---|---|
| Response time (μsec) | 784 | 373 | 197 |

EXAMPLE 14

A liquid crystal composition F was prepared by mixing the following example compounds in the indicated proportions with the liquid crystal composition D prepared in Example 13.

| Ex. Comp. No. | Structural formula | wt. parts |
|---|---|---|
| I-34 | $C_6H_{13}-\langle\bigcirc\rangle-[\text{benzothiazole}]-C_8H_{17}$ | 3 |
| I-40 | $C_7H_{15}O-\langle\bigcirc\rangle-[\text{benzothiazole}]-C_8H_{17}$ | 3 |
| I-126 | $C_6H_{13}-[\text{benzothiazole}]-\langle\bigcirc\rangle-C_8H_{17}$ | 3 |
| | Composition D | 91 |

A ferroelectric liquid crystal device was prepared in the same manner as in Example 10 except that the above liquid crystal composition F was used, and the device was subjected to measurement of optical response time. The results of the measurement are shown below.

| | 10° C. | 25° C. | 40° C. |
|---|---|---|---|
| Response time (μsec) | 663 | 324 | 180 |

EXAMPLE 15

A liquid crystal composition G was prepared by mixing the following example compounds in the indicated proportions with the liquid crystal composition D prepared in Example 13.

| Ex. Comp. No. | Structural formula | wt. parts |
|---|---|---|
| I-46 | C$_8$H$_{17}$O—(phenyl)—(benzothiazole)—C$_{12}$H$_{25}$ | 2 |
| I-126 | C$_6$H$_{13}$—(benzothiazole)—(phenyl)—C$_8$H$_{17}$ | 4 |
| I-279 | C$_6$H$_{13}$—(benzothiazole)—(cyclohexyl-H)—C$_5$H$_{11}$ | 4 |

| Ex. Comp. No. | Structural formula | wt. parts |
|---|---|---|
| | Composition D | 90 |

A ferroelectric liquid crystal device was prepared in the same manner as in Example 10 except that the above liquid crystal composition G was used, and the device was subjected to measurement of optical response time. The results of the measurement are shown below.

| | 10° C. | 25° C. | 40° C. |
|---|---|---|---|
| Response time (μsec) | 631 | 310 | 177 |

EXAMPLE 16

A liquid crystal composition H was prepared by mixing the following compounds in respectively indicated proportions.

| Structural formula | wt. parts |
|---|---|
| C$_8$H$_{17}$—(pyrimidine)—(phenyl)—OC$_6$H$_{13}$ | 10 |
| C$_8$H$_{17}$—(pyrimidine)—(phenyl)—OC$_9$H$_{19}$ | 5 |
| C$_{10}$H$_{21}$—(pyrimidine)—(phenyl)—OCOC$_8$H$_{17}$ | 7 |
| C$_{10}$H$_{21}$—(pyrimidine)—(phenyl)—O(CH$_2$)$_3$CH(CH$_3$)OC$_3$H$_7$ | 7 |
| C$_{12}$H$_{25}$—(pyrimidine)—(phenyl)—O(CH$_2$)$_4$CH(CH$_3$)OCH$_3$ | 6 |
| C$_5$H$_{11}$—(pyrimidine)—(phenyl)—(phenyl)—C$_6$H$_{13}$ | 5 |
| C$_7$H$_{15}$—(pyrimidine)—(phenyl)—(phenyl)—C$_6$H$_{13}$ | 5 |
| C$_4$H$_9$—(cyclohexyl-H)—COO—(phenyl)—(pyrimidine)—C$_{12}$H$_{25}$ | 8 |

-continued

| Structural formula | wt. parts |
|---|---|
| 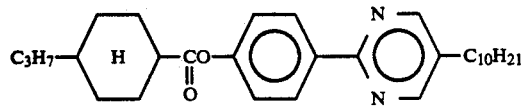 | 8 |
| 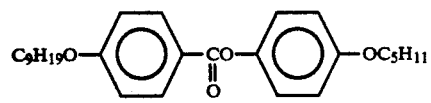 | 20 |
| 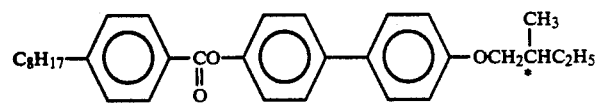 | 5 |
| 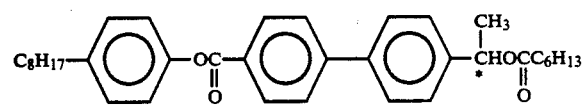 | 5 |
| 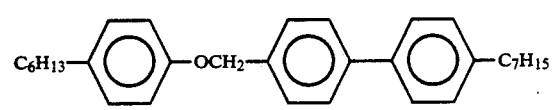 | 6 |
| 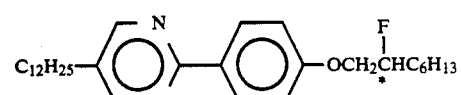 | 3 |

The liquid crystal composition H was further mixed with the following Example Compounds in the proportions indicated below to provide a liquid crystal composition I.

same manner as in Example 10, whereby the following results were obtained.

| Ex. Comp. No. | Structural formula | wt. parts |
|---|---|---|
| I-122 | 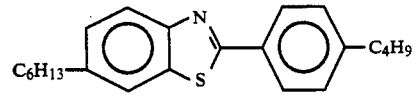 | 2 |
| I-264 | 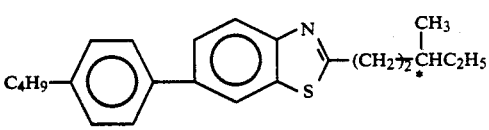 | 2 |
| I-293 | 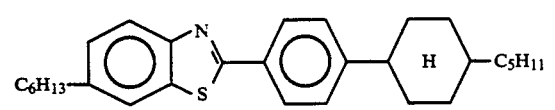 | 2 |
| I-319 | 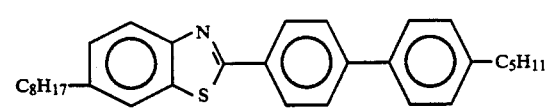 | 2 |
| Composition H | | 92 |

A ferroelectric liquid crystal device was prepared in the same manner as in Example 10 except for using the composition I. The ferroelectric liquid crystal device was subjected to measurement of response time in the

| | 10° C. | 25° C. | 40° C. |
|---|---|---|---|
| Response time (μsec) | 576 | 274 | 150 |

COMPARATIVE EXAMPLE 16

A ferroelectric liquid crystal device was prepared in the same manner as in Example 10 except that the liquid crystal composition H prepared in Example 16 was injected into a cell. The measured values of the response time of the device were as follows.

|  | 10° C. | 25° C. | 40° C. |
|---|---|---|---|
| Response time (μsec) | 653 | 317 | 159 |

EXAMPLE 17

A liquid crystal composition J was prepared by mixing the following example compounds int he indicated proportions with the liquid crystal composition H prepared in Example 16.

was subjected to measurement of optical response time. The results of the measurement are shown below.

|  | 10° C. | 25° C. | 40° C. |
|---|---|---|---|
| Response time (μsec) | 596 | 288 | 149 |

EXAMPLE 18

A liquid crystal composition K was prepared by mixing the following example compounds in the indicated proportions with the liquid crystal composition H prepared in Example 16.

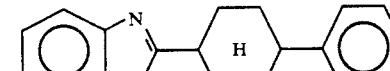

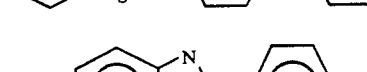

A ferroelectric liquid crystal device was prepared in the same manner as in Example 10 except that the above liquid crystal composition J was used, and the device A ferroelectric liquid crystal device was prepared in the same manner as in Example 10 except that the above liquid crystal composition K was used, and the device was subjected to measurement of optical response time. The results of the measurement are shown below.

|  | 10° C. | 25° C. | 40° C. |
| --- | --- | --- | --- |
| Response time (μsec) | 560 | 272 | 141 |

EXAMPLE 19

A liquid crystal composition L was prepared by mixing the following compounds in respectively indicated proportions.

| Structural formula | wt. parts |
| --- | --- |
| $C_9H_{19}$—pyrazine—phenyl—$OC_9H_{19}$ | 6 |
| $C_{10}H_{21}$—pyrazine—phenyl—$OC_8H_{17}$ | 6 |
| $C_8H_{17}$—pyridine—phenyl—$O(CH_2)_3\overset{*}{C}H(CH_3)C_2H_5$ | 7 |
| $C_{11}H_{23}O$—pyrimidine—phenyl—$O(CH_2)_2\overset{*}{C}H(CH_3)C_2H_5$ | 14 |
| $C_{10}H_{21}$—pyridine—phenyl—$C_6H_{13}$ | 8 |
| $C_6H_{13}$—pyrazine—phenyl—phenyl—$OC_4H_9$ | 4 |
| $C_8H_{17}$—phenyl—pyridine—phenyl—$OC_5H_{11}$ | 2 |
| $C_3H_7$—cyclohexyl(H)—COO—phenyl—pyridine—$C_{12}H_{25}$ | 10 |
| $C_5H_{11}$—cyclohexyl(H)—COO—phenyl—pyridine—$C_{12}H_{25}$ | 5 |
| $C_{10}H_{21}O$—phenyl—C(=O)S—phenyl—$OC_8H_{17}$ | 10 |
| $C_6H_{13}$—phenyl—COO—phenyl—phenyl—$OCH_2\overset{*}{C}H(CH_3)C_2H_5$ | 7 |

-continued

| Structural formula | wt. parts |
|---|---|
| 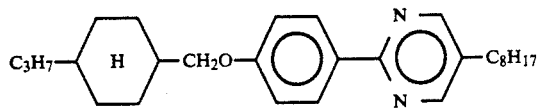 | 7 |
| 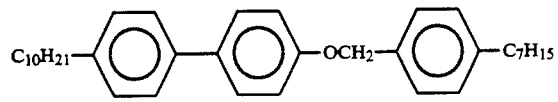 | 5 |
| 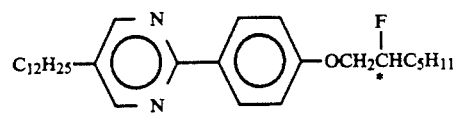 | 2 |
| 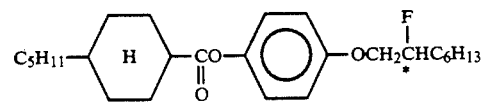 | 2 |
| 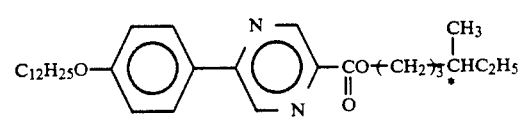 | 2 |
| 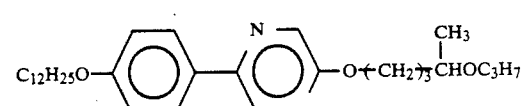 | 3 |

The liquid crystal composition L was further mixed with the following Example Compounds in the proportions indicated below to provide a liquid crystal composition M. The ferroelectric liquid crystal device was subjected to measurement of response time in the same manner as in Example 10, whereby the following results were obtained.

| Ex. Comp. No. | Structural formula | wt. parts |
|---|---|---|
| I-124 | 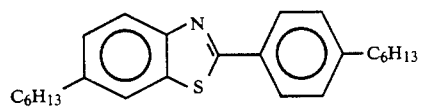 | 3 |
| I-259 | 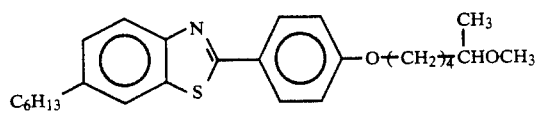 | 3 |
| I-412 | 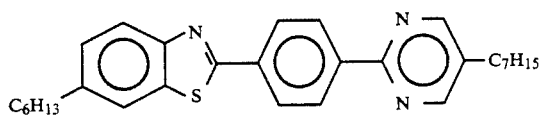 | 2 |
| I-416 | 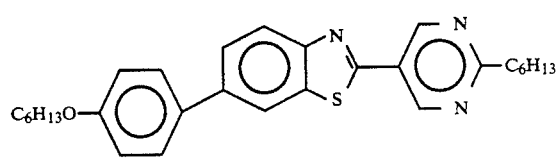 | 2 |
| | Composition L | 90 |

A ferroelectric liquid crystal device was prepared in the same manner as in Example 10 except for using the

| Ex. Comp. No. | Structural formula | wt. parts |
|---|---|---|
| I-25 | $C_5H_{11}$—〈phenyl〉—〈benzothiazole〉—$C_4H_9$ | 3 |
| I-47 | $C_9H_{19}$—〈phenyl〉—〈benzothiazole〉—$C_5H_{11}$ | 3 |
| I-427 | $C_8H_{17}$—〈phenyl〉—〈benzothiazole〉—CH=C(S)—$C_6H_{13}$ | 2 |
| I-431 | $C_5H_{11}$—〈H〉—〈benzothiazole〉—CH=C(S)—$C_6H_{13}$ | 2 |
| | Composition L | 90 |

| | 10° C. | 25° C. | 40° C. |
|---|---|---|---|
| Response time (μsec) | 559 | 298 | 169 |

COMPARATIVE EXAMPLE 19

A ferroelectric liquid crystal device was prepared in the same manner as in Example 10 except that the liquid crystal composition L prepared in Example 19 was injected into a cell. The measured values of the response time of the device were as follows.

| | 10° C. | 25° C. | 40° C. |
|---|---|---|---|
| Response time (μsec) | 668 | 340 | 182 |

EXAMPLE 20

A liquid crystal composition N was prepared by mixing the following example compounds in the indicated proportions with the liquid crystal composition L prepared in Example 19.

A ferroelectric liquid crystal device was prepared in the same manner as in Example 10 except that the above liquid crystal composition N was used, and the device was subjected to measurement of optical response time. The results of the measurement are shown below.

| | 10° C. | 25° C. | 40° C. |
|---|---|---|---|
| Response time (μsec) | 536 | 285 | 161 |

EXAMPLE 21

A liquid crystal composition O was prepared by mixing the following example compounds in the indicated proportions with the liquid crystal composition L prepared in Example 19.

| Ex. Comp. No. | Structural formula | wt. parts |
|---|---|---|
| I-124 | $C_6H_{13}$—〈benzothiazole〉—〈phenyl〉—$C_6H_{13}$ | 3 |
| I-269 | $C_2H_5CH(CH_3)(CH_2)_3O$—〈benzothiazole〉—〈phenyl〉—$OC_8H_{17}$ | 3 |
| I-298 | $C_{10}H_{21}$—〈benzothiazole〉—〈phenyl〉—〈H〉—$C_6H_{13}$ | 2 |

| Ex. Comp. No. | Structural formula | wt. parts |
|---|---|---|
| I-444 | 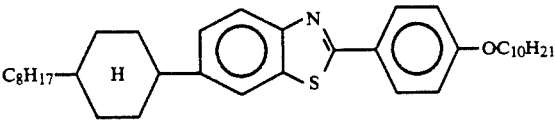 | 2 |
| | Composition L | 90 |

A ferroelectric liquid crystal device was prepared in the same manner as in Example 10 except that the above liquid crystal composition O was used, and the device was subjected to measurement of optical response time. The results of the measurement are shown below.

|  | 10° C. | 25° C. | 40° C. |
|---|---|---|---|
| Response time (μsec) | 499 | 269 | 154 |

EXAMPLE 22

A blank cell was prepared in the same manner as in Example 13 by using a 2% aqueous solution of polyvinyl alcohol resin (PVA-117, available from Kuraray K.K.) instead of the 1.5%-solution of polyimide resin precursor in dimethylacetoamide on each electrode plate. A ferroelectric liquid crystal device was prepared by filling the blank cell with the liquid crystal composition E prepared in Example 13. The liquid crystal device was subjected to measurement of optical response time in the same manner as in Example 10. The results are shown below.

|  | 10° C. | 25° C. | 40° C. |
|---|---|---|---|
| Response time (μsec) | 725 | 348 | 189 |

EXAMPLE 23

A blank cell was prepared in the same manner as in Example 13 except for omitting the SiO$_2$ layer to form an alignment control layer composed of the polyimide resin layer alone on each electrode plate. A ferroelectric liquid crystal device was prepared by filling the blank cell with the liquid crystal composition E prepared in Example 13. The liquid crystal device was subjected to measurement of optical response time in the same manner as in Example 10. The results are shown below.

|  | 10° C. | 25° C. | 40° C. |
|---|---|---|---|
| Response time (μsec) | 722 | 343 | 185 |

As is apparent from the above Examples 22 and 23, also in the cases of different device structures, the devices containing the ferroelectric liquid crystal composition E according to the present invention respectively provided a remarkably improved operation characteristic at a lower temperature and also a decreased temperature-dependence of the response speed similar to those in Example 13.

EXAMPLE 24

2-(p-hexyloxyphenyl)-6-butylbenzothiazole (Example Compound No. I-163) was prepared in the same manner as in Example 1.

Phase transition temperature (°C.)

$$\text{Cryst.} \xrightleftharpoons[68]{74} \text{SmC} \xrightleftharpoons[84]{85} \text{N} \xrightleftharpoons[97]{98} \text{Iso.}$$

EXAMPLE 25

2-(p-hexyloxyphenyl)-6-hexylbenzothiazole (Example Compound No. I-173) was prepared in the same manner as in Example 1.

Phase transition temperature (°C.)

$$\text{Cryst.} \xrightleftharpoons[58]{71} \text{SmC} \xrightleftharpoons[90]{90} \text{N} \xrightleftharpoons[102]{103} \text{Iso.}$$

EXAMPLE 26

2-(p-hexylphenyl)-6-hexyloxybenzothiazole (Example Compound No. I-207) was prepared in the same manner as in Example 1.

Phase transition temperature (°C.)

$$\text{Cryst.} \xrightleftharpoons[47]{57} \text{N} \xrightleftharpoons[88]{89} \text{Iso.}$$

EXAMPLE 27

2-(p-octyloxycarbonylphenyl)-6-octylbenzothiazole (Example Compound No. I-461) was synthesized through the following steps i) to ii).

i) 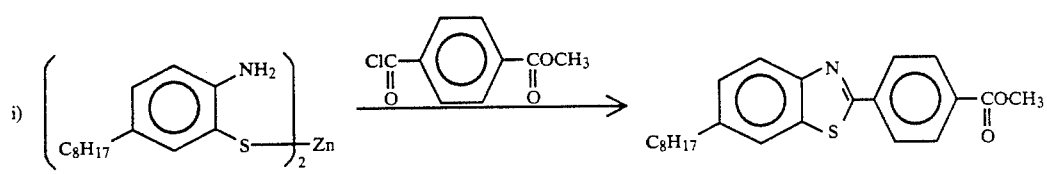

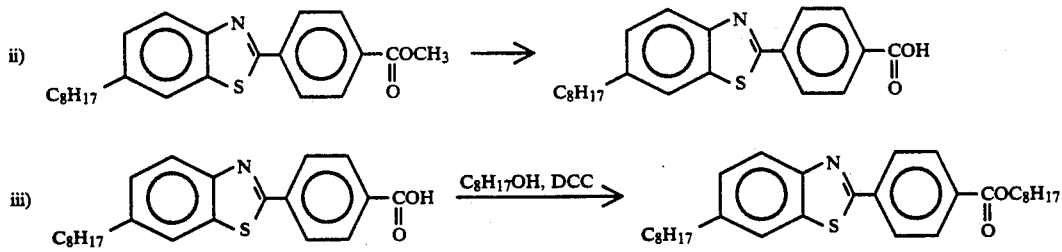

Step i) Production of 2-(p-methoxycarbonylphenyl)-6-octylbenzothiazole

To 2.26 g (11.4 mM) of methoxyterephthaloyl chloride, 3.00 g (5.57 mM) of zinc 5-octyl-2-aminobenzenethiol was added, followed by stirring for 30 minutes at 210°–216° C. After the reaction, the reaction mixture was cooled at room temperature and ethyl acetate was added thereto, followed by heating and dissolving. Under cooling with ice water, water was added to the resultant solution to precipitate a crystal. The crystal was recovered by filtration. The ethyl acetate layer was separated from the filtrate and washed with a solution of salt, followed by drying with anhydrous sodium sulfate. The resultant sodium sulfate was filtered off and the filtrate was condensed, followed by cooling to precipitate a crystal. The crystal was recovered by filtration and added to the above-prepared crystal to obtain 2.64 g of 2-(p-methoxy-carbonylphenyl)-6-octylbenzothiazole (Yield: 61.2%).

Step ii) Production of 2-(p-carboxyphenyl)-6-octylbenzothiazole

To 0.76 g (11.5 mM) of 85%-potassium hydroxide, 50 ml of ethanol was added, followed by stirring at 65° C. and dissolving. To the resultant solution, 1.80 g (4.72 mM) of 2-(p-methoxycarbonylphenyl)-6-octylbenzothiazole was added, followed by stirring for 20 minutes at 65° C. After the reaction, the reaction mixture was poured into water and 1.5 ml of concentrated hydrochloric acid was added thereto to precipitate a crystal. The crystal was recovered by filtration and sufficiently washed with water, followed by drying to obtain 1.66 g of 2-(p-carboxyphenyl)-6-octylbenzothiazole (Yield: 95.7%).

Step iii) Production of 2-(p-octyloxycarbonylphenyl)-6-octylbenzothiazole

To 0.30 g (0.82 mM) of 2-(p-carboxyphenyl)-6-octylbenzothiazole, 0.12 g (0.92 mM) of octanol and 10 ml of methylene chloride were added, followed by addition of 0.17 g (0.82 mM) of N,N'-dicyclohexylcarbodiimide (DCC) and 0.02 g of 4-dimethylamino pyridine under stirring at room temperature and further stirring for 6 hours at room temperature. After the reaction, the resultant N,N'-dicyclohexylurea was recovered by filtration, followed by washing with methylene chloride to be added to the filtrate. The solvent of the resultant filtrate was distilled-off under reduced pressure to obtain a residue. The residue was purified by silica gel column chromatography (eluent: toluene), followed by recrystallization from a mixture solvent of toluene/methanol to obtain 0.20 g of 2-(p-octyloxycarbonylphenyl)-6-octylbenzothiazole (Yield: 51.1%).

Phase transition temperature (°C.)

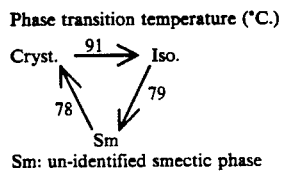

Sm: un-identified smectic phase

EXAMPLE 28

2-(p-butyloxycarbonylphenyl)-6-octylbenzothiazole (Example Compound No. I-459) was prepared in the same manner as in Example 27.

Phase transition temperature (°C.)

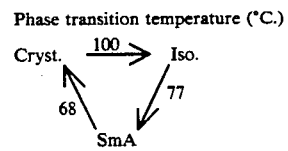

EXAMPLE 29

2-(p-hexyloxycarbonylphenyl)-6-octylbenzothiazole (Example Compound No. I-460) was prepared in the same manner as in Example 27.

Phase transition temperature (°C.)

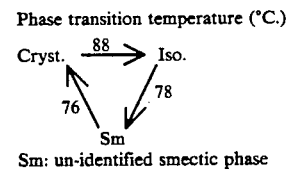

Sm: un-identified smectic phase

EXAMPLE 30

2-(p-octyloxycarbonylphenyl)-6-hexylbenzothiazole (Example Compound No. I-452) was prepared in the same manner as in Example 27.

Phase transition temperature (°C.)

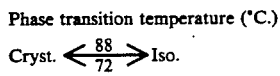

EXAMPLE 31

2-[2-(6-decyloxy)naphthyl]-6-butylbenzothiazole (Example Compound No. I-372) was prepared in the following reaction scheme.

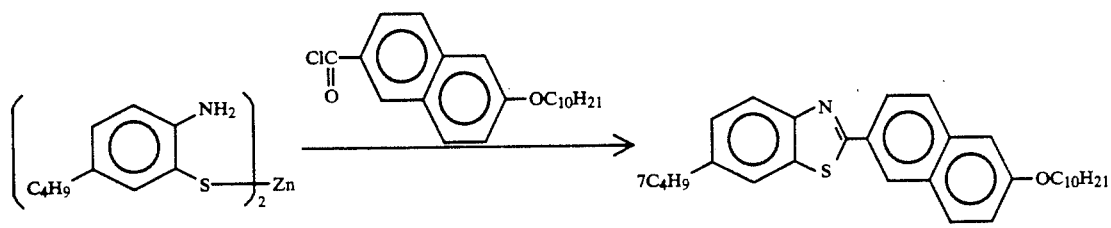

To 1.00 g (2.88 mM) of 6-decyloxy-2-naphthoyl chloride, 0.52 g (1.22 mM) of zinc 5-butyl-2-aminobenzenethiol was added, followed by stirring for 20 minutes at 200°–205° C. After the reaction, ethyl acetate was added to the reaction mixture, followed by addition of water and toluene under stirring at room temperature. The organic layer was washed with a solution of salt and dried with anhydrous sodium sulfate. The resultant sodium sulfate was filtered off, and the filtrate was condensed to precipitate a crystal. The crystal was purified by silica gel column chromatography (eluent: toluene/hexane=1/1), recrystallized from ethyl acetate and treated with activated carbon in a mixture solvent of toluene/ethyl acetate to obtain 0.62 g of 2-[2-(6-decyloxy)naphthyl]-6-butylbenzothiazole (Yield: 53.6%).

Phase transition temperature (°C.)

Cryst. $\xleftarrow{110}_{103}\xrightarrow{}$ SmA $\xleftarrow{144}_{143}\xrightarrow{}$ Iso.

EXAMPLE 32

2-(p-hexylcarbonyloxyphenyl)-6-hexylbenzothiazole (Example Compound I-462) was synthesized through the following steps i) to iii).

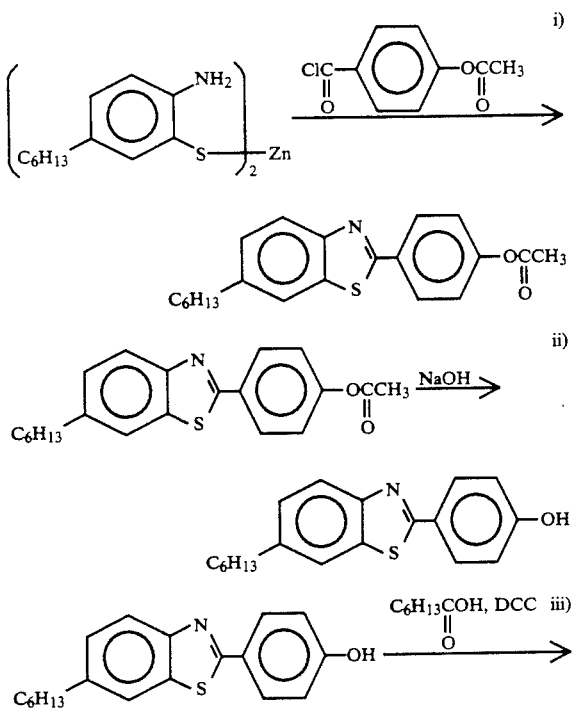

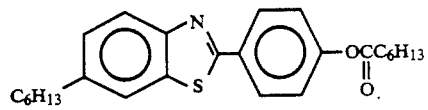

Step i) Production of 2-(p-acetoxyphenyl)-6-hexylbenzothiazole 10 ml of thionyl chloride was added to 1.80 g (10.0 mM) of p-acetoxybenzoic acid, followed by heat-refluxing for 1 hour. After the heat-refluxing, excessive thionyl chloride was distilled off under reduced pressure, followed by distilling-off thereof with benzene. To the resultant acid chloride, 2.40 g (5.0 mM) of zinc 5-hexyl-2-aminobenzenethiol was added, followed by stirring for 30 minutes at 200° C. After the reaction, the reaction mixture was cooled under room temperature. To the resultant reaction mixture, sodium carbonate aqueous solution was added, followed by extraction with ethyl acetate, washing with water, drying with anhydrous magnesium sulfate and distilling-off of the solvent to obtain a crude product. The crude product was purified by silica gel column chromatography (eluent: ethylacetate/hexane=1/10), followed by recrystallization from a mixture solvent of ethyl acetate/hexane to obtain 0.7 g of 2-(p-acetoxyphenyl)-6-hexylbenzothiazole (Yield: 20.0%).

Step ii) Production of 2-(p-hydroxyphenyl)-2-(hexybenzothiazole

To 0.7 g (2.0 mM) of 2-(p-acetoxyphenyl)-6hexylbenzothiazole, 0.25 g (6.0 mM) of sodium hydroxide and 50 ml of ethanol, followed by stirring for 10 hours at room temperature. After the reaction, the reaction mixture was poured into water, and 2 ml of concentrated hydrochloric was added thereto to precipitate a crystal. The crystal was recovered by filtration and sufficiently washed with water, followed by drying to obtain 0.6 g of 2-(p-hydroxyphenyl)-6-hexylbenzothiazole (Yield: 96.5%).

Step iii) Production of 2-(p-hexylcarbonyloxyphenyl)-6-hexylbenzothiazole

To 0.32 g (1.03 mM) of 2-(p-hydroxyphenyl)-6-hexylbenzothiazole, 0.13 g (1.03 mM) of heptanoic acid, 15 ml of methylene chloride and 5 ml of tetrahydrofuran were added, followed by addition of 0.21 g of N,N'-dicyclohexylcarbodiimide (DCC) and 0.02 g of 4-pyrrolidinopyridine under stirring at room temperature and further stirring for 6 hours at room temperature. After the reaction, the resultant N,N'-dicyclohexylurea was recovered by filtration, followed by washing with methylene chloride to be added to the filtrate. The solvent of the resultant filtrate was distilled-off under reduced pressure to obtain a residue. The residue was purified by silica gel column chromatography (eluent: toluene), followed by two times of recrystallization from a mixture solvent of toluene/methanol to obtain 0.39 g of 2-(p-hexylcarbonyloxyphenyl)-6-hexylbenzothiazole (Yield: 88.6%).

Phase transition temperature (°C.)

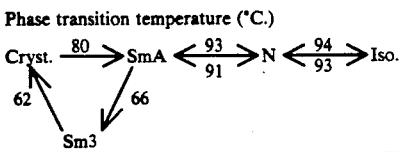

EXAMPLE 33

2-(2-fluoro-4-hexylcarbonyloxyphenyl)-6-hexylbenzothiazole (Example Compound No. I-463) was prepared in the same manner as in Example 32 except that 2-fluoro-4-acetoxybenzoic acid was used instead of p-acetoxybenzoic acid.

Phase transition temperature (°C.)

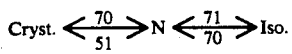

EXAMPLE 34

A liquid crystal composition P was prepared by mixing the following example compounds in the indicated proportions with the liquid crystal composition D prepared in Example 13.

| Ex. Comp. No. | Structural formula | wt. parts |
|---|---|---|
| I-459 | $C_8H_{17}$—[benzothiazole]—[phenyl]—$COC_4H_9$ (C=O) | 4 |
| I-461 | $C_8H_{17}$—[benzothiazole]—[phenyl]—$COC_8H_{17}$ (C=O) | 4 |
| I-372 | $C_4H_9$—[benzothiazole]—[naphthyl]—$OC_{10}H_{21}$ | 2 |
| Composition D | | 90 |

A ferroelectric liquid crystal device was prepared in the same manner as in Example 10 except that the above liquid crystal composition P was used, and the device was subjected to measurement of optical response time. The results of the measurement are shown below.

| | 10° C. | 25° C. | 40° C. |
|---|---|---|---|
| Response time (μsec) | 650 | 318 | 178 |

EXAMPLE 35

2-[p-(2-fluorooctyloxyloxy)phenyl]-6-hexylbenzothiazole (Example Compound No. II-11) was prepared in the following reaction schemes.

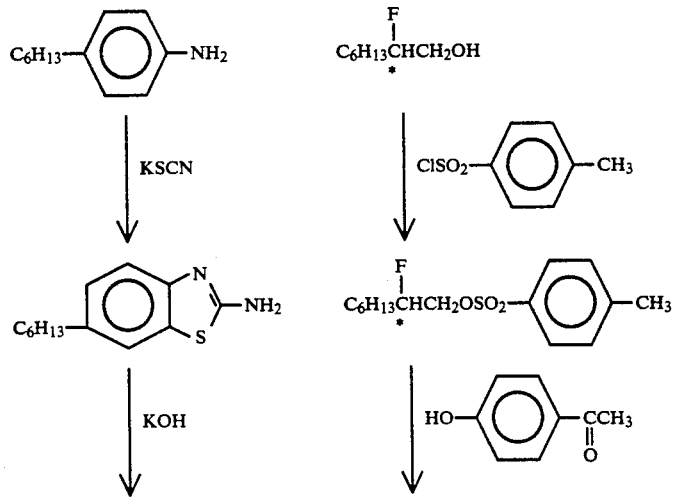

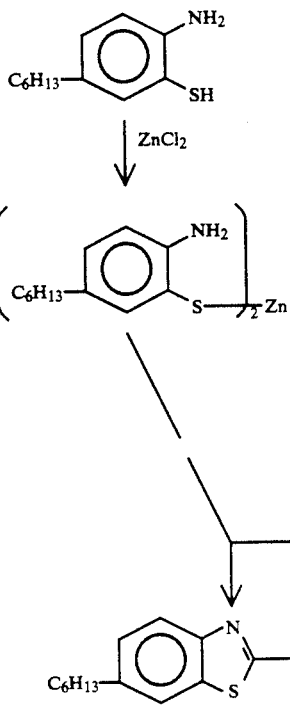
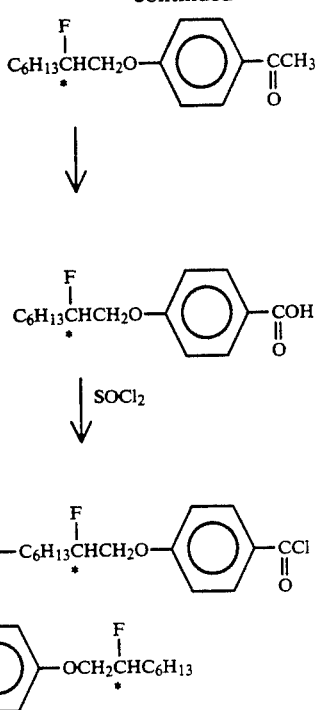

Step i) Production of 2-amino-6-hexylbenzothiazole 2-amino-6-hexylbenzothiazole was prepared in the same manner as in steps i) and ii) of Example 1.

Step ii) Production of P-(2-fluorooctyloxy)benzoic acid

To a solution of 6.7 g of 2-fluorooctanol in 25 ml of pyridine, a solution of 10.4 g of p-toluenesulfonyl chloride in 40 ml of pyridine was added dropwise in 20 minutes below 0° C. on an ice water bath, followed by stirring for 7 hours at room temperature. After the reaction, the reaction mixture was poured into 200 ml of ice water and acidified with 6N-hydrochloric acid aqueous solution, followed by extraction with methylene chloride. The organic layer was washed with water and dried with anhydrous magnesium sulfate, followed by distilling-off of the solvent to precipitate a crystal. The crystal was purified by silica gel column chromatography to obtain 12.7 g of 2-fluorooctyl-p-toluenesulfonate.

Then, 6.3 g of p-hydroxyacetophenone and 12.7 g of 2-fluorooctyl-p-toluenesulfonate were dissolved in ml of butanol. To the solution, a solution of 3.1 g of potassium hydroxide in 40 ml of butanol was added dropwise, followed by heat-refluxing for 6 hours. After the reaction, the reaction mixture was poured into 200 ml of ice water and extracted with isopropyl ether. The organic layer was washed with water and dried with anhydrous magnesium sulfate, followed by distilling-off of the solvent to precipitate a crystal. The crystal was purified by silica gel column chromatography to obtain 4.7 g of p-(2-fluorooctyloxy)acetophenone.

Then, 12. 3 g of bromine was added dropwise to a solution of 11.3 g of sodium hydroxide in 75 ml of water in 15 minutes below 0° C. on an ice water bath, followed by addition of 30 ml of dioxane to prepare a solution of sodium hydrobromite in dioxane.

To a solution of the above-prepared 4.7 g of p-(2-fluorooctyloxy)acetophenone in a mixture solvent to 120 ml of dioxane and 10 ml of water, the above-prepared solution of sodium hypobromite in dioxane was added dropwise in 40 minutes at 10° C., followed by stirring for 3 hours at room temperature. After the reaction, 10%-sodium sulfite aqueous solution was added to the reaction mixture until the color thereof was dicolorized, followed by stirring for 20 minutes, acidification with 6N-hydrochloric acid aqueous solution and addition of 500 ml of water to precipitate a crystal. The crystal was washed with water and recrystallized from a mixture solvent of methanol, ethanol and water to obtain 3.7 g of p(-2-fluorooctyloxy)benzoic acid.

Step iii) Production of 2-[p-(2-fluorooctyloxy)phenyl]-6-hexylbenzothiazole 10 ml of thionyl chloride was added to 1.07 g (4.0 mM) of p-(2-fluorooctyloxy)benzoic acid, followed by heat-refluxing for 1 hour. After the heat-refluxing, excessive thionyl chloride was distilled off under reduced pressure, followed by distilling-off thereof with benzene. To the resultant acid chloride, 0.96 g (4.0 mM) of zinc 5-hexyl-2-aminobenzenethiol was added, followed by stirring for 30 minutes at 200° C. After the reaction, the reaction mixture was cooled under room temperature. To the resultant reaction mixture, 15 ml of dilute sodium hydroxide aqueous solution was added, followed by extraction with ethyl acetate, washing with water, drying with anhydrous magnesium sulfate and distilling-off of the solvent to obtain a crude product. The crude product was purified by silica gel column chromatography (eluent: hexane/ethyl acetate=50/1) and treated with activated carbon, followed by recrystallization from ethanol to obtain 0.45 g of 2-[p-(2-fluorooctyloxy)phenyl]-6-hexylbenzothiazole (Yield: 51.0%).

Phase transition temperature (°C.)

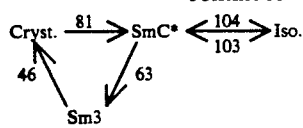

EXAMPLE 36

A liquid crystal composition Q was prepared by mixing the following compounds containing an optically active mesomorphic compound (Example Compound No. II-11 prepared in Example 35 in respectively indicated proportions.

| Ex. Comp. No. | Structural formula | Content (wt. %) |
|---|---|---|
|  | C$_8$H$_{17}$O—⟨⟩—CO—O—⟨⟩—OCH$_2$C*HC$_2$H$_5$ with CH$_3$ | 64.0 |
|  | C$_8$H$_{17}$O—⟨⟩—O—CO—⟨⟩—⟨⟩—CH$_2$C*HC$_2$H$_5$ with CH$_3$ | 16.0 |
| II-11 | C$_6$H$_{13}$—benzothiazole—⟨⟩—OCH$_2$C*HC$_6$H$_{13}$ with F | 20.0 |

Phase transition temperature (°C.)

Cryst. ⇌(12/11) SmC* ⇌(57/57) SmA ⇌(71/70) Ch. ⇌(80/80) Iso.

Separately, a liquid crystal composition R was prepared by mixing the following compounds not containing an optically active mesomorphic compound (Example Compound No. II-11) prepared in Example 35 in respectively indicated proportions.

| Structural formula | Contents (wt. %) |
|---|---|
| C$_8$H$_{17}$O—⟨⟩—CO—O—⟨⟩—OCH$_2$C*HC$_2$H$_5$ with CH$_3$ | 80 |
| C$_8$H$_{17}$O—⟨⟩—O—CO—⟨⟩—⟨⟩—CH$_2$C*HC$_2$H$_5$ with CH$_3$ | 20 |

Phase transition temperature (°C.)

Cryst. ⇌(20/18) SmC* ⇌(53/52) SmA ⇌(65/64) Ch. ⇌(76/75) Iso.

Two ferroelectric liquid crystal devices were respectively prepared in the same manner as in Example 10 except that the above liquid crystal compositions Q and R were used, and the devices were respectively subjected to measurement of the magnitude of spontaneous polarization Ps and optical response time. The results of the measurement are shown below.

| Temperature (°C.) | Composition Q | Composition R |
|---|---|---|
| <Ps (nC/cm$^2$)> | | |
| 25 | 38.9 | 2.5 |
| 35 | 29.2 | 1.9 |
| 45 | 19.4 | 0.9 |
| <Response time (μsec)> | | |
| 25 | 340 | 1913 |
| 35 | 154 | 1028 |
| 45 | 86 | 630 |

As is apparent from the above results, the liquid crystal composition Q containing the optically active mesomorphic compound of the present invention showed a broader temperature range assuming a chiral smectic C (SmC*) phase, a larger spontaneous polarization and high speed responsiveness compared with the liquid crystal composition R not containing the optically active mesomorphic compound of the invention.

EXAMPLE 37

A liquid crystal composition S was prepared by mixing the following compounds containing an optically active mesomorphic compound (Example Compound No. II-11) prepared in Example 35 in respectively indicated proportions.

| Ex. Comp. No. | Structural formula | Content (wt. %) |
|---|---|---|

-continued

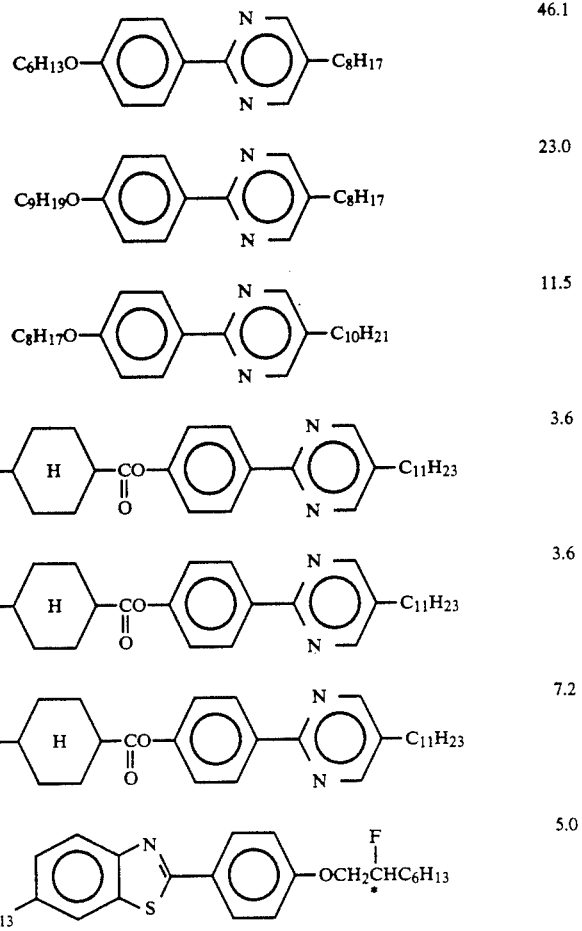

| | |
|---|---|
| | 46.1 |
| | 23.0 |
| | 11.5 |
| | 3.6 |
| | 3.6 |
| | 7.2 |
| II-11 | 5.0 |

Phase transition temperature (°C.)

Cryst. $\xrightarrow{9}$ SmC* $\xrightarrow{59}$ SmA $\xrightarrow{64}$ Ch. $\xrightarrow{78}$ Iso.

A ferroelectric liquid crystal device was prepared in the same manner as in Example 10 except that the above liquid crystal composition S was used, and the devices were respectively subjected to measurement of the magnitude of spontaneous polarization Ps and optical response time. The results of the measurement are shown below.

| Temperature (°C.) | Composition S |
|---|---|
| <Ps (nC/cm²)> | |
| 10 | 4.2 |
| 30 | 2.7 |
| 45 | 1.8 |
| <Response time (μsec)> | |
| 10 | 592 |
| 30 | 264 |
| 45 | 166 |

EXAMPLE 38

Two glass plates each provided with an ITO film were coated with a solution of polyimide resin precursor (SP-510, available from Toray K.K.) by a spinner coater. Each coating film was subjected to alignment treatment by rubbing. The two glass plates were applied each other so that their rubbed direction were perpendicular to each other to form a blank cell having a cell gap of 8 microns.

Then, a nematic liquid crystal composition (Lixon GR-63: biphenyl liquid crystal mixture, available from Chisso K.K.) was injected into the above-prepared cell to provide a TN (twisted nematic) type cell. When the TN type cell was observed by a polarizing microscope, a reverse domain (i.e., a striped pattern) was caused to occur.

Another TN type was prepared in the above-mentioned manner except that a liquid crystal mixture comprising 99 wt. parts of Lixon GR-63 and 1 wt. part of an optically active mesomorphic compound (Example Compound No. II-11) prepared in Example 35 was used instead of Lixon GR-63 alone. When such a TN type cell was observed by the polarizing microscope, a uniform nematic phase free of the above-mentioned reverse domain was assumed.

Accordingly, the mesomorphic compound according to the present invention was effective in preventing occurrence of the reverse domain.

EXAMPLE 39

2-[4-(5-octylpyrimidine-2-yl)phenyl]-6-hexylbenzothiazole (Example Compound No. I-475) was prepared in the same manner as in Example 6 except that 4-(5- octylpyrimidine-2-yl)benzoic acid was used instead of p-(trans-4-pentylcyclohexyl)benzoic acid.

Phase transition temperature (°C.)

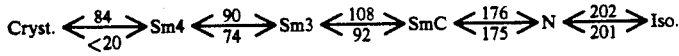

As described hereinabove, according to the present invention, there is provided a mesomorphic compound having good electric field-responsiveness. There are also provided a mesomorphic compound, a liquid crystal composition containing the compound, and a liquid crystal device using the composition which shows a good switching characteristic, an improved low-temperature operation characteristic and a decreased temperature-dependence of response speed. Further, the liquid crystal composition containing the mesomorphic compound according to the present invention and the liquid crystal device using such a composition provide improved response speed and effectively prevent occurrence of a reverse domain. According to the present invention, there is further provided a display apparatus utilizing the liquid crystal device of the present invention as a display unit, which shows good display characteristics in combination with a light source, a drive circuit, etc.

What is claimed is:

1. An optically active mesomorphic compound represented by the following formula (II):

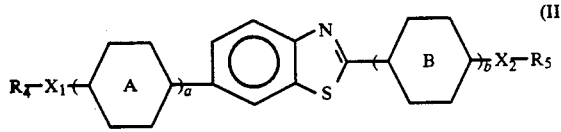

wherein $R_4$ and $R_5$ independently denote an alkyl group having 1-18 carbon atoms optionally substituted with an alkoxy group, at least one of $R_4$ and $R_5$ has an asymmetric carbon atom connected to halogen; $X_1$ and $X_2$ independently denote a single bond, —O—,

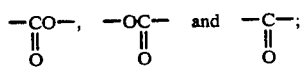

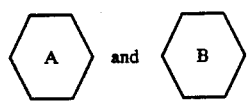

independently denote

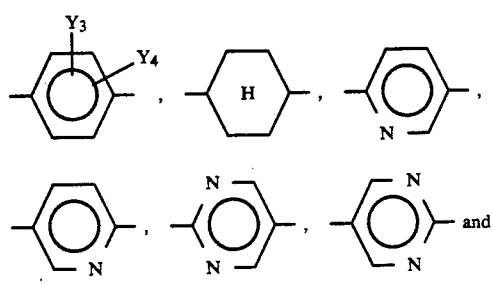

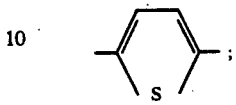

$Y_3$ and $Y_4$ independently denote hydrogen, fluorine, chlorine, bromine, —CH$_3$, —CN and —CF$_3$; and a and b independently denote 0 or 1.

2. An optically active mesomorphic compound according to claim 1, wherein halogen comprises fluorine or chlorine.

3. An optically active mesomorphic compound according to claim 1, wherein one of $R_4$ and $R_5$ denotes any one of the following groups (i) to (iii):

(i) n-alkyl group having 1-18 carbon atoms, particularly having 3-12 carbon atom;

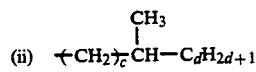

wherein c denotes an integer of 0-7 and d denotes an integer of 1-9 (optically active or inactive when d denotes an integer of 2 or above); and

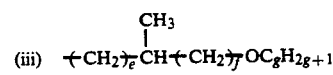

wherein e denotes an integer of 0-7, f denotes 0 or 1, and g denotes an integer of 1-14 (optically active or inactive).

4. An optically active mesomorphic compound according to claim 1, wherein

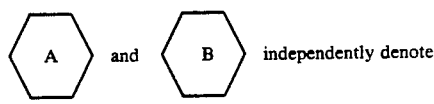

in a case wherein a = b = 1 and independently denote

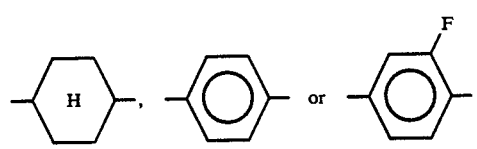

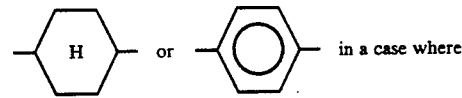

a = 1 and b = 0 or a = 0 and b = 1.

5. A liquid crystal composition comprising at least two mesomorphic compounds, at least one of which is an optically active mesomorphic compound of the formula (II) according to claim 1.

6. A liquid crystal composition according to claim 5, which assumes a chiral smectic phase.

7. A liquid crystal composition according to claim 6, which contains 0.1-99 wt. % of an optically active mesomorphic compound of the formula (II).

8. A liquid crystal composition according to claim 6, which contains 1-90 wt. % of an optically active mesomorphic compound of the formula (II).

9. A liquid crystal device, comprising a pair of electrode plates and a liquid crystal composition according to claim 5 disposed between the electrode plates.

10. A liquid crystal device according to claim 9, which further comprises an insulating alignment control layer.

11. A display apparatus comprising a liquid crystal device according to claim 9, and voltage application means for driving the liquid crystal device.

12. A display apparatus according to claim 11, wherein the liquid crystal device constitute a display panel wherein the alignment direction of liquid crystal molecules is switched by utilizing ferroelectricity of the liquid crystal composition to effect display.

13. A display method comprising:
providing a liquid crystal composition according to claim 5 having ferroelectricity, and
switching the alignment direction of liquid crystal molecules based on the ferroelectricity of the liquid crystal composition to effect display.

14. A display method, comprising:
providing a liquid crystal device according to claim 9, and
switching the alignment direction of liquid crystal molecules to effect display based on the ferroelectricity of the liquid crystal composition contained in the liquid crystal device.

* * * * *

UNITED STATES PATENT AND TRADEMARK OFFICE
CERTIFICATE OF CORRECTION

PATENT NO. : 5,284,599
DATED : February 8, 1994
INVENTOR(S) : TAKASHI IWAKI, ET AL.

Page 1 of 6

It is certified that error appears in the above-identified patent and that said Letters Patent is hereby corrected as shown below:

ON TITLE PAGE

In [54] Title: "SAME DISPLAY" should read --SAME AND DISPLAY--.

In [57] Abstract, Line 10:

"
$\begin{array}{c}-C-N-,\\ \parallel \; | \\ O \; R_3\end{array}$
"  should read  --
$\begin{array}{c}-C-N-,\\ \parallel \; | \\ O \; R_3\end{array}$
--.

In [57] Abstract, Line 11:

" CH=CH– " should read -- –CH=CH– --.

COLUMN 1

Line 4, "SAME DISPLAY" should read --SAME AND DISPLAY--.
Line 53, "so called" should read --so-called--.

COLUMN 2

Line 6, "is" should read --are--.
Line 36, "electric" should read --electric field--.
Line 63, "$\eta$," should read --$\tau$,--.

COLUMN 5

Line 23, "and" should be deleted.

UNITED STATES PATENT AND TRADEMARK OFFICE
CERTIFICATE OF CORRECTION

PATENT NO. : 5,284,599
DATED : February 8, 1994
INVENTOR(S) : TAKASHI IWAKI, ET AL.

It is certified that error appears in the above-identified patent and that said Letters Patent is hereby corrected as shown below:

COLUMN 7

Line 65, "found that" should read --discovered--.

COLUMN 8

Line 43, "(c): (a)" should read --(c): ¶ (a)--.
Line 60, "-OCH$_3$" should read -- -OCH$_3$ or--.

COLUMN 43

Formula (I-215): "C$_8$H$_{17}$O " should read --C$_8$H$_{17}$O  --.

COLUMN 87

Formula (IIIb), "-X$_1$-" should read -- -X$_1$'- --.

COLUMN 88

Line 47, "-OCH$_2$" should read -- -OCH$_2$- --.

COLUMN 91

Line 26, "-CH$_2$O" should read -- -CH$_2$O- --.

COLUMN 92

Line 37, "g" should read --q--.

COLUMN 94

Line 50, "(IVcd):" should read --(IVcb):--.

UNITED STATES PATENT AND TRADEMARK OFFICE
CERTIFICATE OF CORRECTION

PATENT NO. : 5,284,599
DATED : February 8, 1994
INVENTOR(S) : TAKASHI IWAKI, ET AL.

It is certified that error appears in the above-identified patent and that said Letters Patent is hereby corrected as shown below:

COLUMN 98

Line 10, "follwoing" should read --following--.

COLUMN 99

Line 25, "$-(CH_2)_p-$" should read --$-(CH_2)_T-$--.
Line 67, "$X_1'-$" should read --$X_1'$--.

COLUMN 101

Line 19, "formula (x)," should read --formula (X),--.

COLUMN 104

Line 60, "atom;" should read --atoms;--.

COLUMN 117

Formula (II-68), "$C_8H_{19}$" should read --$C_8H_{17}$--.

COLUMN 120

Line 1, "un-identified" should read --unidentified--.

COLUMN 136

Line 1, "f" should read --of--.
Line 17, "30.0g(0.128M)," should read --30.0g(0.128M) of 2-amino-6-hexylbenzothiazole,--.

UNITED STATES PATENT AND TRADEMARK OFFICE
CERTIFICATE OF CORRECTION

PATENT NO. : 5,284,599
DATED : February 8, 1994
INVENTOR(S) : TAKASHI IWAKI, ET AL.

Page 4 of 6

It is certified that error appears in the above-identified patent and that said Letters Patent is hereby corrected as shown below:

COLUMN 138

Line 42, "traction" should read --extraction--.

COLUMN 140

Line 19, "wit" should read --with-- and "off" (second occurrence) should be deleted.

COLUMN 141

Line 48, "15 second" should read --15 seconds--.
Line 51, "above described" should read --above-described--.
Line 63, "(Lixoin" should read --(Lixon--.

COLUMN 151

Line 16, "int he" should read --in the--.

COLUMN 161

Line 59, "4-dimethylamino pyridine" should read --4-dimethylamino-pyridine--.

COLUMN 162

Line 25, "un-identified" should read --unidentified--.
Line 52, "un-identified" should read --unidentified--.

COLUMN 164

Line 9, "7$C_4H_9$" should read --$C_4H_9$--.

UNITED STATES PATENT AND TRADEMARK OFFICE
CERTIFICATE OF CORRECTION

PATENT NO. : 5,284,599
DATED : February 8, 1994
INVENTOR(S) : TAKASHI IWAKI, ET AL.

It is certified that error appears in the above-identified patent and that said Letters Patent is hereby corrected as shown below:

COLUMN 164

Line 42, "(hexybenzothiazole" should read --hexylbenzothiazole--.
Line 44, "6hexylben-" should read --6-hexylben- --.
Line 46, "ethanol," should read --ethanol were added,--.

COLUMN 166

Line 45, "(2-fluorooctyloxyloxy)" should read --(2-fluorooctyloxy)--.

COLUMN 167

Line 34, "P-" should read --p- --.
Line 50, "ml" should read --35 ml--.
Line 61, "12. 3g" should read --12.3g--.

COLUMN 169

Line 13, "No. II-11" should read --No. II-11)--.

COLUMN 171

Line 67, "applied" should read --applied against--.
Line 68, "direction" should read --directions--.

COLUMN 174

Line 67, "A." should read --A--.

UNITED STATES PATENT AND TRADEMARK OFFICE
CERTIFICATE OF CORRECTION

PATENT NO. : 5,284,599
DATED : February 8, 1994
INVENTOR(S) : TAKASHI IWAKI, ET AL.

It is certified that error appears in the above-identified patent and that said Letters Patent is hereby corrected as shown below:

COLUMN 175

Line 17, "constitute" should read --constitutes--.

Signed and Sealed this

Third Day of January, 1995

Attest:

BRUCE LEHMAN

Attesting Officer

Commissioner of Patents and Trademarks